(12) United States Patent
Matos

(10) Patent No.: US 12,377,264 B2
(45) Date of Patent: Aug. 5, 2025

(54) IMPLANTABLE MEDICAL DEVICE WHICH MAY BE CONTROLLED FROM CENTRAL STATION

(71) Applicant: Jeffrey Matos, New Rochelle, NY (US)

(72) Inventor: Jeffrey Matos, New Rochelle, NY (US)

(*) Notice: Subject to any disclaimer, the term of this patent is extended or adjusted under 35 U.S.C. 154(b) by 655 days.

(21) Appl. No.: 17/380,906

(22) Filed: Jul. 20, 2021

(65) Prior Publication Data

US 2022/0008720 A1    Jan. 13, 2022

Related U.S. Application Data

(60) Division of application No. 14/816,382, filed on Aug. 3, 2015, now Pat. No. 11,065,442, which is a
(Continued)

(51) Int. Cl.
*A61N 1/08* (2006.01)
*A61B 5/00* (2006.01)
*A61B 5/08* (2006.01)
*A61B 5/318* (2021.01)
*A61N 1/372* (2006.01)
(Continued)

(52) U.S. Cl.
CPC .............. *A61N 1/08* (2013.01); *A61B 5/0004* (2013.01); *A61B 5/0816* (2013.01); *A61B 5/318* (2021.01); *A61B 5/4836* (2013.01); *A61B 5/747* (2013.01); *A61N 1/37247* (2013.01); *A61N 1/37282* (2013.01); *G16H 20/40* (2018.01); *G16H 40/67* (2018.01); *A61B 5/021* (2013.01); *A61B 5/1172* (2013.01); *A61B 5/14551* (2013.01); *A61B 5/6826* (2013.01); *A61B 2560/0209* (2013.01); *A61B 2562/0204* (2013.01); *A61N 1/3622* (2013.01); *A61N 1/3628* (2013.01); *A61N 1/3702* (2013.01); *A61N 1/37205* (2013.01); *A61N 1/37254* (2017.08); *A61N 1/3756* (2013.01); *A61N 1/395* (2013.01); *A61N 1/3956* (2013.01); *A61N 1/39622* (2017.08)

(58) Field of Classification Search
CPC ... A61N 1/37247; A61N 1/37254; A61N 1/08
See application file for complete search history.

(56) References Cited

U.S. PATENT DOCUMENTS

2001/0031071 A1* 10/2001 Nichols .................. A61B 5/117
                                                                  382/115

* cited by examiner

*Primary Examiner* — Alyssa M Alter
(74) *Attorney, Agent, or Firm* — Morris Law Group; Robert W Morris

(57) ABSTRACT

An implantable electrical stimulating device and system provides for a remote determination of the identity of the person in whom the stimulating device is implanted. The stimulating device may be a pacemaker, a defibrillator, another medical device or a non-medical device. The bases for the remote identification are (1) the comingling of (A) biologic identification information of the person linked to the stimulating device, and (B) information pertaining to a physiologic parameter (e.g. heart rate information) of that person, and (2) the modulation of the physiologic parameter by external information. Embodiments of the invention in which the stimulating device is external to the person are possible. By utilizing the apparatus providing for the remote identification of a person plus stimulating device, one aspect of secure communication—that based on reliable mutual identification of each participant in a communication—is achieved.

19 Claims, 50 Drawing Sheets

Related U.S. Application Data continuation-in-part of application No. 14/457,944, filed on Aug. 12, 2014, now Pat. No. 9,095,727, which is a continuation-in-part of application No. 14/076,521, filed on Nov. 11, 2013, now Pat. No. 8,805,529, which is a continuation of application No. 13/795,520, filed on Mar. 12, 2013, now abandoned, which is a division of application No. 12/154,079, filed on May 19, 2008, now Pat. No. 8,473,065.

(60) Provisional application No. 60/930,525, filed on May 17, 2007.

(51) Int. Cl.
*G16H 20/40* (2018.01)
*G16H 40/67* (2018.01)
*A61B 5/021* (2006.01)
*A61B 5/1172* (2016.01)
*A61B 5/1455* (2006.01)
*A61N 1/362* (2006.01)
*A61N 1/37* (2006.01)
*A61N 1/375* (2006.01)
*A61N 1/39* (2006.01)

DARK VERTICAL AND
HORIZONTAL LINES
REPRESENT ECG
SENSING AREA

LIGHT COLORED REGIONS
REPRESENT FINGERPRINT
SENSING AREAS

TOP VIEW

SIDE VIEW

IMPLANTABLE MEDICAL DEVICE WHICH MAY BE CONTROLLED FROM CENTRAL STATION

CROSS-REFERENCE TO RELATED PATENTS AND PATENT APPLICATIONS

This application is a divisional of U.S. patent application Ser. No. 14/816,382, filed Aug. 3, 2015, which will issue on Jul. 20, 2021 as U.S. Pat. No. 11,065,442, and which, in turn, was a continuation-in-part of U.S. patent application Ser. No. 14/457,944, filed Aug. 12, 2014, which issued on Aug. 4, 2015 as U.S. Pat. No. 9,095,727 and which, in turn, was a continuation-in-part of U.S. patent application Ser. No. 14/076,521, filed Nov. 11, 2013, which issued on Aug. 12, 2014 as U.S. Pat. No. 8,805,529 and which, in turn, was a continuation of U.S. patent application Ser. No. 13/795,250 filed Mar. 12, 2013 and which issued on Nov. 12, 2013, as U.S. Pat. No. 8,583,251 and which, in turn, was a continuation of, and claimed priority from U.S. patent application Ser. No. 12/154,079, filed May 19, 2008, which issued on Jun. 25, 2013 as U.S. Pat. No. 8,473,065 and which, in turn, claimed priority from the Provisional Application No. 60/930,525 filed May 17, 2007.

The subject matter of this application is also related to that of U.S. Pat. Nos. 7,277,752; 8,214,043; 8,233,672; 8,565,882; 8,655,450; 8,706,225; 9,082,156; 9,152,837; 9,265,952; 9,545,520; 9,928,510 and 10,037,408; all of which are incorporated herein by reference.

BACKGROUND OF THE INVENTION

An early generation of implantable cardioverter-defibrillators, "ICDs" had one programmable function: on and off. The modern version of the device has dozens of programmable parameters. In fact, it is now not uncommon for physicians who regularly use such devices to not be fully versed in all of the possible programming complexities of the devices that they implant. Furthermore, the optimal value of some programmable parameters can not be know at the time of device implantation. Physicians will not uncommonly guess at the values to be programmed for anti-tachycardia pacing, because they may not be able to accurately reproduce the tachycardia that a patient may later have. It is therefore not uncommon for physicians to reprogram such parameters, weeks, months or years later, after the occurrence of the actual event showed that they had not guessed well. Occasionally, the examples are striking. A patient, for example with an ICD and both ventricular tachycardia and atrial fibrillation may get not just one but quite a few inappropriate defibrillator shocks, because of an inappropriately selected programmed rate cutoff, stability parameter, etc. The opposite sort of phenomenon may also occur. For example, a patient with known ventricular tachycardia, "VT", at 200 beats per minute, "bpm", may have the VT detect rate of an ICD programmed to 180, and may later collapse because of an unexpected episode of VT below the rate cutoff.

Occasionally, the malfunctioning of an implanted device can have very serious consequences. The Ventritex V-110 defibrillator at one point had a failure mode which resulted in the sudden death of at least one patient. The "fix" for it, was a programming fix, wherein the downloading of certain instructions prevented the device from being subject to this malfunction.

The explosive growth of modern communication systems allows for the possibility of remote supervision and management of implantable devices, and addressing of the aforementioned problems. An ICD which may be providing numerous inappropriate shocks over a short time period—either due to device malfunction, lead malfunction or inappropriate programming of a properly functioning system, could be remotely identified and reprogrammed, for example.

A variety of other devices which perform critical functions which remote control could enhance. These include cardiac pumps, insulin pumps, brain stimulating devices and others.

There are certain requirements that must be fulfilled if some of the autonomy of device function is to be impinged on. Remote control over a faulty communication link could create problems instead of solving them, so reliability of communications, careful communication monitoring, redundancy and contingency planning, are all features of a remotely controllable implantable device. Since the communication process uses battery power, judicious power management is also a necessity.

Since the gaining of access to IMD control by an inappropriate or non-authorized person may have major or dire consequences, it is of value to prevent system access by any such inappropriate person.

One approach to the problem is simply to require an alphanumeric user identification. Such an approach has the obvious limitation of easily breached device security, upon loss, theft, or other unintended acquisition of the device access information.

A more secure approach is requiring the user to input a "biologic identifier"—e.g. a fingerprint, an iris pattern, retinal blood vessel pattern, palm or finger blood vessel pattern, facial image, voice or voice print, etc. These too can be "hacked", since it is possible to obtain such biologic identification without the agreement of the person whose identification is purloined.

A still more secure approach, presented herein relies on more secure systems of user identification.

SUMMARY OF THE INVENTION

Hereinbelow: Medical Expert, "ME", refers to either a person (a "medical professional") or an expert computational system. The word "user" refers to a person (or entity) wishing to gain access to the control of a remotely controllable device. In some paragraphs hereinbelow, the person in whom a medical device is implanted is referred to as the "owner".

The inventions disclosed herein concern methods and apparatus for remotely controlling implantable medical devices such as ICDs, pacemakers, drug infusion pumps, brain stimulators etc. In order to conserve battery power, the communication link between the device and a medical expert is designed to function only when needed. Such need is defined by preprogramming certain notification criteria, such that the device initiates communication with a ME only when the assistance of that ME may be needed. Following notification the ME may observe the sensor information that the device observes in making a device management decision. Furthermore, the ME may have access to additional information e.g. historical information within the device memory, historical information about the particular patient from one or more accessible databases, and information about a plurality of patients with the device from still other databases. The ME may have a variety of control-sharing relationships with the implanted device ranging from complete control (with simultaneous complete inhibition of internal control circuits), or a sharing arrangement in which, for example, both the ME and the control circuits of the IMD may be able to influence treatment. Following such an encounter, the ME may modify the device functioning by reprogramming a number of parameters (e.g. notification parameters, a value of one or more parameters which define a threshold for treatment, the actual treatment parameters, battery management, and the nature of the control-sharing arrangement for future episodes involving notification).

To provide security against unauthorized persons gaining access to the control of the IMD, a number of inventive approaches are presented herein.

In a first preferred embodiment, user identification is performed during the inputting of a control signal to control an IMD.

In a second preferred embodiment, the system of the first embodiment is enhanced by remotely manipulating user biologic features (e.g. the remote control of a light source which causes light to impinge on the user's eye, which in turn causes a change in the size of the user's iris and pupil).

The IMD may be any implantable medical device, including but not limited to: a pacemaker, a defibrillator, an infusion pump, a closed loop diabetes control device, a brain stimulator, a nerve stimulator, a muscle stimulator, a gastric stimulator, a carotid sinus stimulator, a left or right ventricular assist device, a totally implanted heart, a bladder control device, a pain management device and other such devices as are known in the art.

The devices discussed herein are implanted, but the application of this technology to external medical devices parallels that of the implanted versions.

Furthermore, the user ID approach described herein is applicable to users of all electronic systems in which security is desirable including medical record systems, data banks, credit card and other electronically interactive remote business transactions, security buying, trading and selling, legal contract execution, voting systems, public government management systems, corporate and small business management systems, remote aircraft control, remote control of ground, water and space-based vehicles, personal communications, cloud based data management, etc.

In addition to allowing the IMD to establish that the source of an incoming command or other information incoming information is identified with an extremely high degree of reliability, it is important for the person or device sending information to the IMD, that the identity of both the IMD and its "owner"—i.e. the person in whom the IMD is implanted, are known with an extremely high degree of certainty.

The inventive matter which follows is intended to allow the person who issues device commands to make sure that the command got to the correct device. A simple way of doing this is to have the IMD return a confirmation signal to the command-sending person, indicating both receipt of the command and the imbedded device ID number of the receiving IMD.

However, since the device performs actions which are potentially life-saving or life-ending (in the event of receipt and execution of a wrong command), some more robust identification of the person (rather than, or in addition to the device) is desirable. For external devices, this is a must. Such identification is desirable even for internal devices, since a clerical error in recording the identity of the person in whom a particular device is implanted (or in recording a device ID number) could have disastrous results. Information routing to an IMD is solely based on a device ID number, can be made more robust by assuring that the device owner is the correct recipient; and a system of highly robust biologic identification of the owner is a very reliable way to accomplish the desired error free recipient selection process.

For pacemakers and defibrillators, a preferred embodiment of the invention, the two tasks that accomplish this are (a) the controlling person ("CP") sending a signal to the device which causes a very brief alteration in the owner's electrocardiogram ("ECG") or pulse (e.g. as measured by pulse oximetry)—for example an acceleration of the heart rate by a few beats per minute, and (b) confirming this heart rate acceleration by returning a signal to the CP that contains a merged biologic identifier of the owner (a fingerprint, for example) and proof of the heart rate acceleration. Such biologic identification allows the CP to know which device he or she is controlling, and the identity of the device owner.

The figures and specification which follow show that this merger can be accomplished in the following ways:

a fingerprint identification device with admixed and or adjacent conductive elements which allows spatially and temporally matched recording of both the fingerprint and the accelerated heartbeat (or other temporary electrocardiographic perturbation): The ECG signal is obtained from the bio-identified finger. (This embodiment would also require at least one second ECG electrode—which could be another bio-identified finger, or a non-identified body part.) And since the ECG signal is obtained from the bio-identified finger, proof is thereby provided that the medical device with which the CP is communicating is the device which has caused the accelerated heartbeat of the person corresponding to the fingerprint.

a fingerprint ID device with admixed and or adjacent components to generate a pulse oximetry ("PO") signal. PO apparatus determines (on a multiple times per second basis) the ratio of oxygenated blood to de-oxygenated blood. These two blood forms have different visible (and infrared) light spectra, and a PO device, fitted onto a finger, determines moment to moment blood flow by comparing ratios of the amount of light transmitted through a fingertip, for example at wavelengths in the red part of the visible spectrum, and at one or more infrared wavelengths. The light sources for accomplishing such measurement abut or are in close proximity to the fingertip. Thus, in this embodiment of the invention, the PO output signal confirms the heartbeat perturbation. And since the PO signal is obtained from the bio-identified finger (which provides a fingerprint), proof is thereby provided that the medical device with which the CP is communicating is the device which has caused the perturbed heartbeat of the person corresponding to the fingerprint.

Another means of demonstrating a pulse visibly is to observe a pulsating blood vessel. Implicit in such observation is a greater degree of uncertainty of data quality because of substantial person-to-person variation in anatomy, and in particular, variation in the observability of the candidate vessels. The observable vessels which are in close proximity to a biologic identifier include: (i) the carotid artery, (ii) the jugular vein, and (iii) blood vessels of the retina. Since each of these is in the vicinity of another biologic identifier (i.e. the face or the iris), positioning a camera such that it can image both the biologic identifier and the vessel are possible.

The provision, by the owner, of ECG or pulse oximetry information may be viewed as the implicit granting of permission for the CP to execute an alteration to the IMD functioning. Additional embodiments of the invention entail explicit granting of permission—in which the CP notifies the IMD owner of an intended CP-induced alteration, and in which the owner must positively allow permission to proceed.

In another preferred embodiment of the invention, the pacing device can be substituted for by a stimulation device which does not have to cause cardiac activation. Such a device could be a pacemaker (or ICD) outputting subthreshold stimuli (in the atrium or a ventricle), a leadless pacemaker, or a stimulation device which does not provide cardiac stimulation at all. The broadening of the choice of stimulation device, and the increasing ease with which they are deployed makes these alternate versions of the invention attractive. It is furthermore possible to produce any of these embodiments as an external pacing device; however in these cases, the degree of certainty of the association between the biologic identifier and the physiologic signals is less certain than in the implanted embodiments. The reason for this is that it is highly impractical to switch one implanted device for another (and thereby defeat the logic and outcome of the owner identification process), while it is much easier to make such a switch with an external device.

Since this embodiment of the invention provides for a very high degree of certainty in the identification of each of two parties who are in communication—the device owner and the person (or device) at a second location—it is possible to use the invention to set up a highly secure method of communication. At least one of the parties would have to have the stimulation device referred to hereinabove—preferably implanted.

The sensing devices which are presented hereinabove and hereinbelow could be embedded in a special smart phone, or could be accomplished by a smart phone plug in apparatus and app.

BRIEF DESCRIPTION OF THE DRAWINGS

FIG. 2 C is a representational block diagram of a system including an IMD, a sensor and a remote station operated by a computational device and a further remote station operated by a human medical expert.

DETAILED DESCRIPTION OF THE PREFERRED EMBODIMENTS

Figure 1:
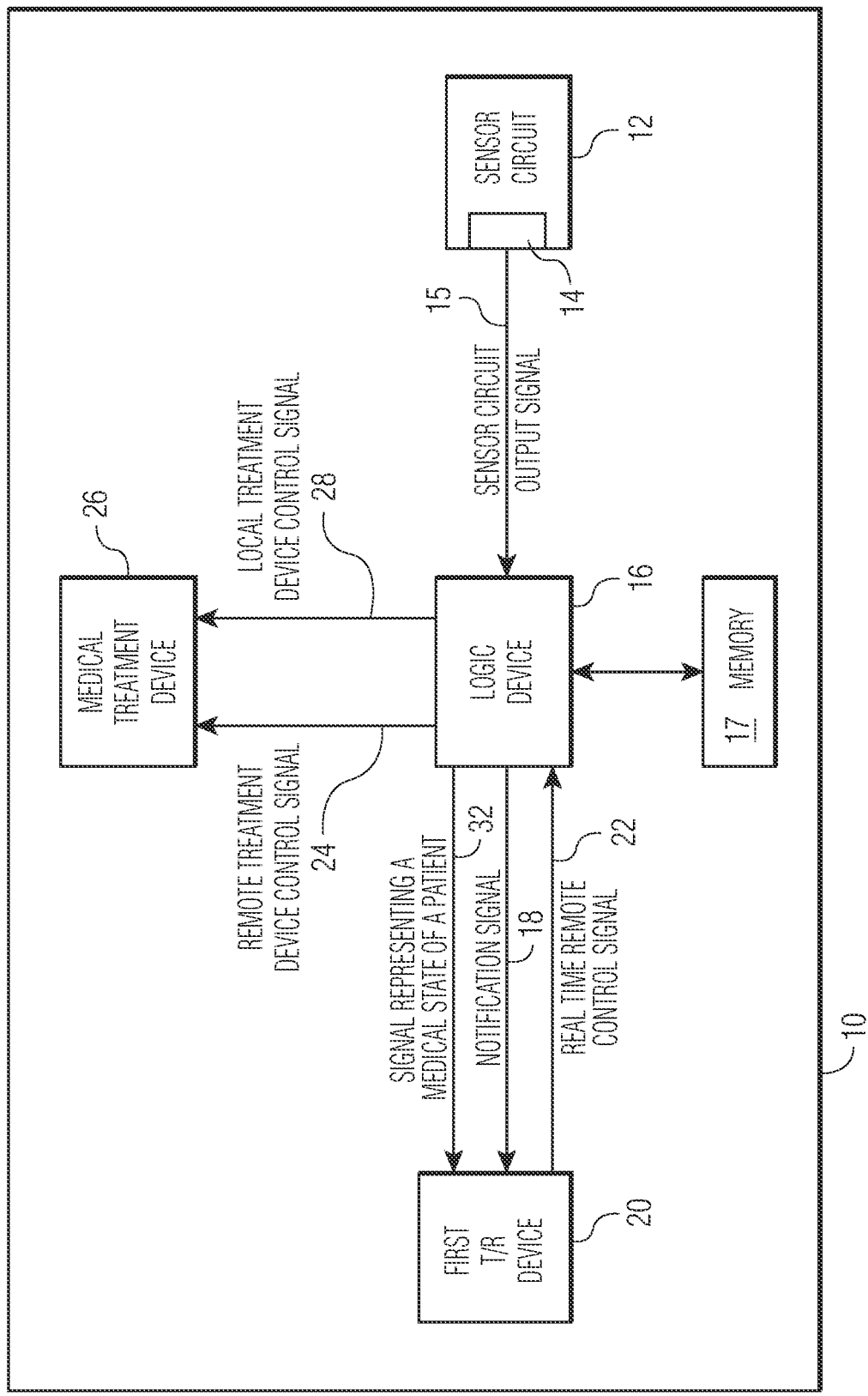
FIG. 1 is a representational block diagram of an implantable medical device ("IMD") which may be remotely controlled.

FIG. 1 shows an implantable medical device 10 which has the capacity to notify a remotely located medical expert. Sensor circuit 12, with output 14, outputs sensor circuit output signals 15. The signals contain data regarding the measurement of at least one medical parameter, a parameter which allows the logic device 16 of the IMD to make treatment decisions. 15 may be an analog signal or a digitized one, as is known in the art. Means for amplification, of 15 and other techniques for signal management as are known in the art, may reside within 12. The sensor circuit is coupled to a sensor, as discussed hereinbelow.

Logic device 16 analyzes signals 15 to determine if there is a need for (a) treatment of a medical abnormality, and/or (b) notification of a remotely located medical expert. Scenarios are possible in which:
1) the abnormality which calls for notification is the same as that which call for treatment;
2) the abnormality which calls for notification is less severe than that which requires treatment;
3) the abnormality which calls for notification is more severe than that which requires treatment; and
4) the abnormality which calls for notification is different than that which requires treatment.

By way of example: In the case of 2) and 4) hereinabove, there may be abnormalities which, though not severe enough to always require treatment, might require treatment under certain circumstances which are apparent to an expert person or system. Thus, providing an ICD shock for VT with a rate of over 240 bpm would be likely to represent sound management much of the time, but the desirability of providing an ICD shock for VT at 140 bpm will depend on a variety of circumstances. Some of these may be easily programmed, such as the duration of the event VT. But others may not. If the ICD in the example was connected to multiple sensors, then a complex decision based on the patient's blood pressure, respiratory rate, and even recent medical history and/or response to antitachycardia pacing in the past might all be factors that would be advisably considered in making a shock/no shock decision. In the case of therapy decision making based on multiple sensors, it becomes impossible to simply say that on set of abnormalities is more severe than another, and "different" is the appropriate term. Thus a VT rate of 140 and a blood pressure of 80 systolic may or may not be considered more severe than a situation with VT at 240 and a blood pressure of 90. Clearly, as the number of different types of sensors increases, and treatment decisions must be based on the data from each of them, algorithms will be more difficult to design, and there will be decreasing likelihood that such algorithms can match the decision making ability of a medical expert, "ME" (person or computational system). The value of having the device "seek consultation" with a ME under these circumstances is clear. At times, the blending of information from multiple sensors may be best accomplished using mathematical techniques which are beyond the scope of a routinely implanted device. Ultimately, treatment decisions may be based on complex functions of multiple parameters and time. Note is made of the fact that these functions may not meet all of the formal mathematical criteria of a function, since input data may not be continuous in nature.

By way of yet another example: It may be desirable to notify and ME only in cases of extreme abnormality, and to omit such notification for routine treatments. In such a circumstance, 16 could be operative to treat non-severe abnormalities without notification and to notify a ME for very severe ones. It could be further operative to treat the severe ones unless, having been notified of a severe event, a ME chooses to override the decision of a MP. Thus a single episode of VT at 240 beats per minute might be treated with a shock without notification of an ME, but four episodes of the same VT over 15 minutes might warrant notification.

Device 16 may be a microprocessor, a group of microprocessors or other computational devices as is known in the art. When preset criteria for ME notification have been met, it signals a ME by sending notification signal 18 to first transmitting/receiving device. "first T/R" 20, which is transmitted to the ME. 20 may consist of a single unit which performs both transmitting and receiving functions, or separate units. The transmission methods are discussed hereinbelow. Along with the notification signal, the logic device will send medical data 32 for the ME to evaluate. The data may include (a) actual signals 15, (b) a processed form of 15, e.g. filtered, compressed, etc., (c) a further refined form of 15 [e.g. beat to beat measurements of cardiac RR intervals], and (d) still further refined forms of data [e.g. the information that 17 of the last 20 beats were at a rate greater than 200].

The ME has a variety of options upon receipt of this information, discussed hereinbelow. If the ME chooses to treat, a real time remote control signal 22 is received by 20 and sent to 16. The logic device is operative to pass two types of control signals to the medical treatment device which it controls, (a) remote signals 24 which initially originate with the ME, and (b) local signals 28 generated by the logic device, based on its analysis of 15.

The logic device may prioritize among ME control signals 22 and its own control signals in a variety of ways:

a) It may always give priority to ME control signals over its own internally generated control signals; In such a situation, following notification, only the loss of communication with the MP would result in local control (i.e. control of the
b) In the presence of ME control signals, it may not even generate its own control signals;
c) It may always provide therapy unless there is a specific signal 22 which inhibits its providing therapy;
d) It may provide therapy along with the ME in an "OR" logic fashion, such that either one may cause 16 to cause 26 to treat.

Memory device 17 is linked to the logic device. It may be used for the storage of information about patient events, the storage of programs for medical treatment device management and sensor signal processing, the temporary storage of information during a communication exchange with a ME, the storage of write-once-only information, and the storage of rules for notification management.

Figure 2A:
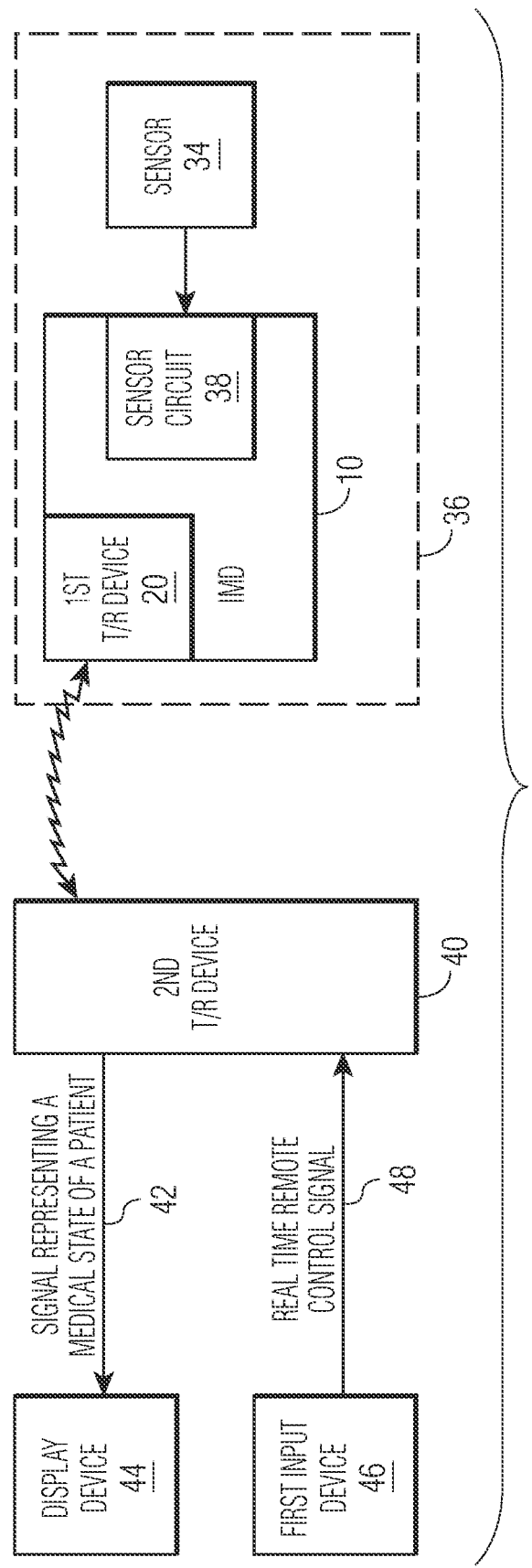
FIG. 2A is a representational block diagram of a system including an IMD, a sensor and a remote station to be operated by a human medical expert.

FIG. 2A shows an embodiment of the invention in which IMD 10 communicates through it first T/R, with a second T/R device 40. 40 provides signals representing a medical state of a patient 42 to be displayed on display device 44. First input device 46 allows an ME to send real time remote control signals to 40, for transmission to 20. 10 and at least one sensor 34 is implanted inside the body of a patient 36. Examples of possible sensors include a pacemaker wire (for sensing cardiac electrograms), a defibrillator lead, a transducer for measuring glucose concentration, a system of conductors for measuring transthoracic impedance, etc. In the embodiment of the invention shown in FIG. 2A, sensor information from 34 is coupled to the sensor circuit 38. IMD 10 transmits the information representing the sensor information (which may be the actual sensor information) via 20 to 40, for display by 44. A human ME may then determine the appropriate treatment, and input it to 46. Signals 48 representing the treatment are transmitted from 40 to 20, thereby to affect the function of 10.

Figure 2B:
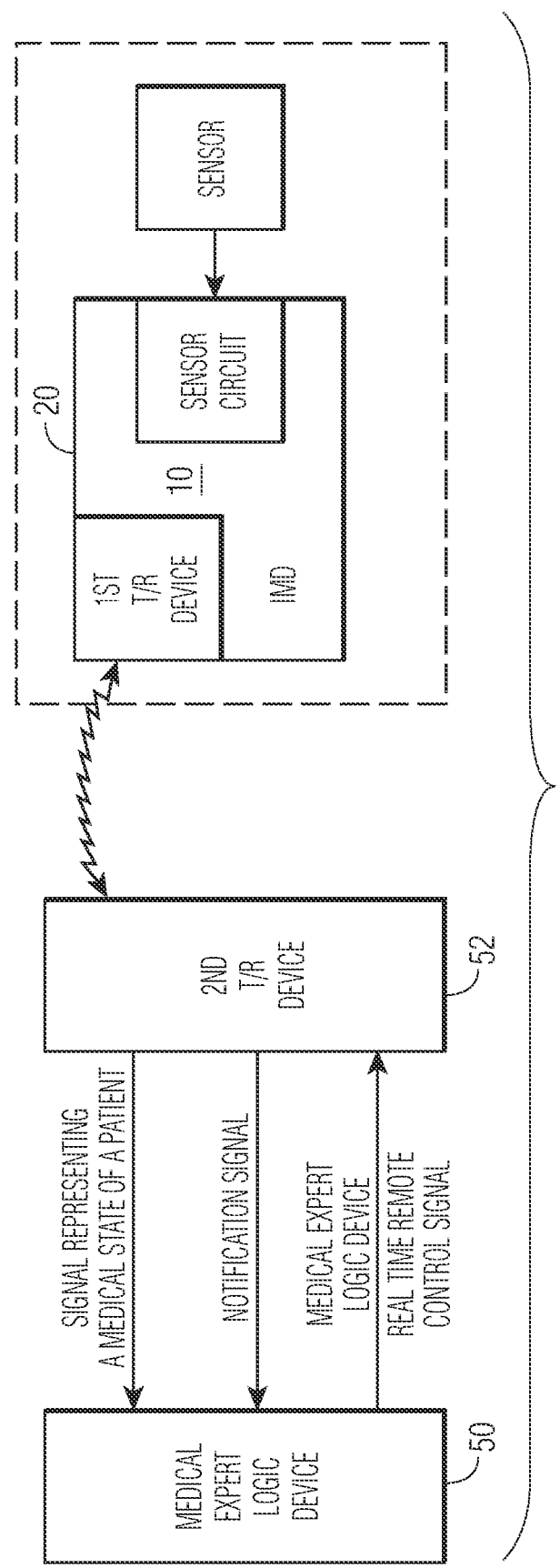
FIG. 2 B is a representational block diagram of a system including an IMD, a sensor and a remote station operated by a medical expert computational device.

FIG. 2B shows an embodiment of the invention in which the ME is a medical expert program or group of programs which run on a computational device 50. Each of the signals to and from the first T/R (18, 22 and 32 in FIG. 1) are transmitted between first T/R device 20 and the 2nd T/R of shown herein 52. A device such as 50 would have advantages over the logic device of the IMD including: (a) a much larger memory capacity, such that information may be stored concerning (i) other medical data from this patient; (ii) other medical data from other patients with a similar condition, (iii) performance data about IMD 10; (b) ability to update the database for 52 easily and frequently; and (c) ability to update the algorithms run by 50 easily and frequently.

Figure 2C:
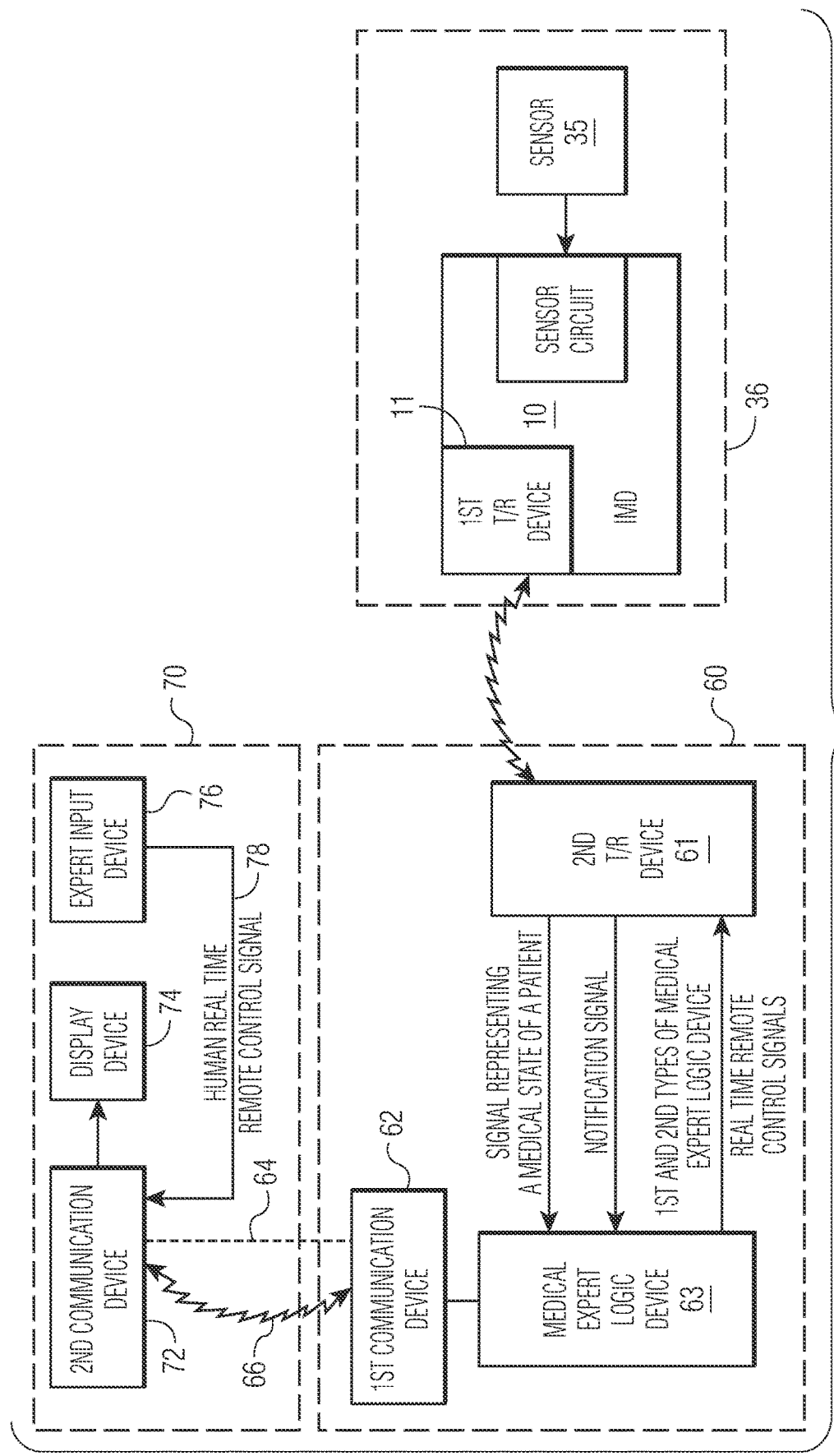

FIG. 2C shows an embodiment of the invention in which IMD 10 in patient 36 communicates with a computer ME 60, which in turn communicates with a human-based ME 70. First communication device 62 in 60 communicates with second communication device 72 in 70; the communication may be either wireless, indicated by signals 66 or wired, indicated by signals 64. The function of 74 is analogous to that of 44 in FIG. 2A, and the function of 76 is analogous to that of 46 in FIG. 2A. The route of the human real time remote control signal is from 76 to 72 to 62 to 63 to 61 to 11 to 10. In an alternate embodiment, the human control signal could be coupled from 62 directly to 61. In yet another embodiment, an RF signal from 72 could be sent directly to 11. The human ME may use each of the following in the process of making a decision: (a) signals (processed and unprocessed) from one or more sensors 35 in patient 36, (b) signals indicating the analysis by the logic device of IMD 10, and (c) signals indicating the analysis by expert logic device 63. There are numerous possible relationships which determine dominance, in terms of control, among each of (i) the human ME, (ii) device 63, and (iii) the IMD logic device. For example:

a) in one embodiment of the invention, human ME signals, if received by the logic device of IMD 10 take precedence over control signals which may have been generated by the IMD logic device and over control signals generated by the analysis of the medical data by 63;
b) in another embodiment, the human may be overruled if both 63 and the IMD logic device disagree with the human;
c) in another embodiment, an "OR" logic prevails, and any one of the IMD logic device, 63 or the human ME may cause therapy to be delivered;
d) in another embodiment, "AND" logic prevails, and therapy is delivered only if each of the human and 63 and the IMD logic device indicate that treatment is desirable; and
e) in another embodiment, any two of the three of the human ME, 63 and the IMD logic device will dominate.

To reliably maintain a system in which the control of an implanted medical device is shared or given over to an outside agent, all possible means to maintain communications integrity must be undertaken. Techniques for improving reliability include but are not limited to: (a) redundant communications, (b) the ability to change a route (e.g. wired vs. wireless [though at some point there must be a wireless segment for the implanted device), (c) the ability to change a communications mode (e.g. different means of signal encoding, as is known in the art), (d) the ability to change power output of an RF or other electromagnetic device, (e) the ability to change the sensitivity of a receiver, and (f) the ability to change frequency or channel or telephone number or internet provider.

Figure 3A:
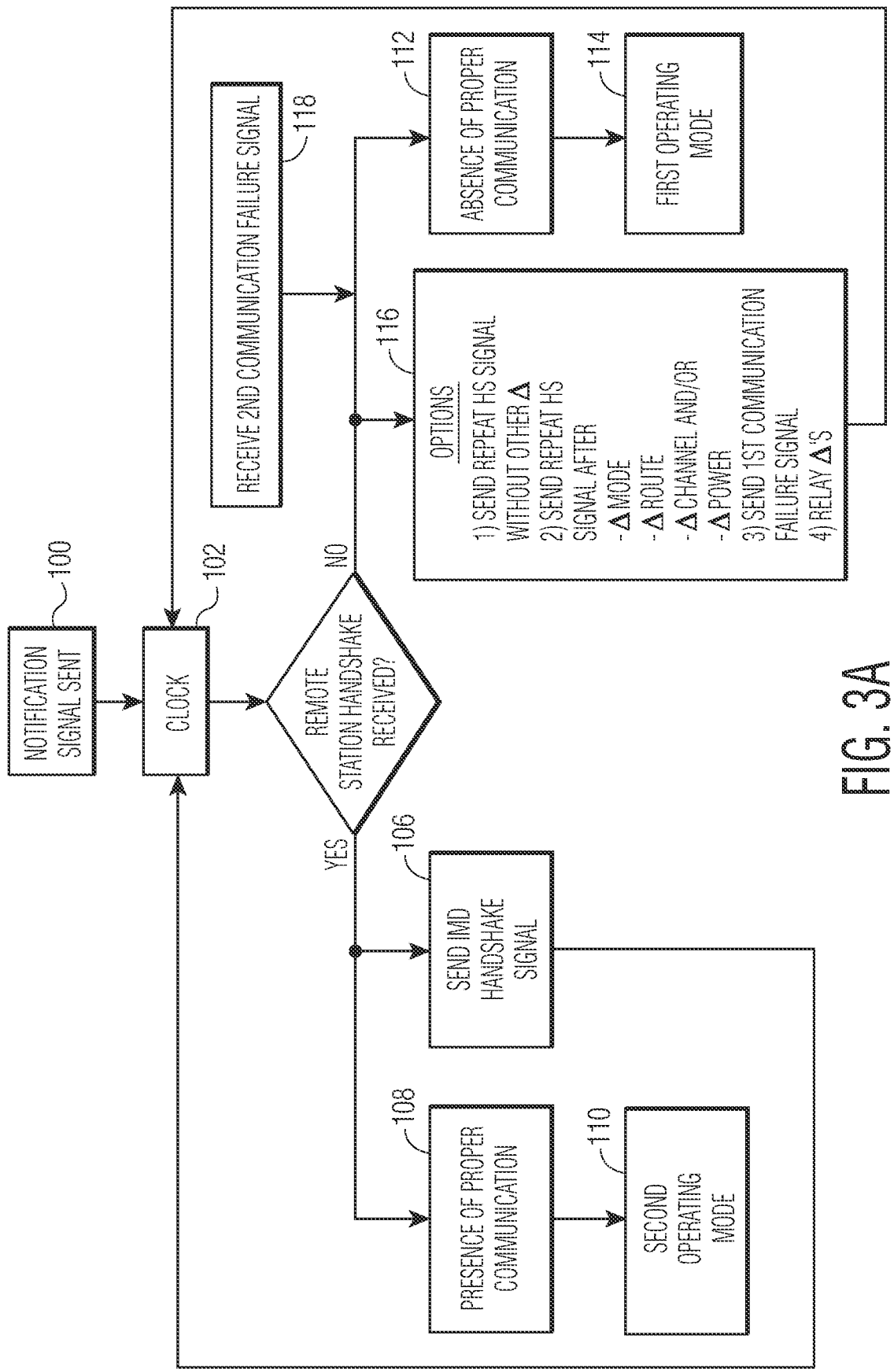
FIG. 3A is a flow diagram of a communication routine for a remotely controllable IMD.
Figure 3B:
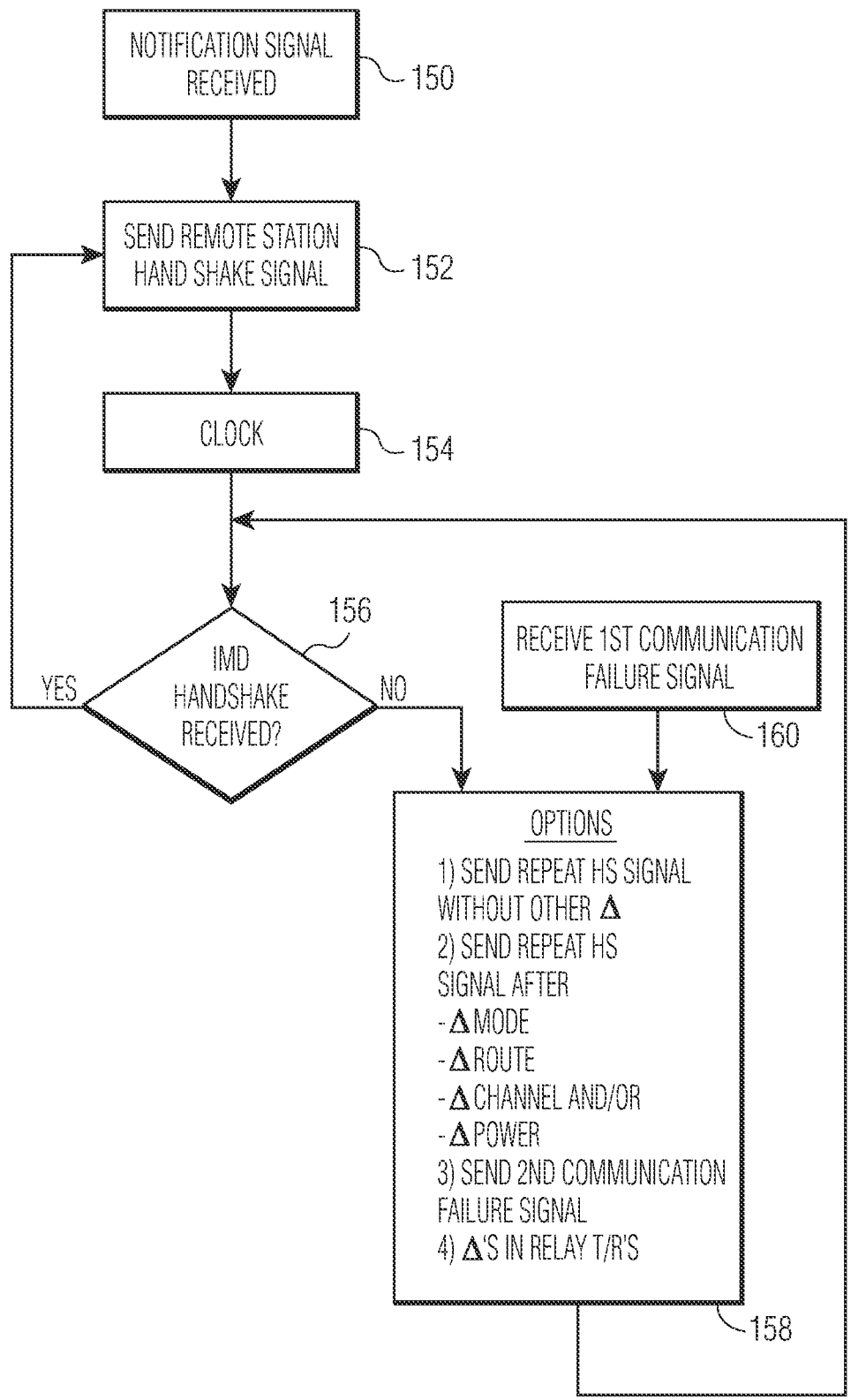
FIG. 3B is a flow diagram of a communication routine for a remote station which communicates with a remotely controllable IMD.

Furthermore, it is important that each of the communicating agents be able to determine whether each segment of the communication path (in each direction) is operative, on a real time basis. For example, if the IMD logic device determines that there has been a break in communication with the ME, it must immediately (a) revert to autonomous operation, and (b) take whatever corrective means it can to restore proper communication. Thus, one embodiment of the invention is operative to cause immediate restoration of device control by the IMD logic device, in the event of a break in communications. To accomplish this, a handshaking routine is operative. FIG. 3A shows the routine at the IMD, and FIG. 3B shows it at the remote station. (Hereinbelow, communication between the IMD and the remote station through one or more relay devices is described. Handshaking routines, known in the art, are possible between (a) each 'adjacent' communicating component in a string of devices, as well as (b) an overall handshake between the remote station and the IMD.

Referring to FIG. 3A, which shows one possible semi-continuous handshaking routine at the IMD, following the transmission of notification signal 100 by the IMD, an interval of time measured by clock 102 is allowed to elapse, waiting for a response, in the form of a remote station handshake signal. If the remote station handshake signal is received in a timely manner, block 104 leads to blocks 106 (resulting in the transmission of an IMD handshake signal by the IMD) and 108, a declaration of the presence of proper communications. The presence of proper communications allows for a second IMD operating mode, in which the IMD is controlled remotely. Block 106 leads to another waiting period determined by 102. In the presence of proper communications, the flow diagram will continuously cycle from 102 to 104 to 106 to 102 . . . . However, if there is an interruption in communications, such that a remote station handshake signal is either not received, or not received in a timely manner, block 104 leads to 112 and the declaration of the absence of proper communications. 112 leads to 114 and a first IMD operating mode. In the first operating mode, the IMD is controlled only by the IMD logic device. In this case, 104 also leads to 116, which lists a menu of options directed at restoring proper communication including: (a) repeat transmission of the remote station handshake signal without any other change; (b) change in either mode, route, power or channel/frequency, (c) change in the sensitivity, selectivity or other receiver characteristics of the IMD receiver (not listed in the figure), (d) change in the characteristics or choice of an upstream communications relay unit (see below), etc. Each of these choices then leads to another handshake attempt, and another waiting for a response.

It may be possible to determine whether a break in communication occurred in the IMD to remote station direction, or in the reverse direction by the sending and receiving "communication failure" signals. Thus if the IMD receives 118 a second communication failure signal, it implies that the remote station to IMD leg is intact, and it is the IMD to remote station leg that has failed. This helps direct remedial action. Among the items in menu 116 is the sending of a first communication failure signal, to allow the remote station to gain some diagnostic information about the source of the handshake interruption.

FIG. 3B shows one possible version of a handshaking routine at the remote station. Although the determination of a break in communication is far more important at the IMD end (i.e. so that the IMD may resume autonomous function immediately), there are remedial actions that can be accomplished at the remote station end, therefore making the detection of a handshake interruption valuable at that end as well. At block 150, the notification signal is received from the IMD, leading to the transmission of a remote station handshake signal at 152. If after a suitable delay measured by clock 154, there is no received IMD handshake, 156 leads to 158, with a menu of remedial options which are analogous to those in block 156. The intact handshake loop in the diagram is 156, 152, 154, 156 . . . . The broken handshake loop is 156, 158, 156, 158 . . . .

Many other approaches possible handshaking protocols and apparatus will be obvious to those skilled in the art.

Finally (see hereinbelow), downloading a treatment plan or routine for a currently happening ME-IMD session, for storage in the IMD memory, may allow for the completion of a ME set of treatment steps which were interrupted by a break in communications.

Many implanted devices have a low battery drain and a longevity measured in years. If the same battery that supplies a minimal amount of energy for device function (e.g. cardiac pacing, where the current drain may be 10-20 microamps or less) must also supply a transmitter, then unless there is judicious power management, there may be substantial shortening of device battery life. Among the options for accomplishing this are:

a) programming notification criteria so that the function is not over-used;

b) the placement of one or more relay units (see below) in proximity to the IMD/patient, so that transmission from the first T/R involves only short distances;

c) methods of powering down the first T/R, partially, during a transmission, if possible;

d) monitoring battery function so that as the battery ages, the criteria for notification may be made more restrictive;

e) letting the ME know the battery status during a transmission, so that the ME, recognizing an aging battery or batteries, may take action to shorten the current transmission and limit future ones, perhaps by either (i) remotely reprogramming notification criteria, or (ii) remotely programming transmitter power consumption;

f) having a dual power supply arrangement, where one power supply powers only the device T/R (or only the device transmitter), and one power supply powers everything else in the device. An alternate embodiment of this approach would be to the transmitter (or T/R) battery or batteries to be rechargeable.

Figure 4A:
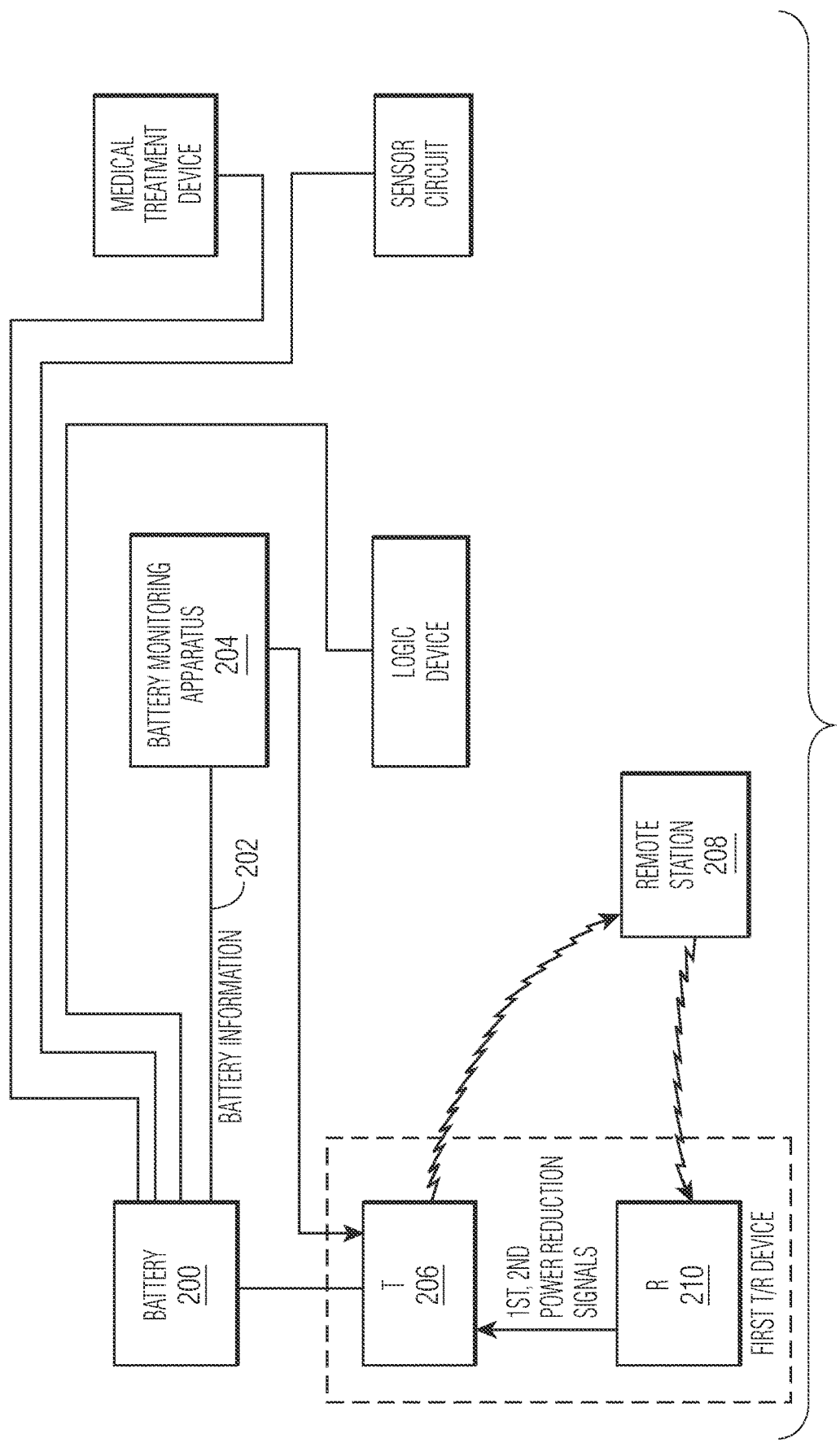
FIG. 4A is a representational block diagram showing remotely controlled power management for a remotely controllable IMD with one battery.

Four exemplary ways of handling battery management are illustrated by the embodiments of the invention shown in FIGS. 4A-4D. Hereinbelow, the word battery may refer to a single cell, two or more cells in series, two or more cells in parallel, and may refer to combinations of these. FIG. 4A contains a single battery 200 which supplies each of the components of the 1 MB. In addition to supplying the components discussed hereinabove in conjunction with FIG. 1, the battery also supplies battery monitoring apparatus 202 with energy. 202 monitors one or more of battery voltage, cell impedance, battery current drain, the droop in cell voltage with increased demand, and indirect measures of battery function (e.g. the charge time of an ICD). The battery information is supplied to the IMD transmitter 206, for transmission to remote station 208, for assessment by the ME. The ME may use the information for management of real-time power consumption (i.e. reduce transmitter power during the current encounter) by sending a signal to receiver 210, which passes the information contained therein to transmitter 206. Alternatively, the MP may reprogram device performance (e.g. notification criteria), by sending a programming command from 208 to 210 to the logic device (which coupling is not shown in FIG. 4A, but is indicated in FIG. 1.

Figure 4B:
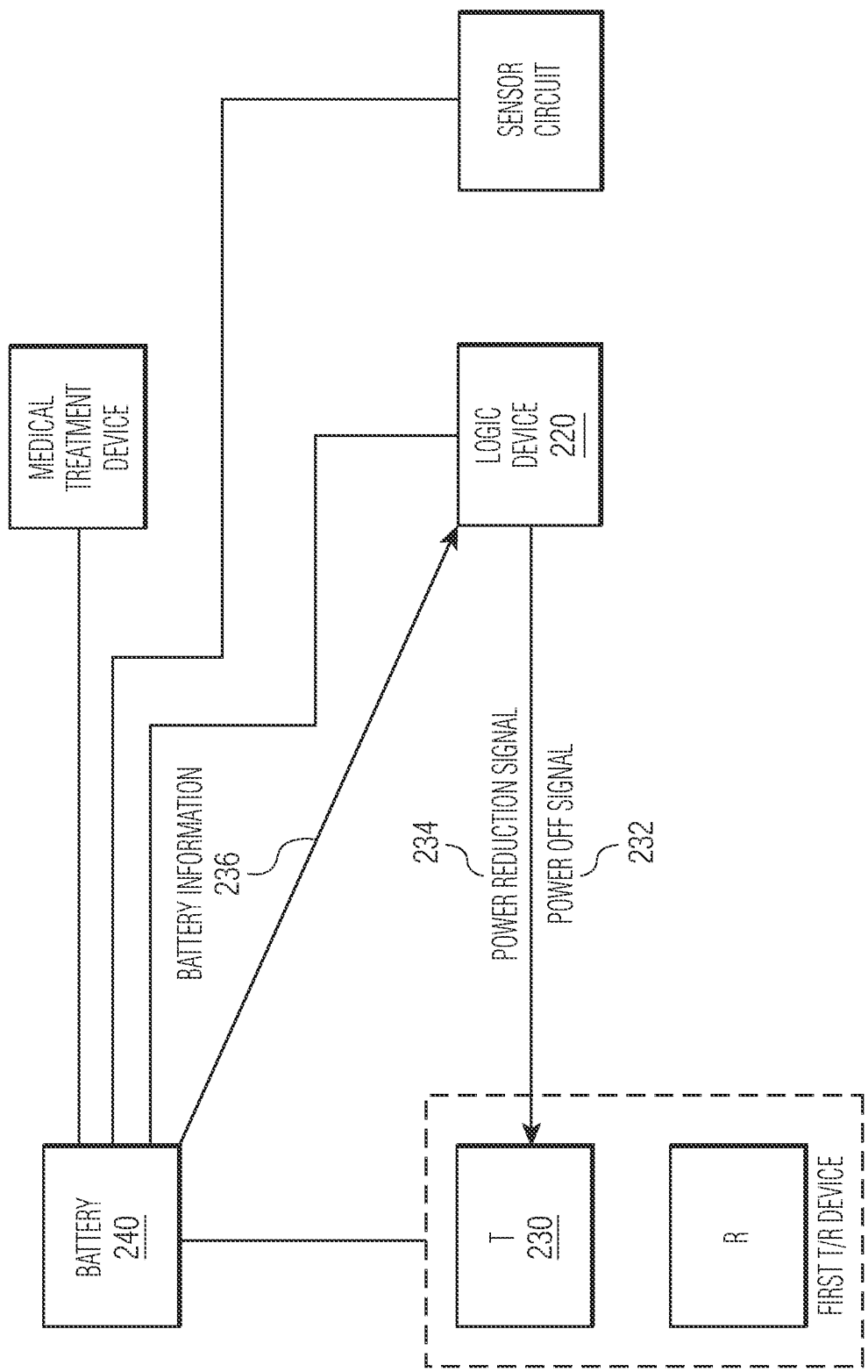
FIG. 4B is a representational block diagram showing locally controlled power management for a remotely controllable IMD with one battery.

FIG. 4B shows a one battery management approach where management is directed within the IMD, i.e. by the IMD logic device. Information 236 about battery 240 (similar to the information discussed hereinabove in conjunction with FIG. 4A) is processed by logic device 220, and may be used maximize the longevity of the battery, as discussed hereinabove. Besides power reduction signals 234 which reduce transmitter 230 power by a variety of possible values, a signal 232 may be sent to power 230 off. As indicated, 220 may also reprogram itself to accomplish such goals as altered notification criterion.

It is possible to combine the attributes of the power conservation approach shown in each of FIGS. 4A and 4B.

Figure 4C:
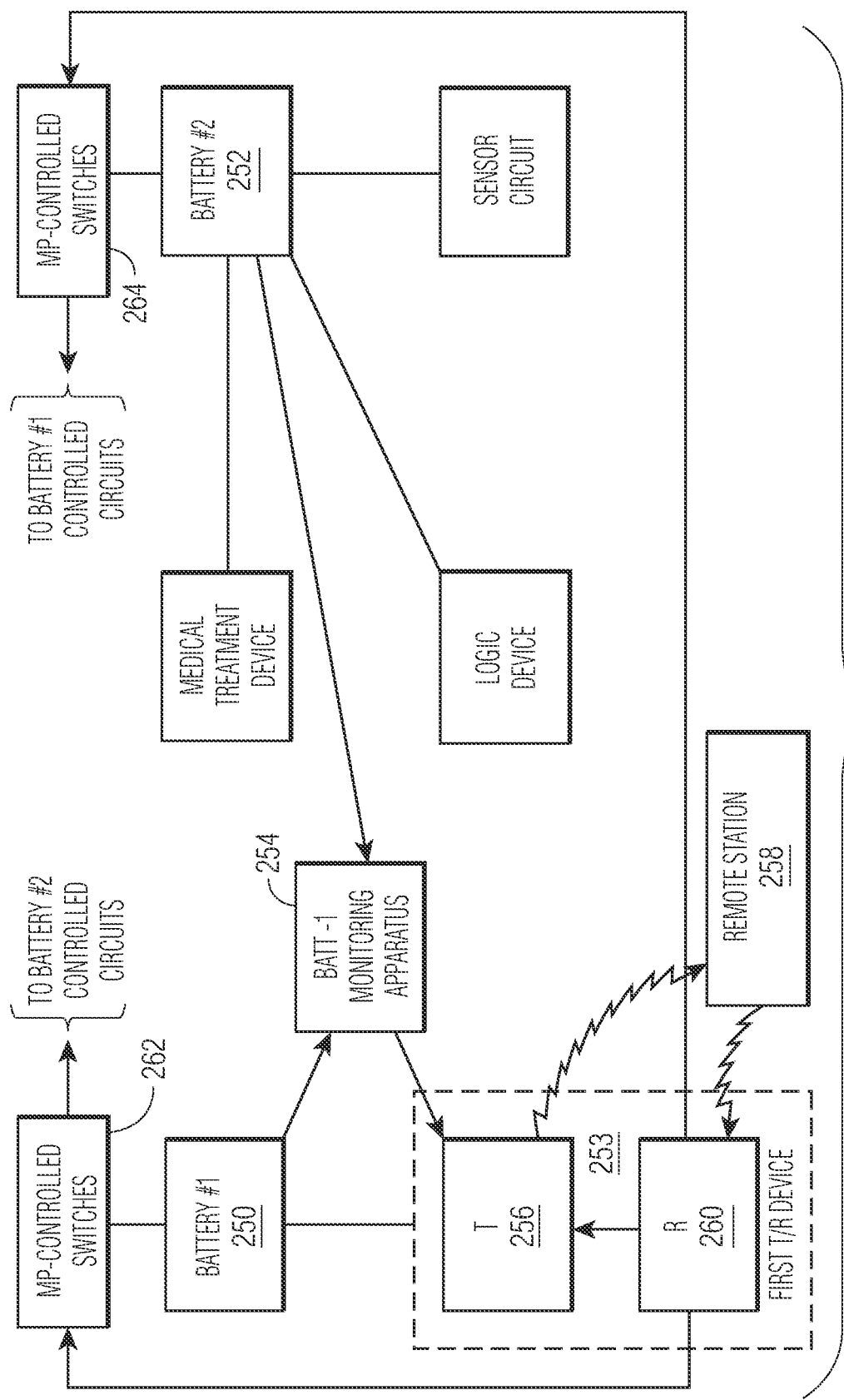
FIG. 4C is a representational block diagram showing remotely controlled power management for a remotely controllable IMD with two batteries.

FIG. 4C shows a dual power supply approach to power management. As shown in the figure, battery 252 powers the device components except for the device T/R 253 (and perhaps the battery monitoring apparatus 254), which are powered by battery 250. Battery information moves from 254 to transmitter 256 to remote station 258 for evaluation by the ME. The ME may control transmitter characteristics by sending a signal from 258 to receiver 260 to transmitter 256. In addition, the presence of a second battery gives the ME some additional options: the use of one of the batteries to perform the function of the other. Thus if battery 252, which controls the IMD in general, is nearing its end of service, and transmitter battery 250 has a substantial remaining energy supply, the ME may cause switching apparatus 262 to divert some or all of 250 energy to perform the functions intended for battery 252 (i.e. non-transmitter function). Similarly, the MP may do the mirror image diversion: In a situation with good 252 energy supply, poor 250 energy supply and the need for an urgent interaction with a ME, switching apparatus 264 may divert energy to transmitter 256 that might otherwise not have been able to be supplied by 250. The ME could learn about the status of battery 252 by information passed along the link from it to 254, and thence to 256 and 258.

Figure 4D:
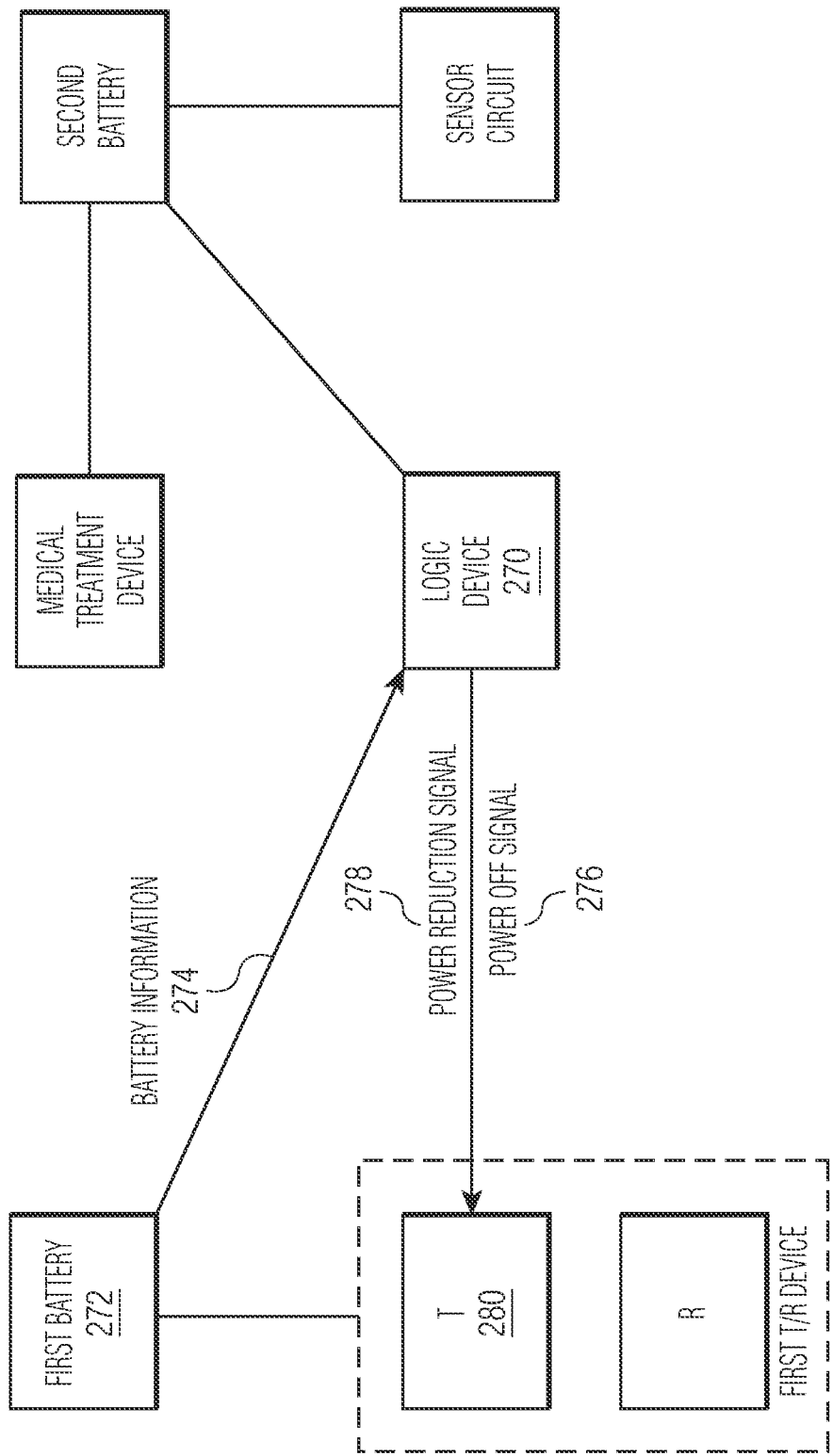
FIG. 4D is a representational block diagram showing locally controlled power management for a remotely controllable IMD with two batteries.

FIG. 4D shows a 2 battery configuration, with energy management by the IMD logic device. All of the functions performed by the apparatus in FIG. 4C could be performed by that in FIG. 4D, except that the source of management commands is logic device 270. 270 processes information 274 about the status and projected longevity of 272, and may use it to either (i) make one or more reductions 278 in the power consumption of 280, or (ii) turn off 276 the transmitter.

Figure 5A:
FIGS. 5A and 5 B each show a graphic representation of some possible arithmetic relationships illustrating the notification definition and the parameter abnormality definition.
Figure 5B:
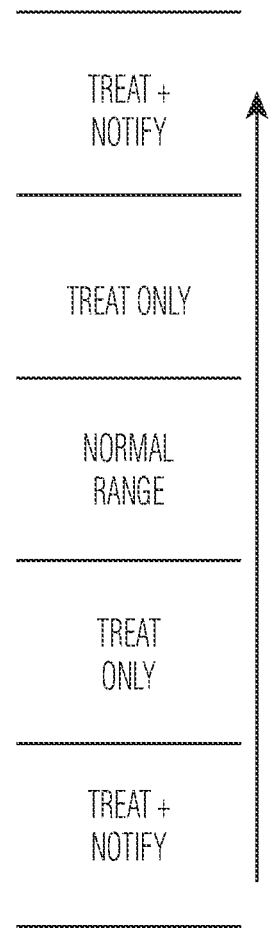

A wide variety of possible triggers for ME notification are possible. FIGS. 5A and 5B illustrate a situation in which a single parameter (e.g. heart rate) is monitored to determine device action. Conventional ICDs (which include pacemaker function) are programmed to treat tachycardias which are above a certain heart rate, and bradyarrhythmias whose rate is below a certain heart rate. The scenario illustrated by FIG. 5A shows a scenario in which a range of rates which is intermediate between the high rate, at which treatment is definitely required, and the normal rate, may be defined as the notification range of rates. For example, an ICD might be programmed to:

a) notify for rates from 140 to 160 bpm and to treat and notify for rates above 160 bpm. The ME, upon notification, would decide whether treatment is required for a rate of say, 150 bpm, and if so, cause the ICD to provide such treatment. The ME might decide (a) to try some gentle treatment such as a non-aggressive antitachycardia pacing for the situation, (b) to go ahead and provide aggressive treatment, or (c) to not treat at all. In the latter case, the ME might decide to check the patient at some later time, e.g. by leaving an instruction in the ICD for the ICD to check in with the ME in 30 minutes. The ME might further program altered "second notification" criteria, i.e. if the rhythm normalizes, then over the next 24 hours, the threshold for notification is lower (e.g. 130 bpm).

b) notify for rates from 140 to 160 bpm and to treat (and not notify) for rates above 160 bpm. [This is not shown in the figure.] This saves battery in cases where there is little or no uncertainty about which therapy is the appropriate one.

In the figure, a similar format is programmed for bradyarrhythmia. For example, the pacing circuits may treat when the rate declines to 40 bpm, but may be programmed to notify for rates in the range of 40 to 50 bpm. Alternatively, the programming person might choose not to notify for pacing at 40 bpm (i.e. treat without notification).

FIG. 5B shows a format in which the ME is notified (and treatment is given) for values of a parameter that are extreme but not for values that are only moderately abnormal. For example, the ME might be notified for tachycardia that was treated whose rate was 260 bpm, but not for tachycardia which were treated with rate less than 200 bpm.

The aforementioned scenarios reflected by FIGS. 5A and 5B concern rather simply notification criteria. More complex ones may depend on the results of multiple different parameters from multiple sensors, and their evolution over time. Still more complex scenarios may depend not just on the measured values of these parameters, but complex mathematical functions of them.

Figure 6A:
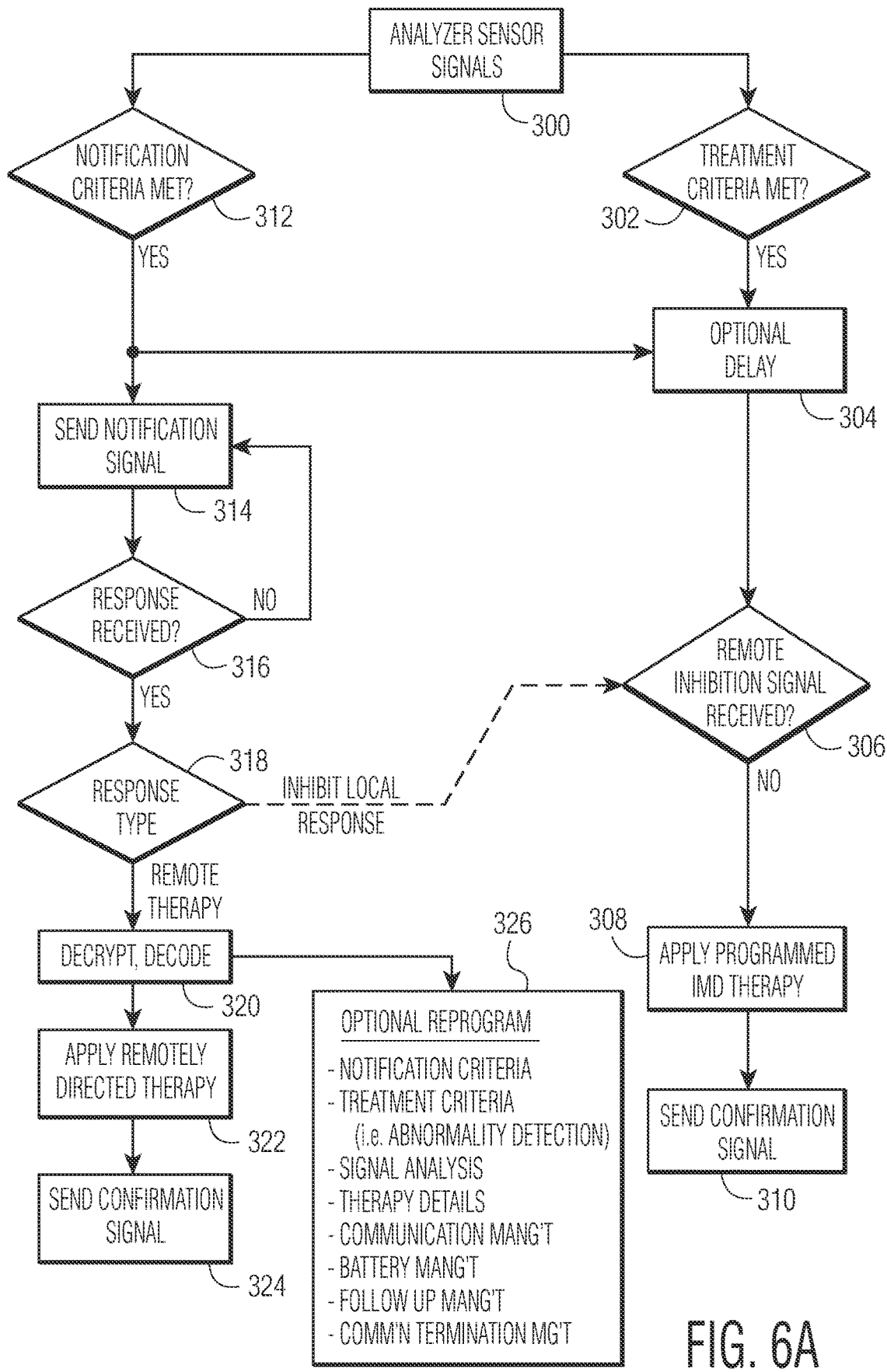
FIG. 6A shows a flow diagram of one possible algorithm for notification.

Once notification has occurred, the other dimension of interaction between the IMD and the ME, is how much control the ME has access to, following notification. FIG. 6A shows a scenario in which the ME is given essentially complete control. The right hand side of the figure shows the essential features of operation when the device operates autonomously. Following detection of a parameter value 302 which requires therapy, the device applies the pre-programmed therapy 308, and optionally transmits a confirmation signal, block 310, indicating that therapy has been provided. However, if notification criteria have been met, 312, the IMD sends a notification signal, 314, for receipt by a remote station, and awaits a response, 316. Once the ME is in communication with the IMD, the ME may both positively and negatively control the device; That is, the MEP may choose to inhibit (block 318 to 306) an action that the device, if operating autonomously, would have performed. Alternatively the ME may choose to cause the device to deliver therapy, even though the IMD program may not have called for this. In such a circumstance, block 318 leads to 320, in which an ME command is decrypted and decoded, and then to 322, in which the therapy instructions are carried out, followed by the sending of confirmation signal 324.

Since the establishment of a communication link between the ME and the IMD may take a short time, an optional delay 304 is added in before the IMD acts autonomously, in a situation when notification has occurred. This is indicated by block 312 inducing optional delay 304, to prevent autonomous IMD therapy before the ME can be involved.

The ME has a number of options for influencing the management of future events post notification, shown in block 326. In a preferred embodiment of the invention, the ME may reprogram (a) notification criteria, (b) the definition of what constitutes and abnormality, in terms of autonomous device functioning, (c) aspects of sensor signal analysis, (d) the details of therapy during autonomous device functioning, (e) communication management [route, mode, channel, etc.], (f) battery management, (f) followup management (the ability of the ME to ask for a callback from the IMD) after a ME-managed-event, to report patient status), and (g)

communication termination management (e.g. how long until communication ends after [i] a successfully managed event, and [ii] an event in which communication failed during the event).

Figure 6B:
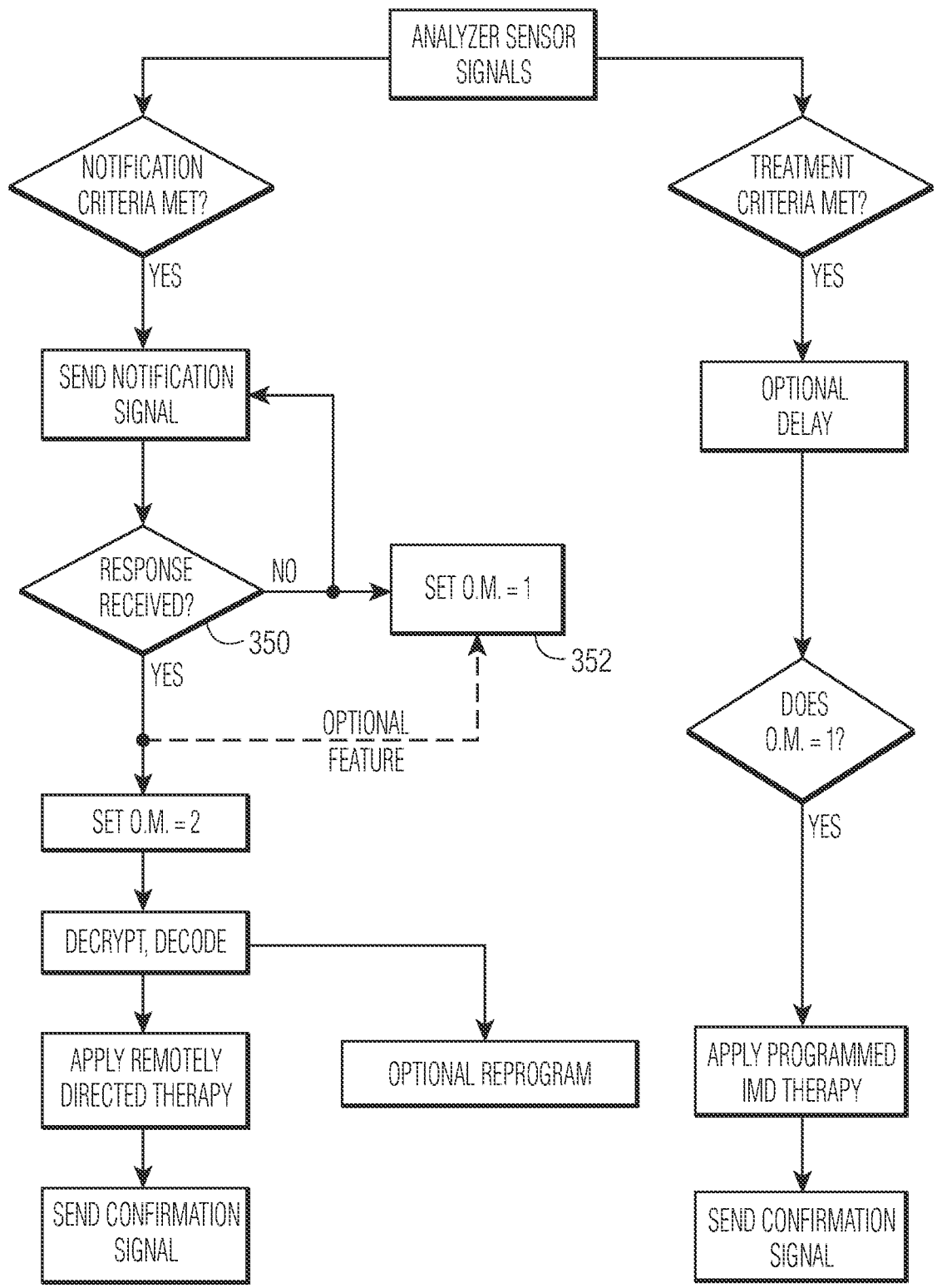
FIG. 6B shows another flow diagram of one possible algorithm for notification.

FIG. 6B shows another management scenario. Two operating modes are defined for the IMD. In a first operating mode (O.M.=1, in the figure) the IMD logic device is in control of therapy, while in a second operating mode (O.M.=2, in the figure), the ME is in control. The scenario shown in 6A involved moment to moment choices by the ME of whether to inhibit an IMD function; In the scenario in 6B, all IMD function is inhibited in the second operating mode, unless (a) the ME chooses to return the control to the IMD (block 350 to 352 via broken line indicating optional feature), or (b) communication fails [350 to 352 via solid arrow]. In other aspects not explicitly mentioned, the algorithm in FIG. 6B is identical to that of 6A.

Figure 6C:
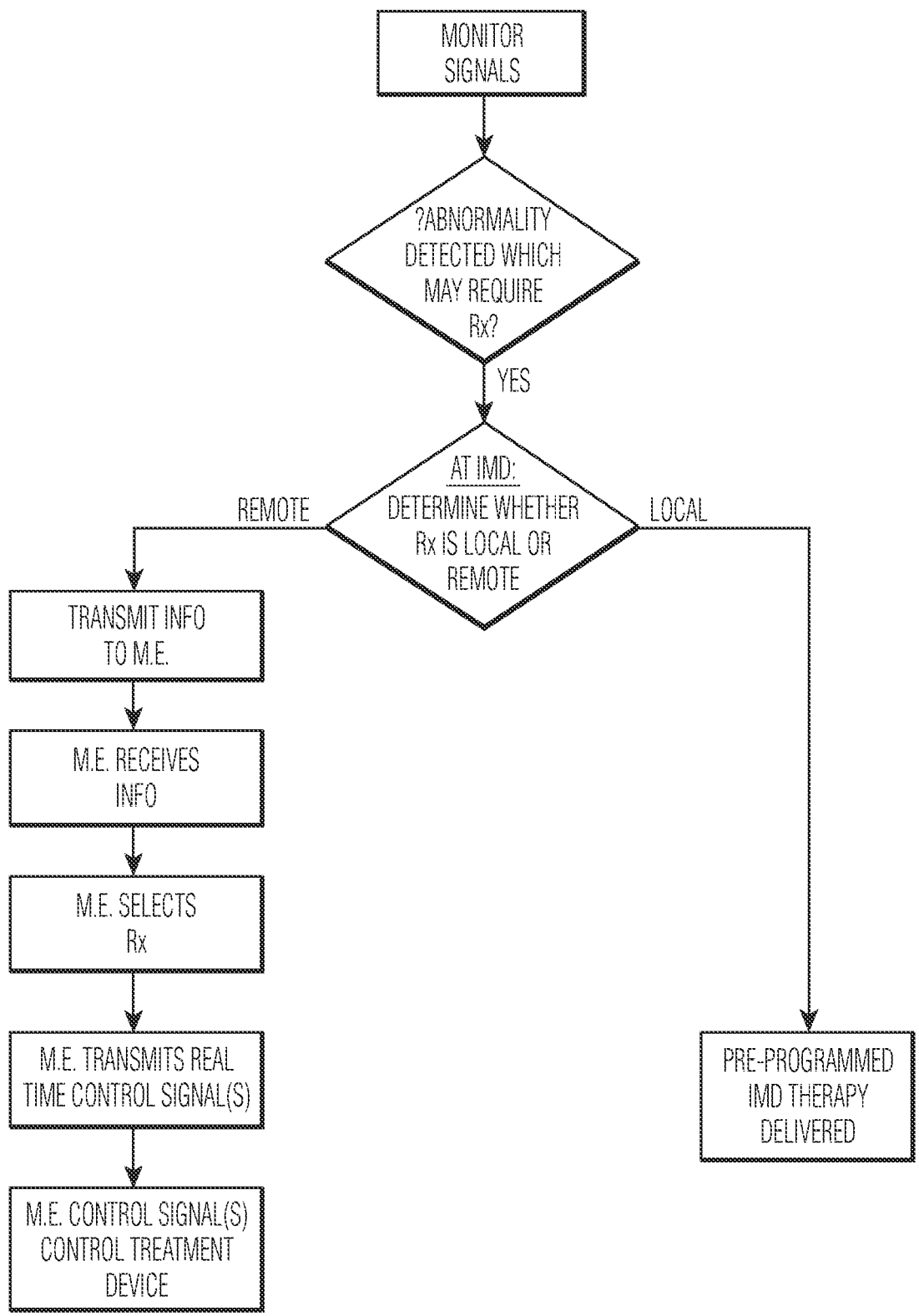
FIG. 6C shows another flow diagram of one possible algorithm for notification.

FIG. 6C shows a different algorithm. In this case, the decision between remote and local management is made (a) early on [i.e. before the ME is involved], and is made by the logic device of the 1 MB. Other aspects of the figure not specifically discussed are similar to those in already discussed figures.

Figure 6D:
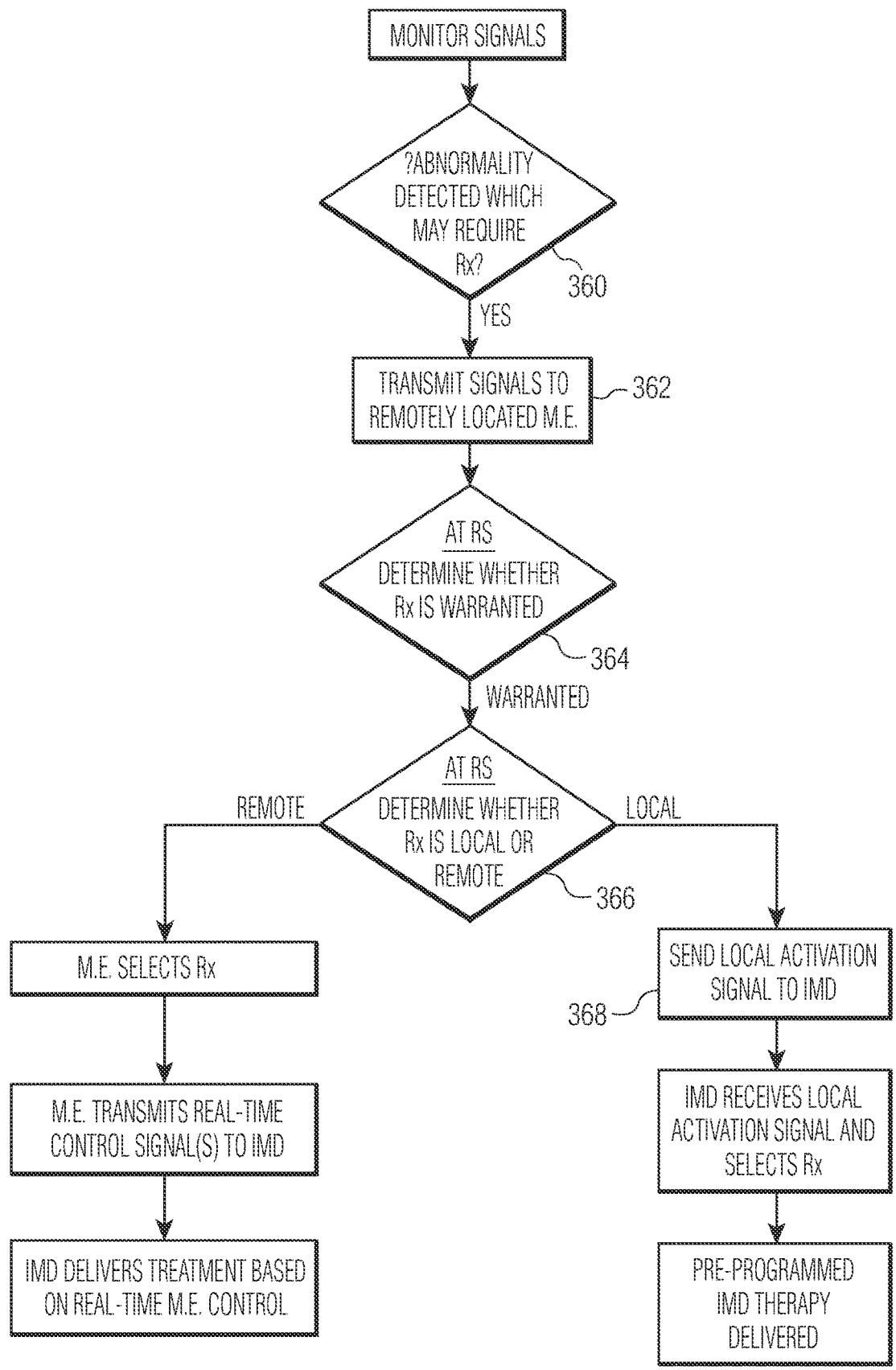
FIG. 6D shows another flow diagram of one possible algorithm for notification.

FIG. 6D shows another algorithm in which the remote station (RS) is given a particularly high level of priority. If an abnormality is detected by the IMD which may require treatment 360, signals are transmitted to the ME 362, at which point, two determinations are made: (a) Is therapy warranted [block 364]? and (b) Is the source of therapy-related choices to be local (i.e. the IMD) or remote (i.e. the ME)[block 366]? If the source of therapy is to be local, the ME returns control to the 1 MB. Other aspects of the figure not specifically discussed are similar to those in already discussed figures.

Other scenarios in which the ME does not have top priority have been discussed hereinabove.

Figure 7:
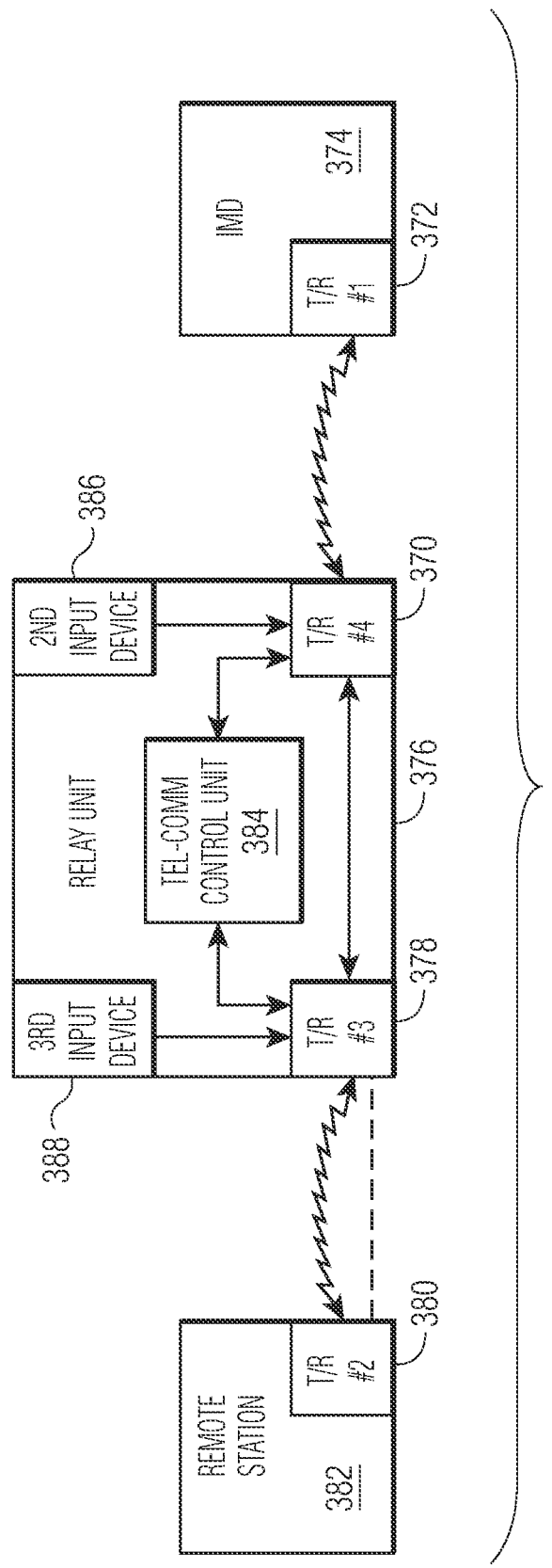
FIG. 7 shows a representational block diagram of a communications relay and its links to an IMD and a remote station FIG. 8 show an overview of one approach to ICD management.

Since battery conservation is a major concern with IMDs, and since wireless communication is a feature, the most efficient way to manage such devices is to provide one or more relay units between the IMD and the ME. Having one such unit in close proximity to the IMD will help to limit IMD battery depletion. Many possible relay units may be designed, and are known in the art. The essential features of such a unit are shown in FIG. 7. A fourth transmitting and receiving device, "fourth T/R" 370 communicates wirelessly with the first T/R 372 of the IMD 374. 370 is linked within relay unit 376 to a third T/R 378. The communication of the third T/R with the remote station 382 is via the second T/R 380. The communication between 378 and 380 may be wired (broken line) or wireless. It may involve no intervening communication device, or a number of such devices. It may involve a public telephone carrier or a private network, and may involve the Internet.

376 contains telecommunications control unit 384, which may adjust the operating characteristics of the third T/R to optimize communication with the remote station, and adjust the operating characteristics of the fourth T/R to optimize communication with the IMD. An optional second input device 386 could allow a local person or the patient to have some or complete control of the IMD; An optional third input device 388 could allow a local person or the patient to send a signal (e.g. a notification signal) to the ME. This could be used in a case where the patient feels that observation and potential ME intervention is warranted.

The following description details a preferred embodiment of the invention, entailing an ICD as the IMD. "MP" refers to a medical professional, which is the human version of the aforementioned ME.

Hereinabove and hereinbelow, ICD is intended to include:
A) devices which can administer a defibrillation shock; and
B) devices which can administer a defibrillation shock and can administer cardiac pacing. It is to be understood that this technology may be used in any implantable medical device, and any remotely controlled critical system.

Features of the Invention

1) The Implantable Cardioverter Defibrillator ("ICD") may initiate the communication between itself and the Central Station ("CS.") Mechanisms for this are illustrated.
2) The "control unit" referred to in Ser. No. 10/460,458 may be:
    A) a cellular telephone or other personal communication devices (such as a Blackberry®) as are known in the art.
    B) the Stationary Unit referred to in Ser. No. 10/460,458; and
    C) any relay unit whose purpose is to amplify the signal as it is passed along between ICD to CS.
Hereinbelow, the unit which serves as the communications hardware link between the CS and the ICD shall be referred to as the repeater unit ("RU").
3) Means within the ICD may select alternate mode of communication (e.g. a public or private telephone network, or the internet) and may select alternate routes of communication (e.g. in a multi-segment communication, selecting each segment of the total communications link.
4) Handshake signals may be exchanged between:
    A) the CS and the RU;
    B) the RU and the ICD; and
    C) the CS and the ICD.
The handshake signals may be used to indicate the presence or absence of communication signals between two components (e.g. the ICD and the RU) or to indicate the quality of the signals.
5) If the handshake signals indicate either an absent communications link or a poor quality one, the handshake signals may be used to cause the ICD to:
    A) select an alternate mode of communications;
    B) select an alternate route of communications;
    C) increase the power output of the ICD transmitter;
    D) increase the sensitivity of the ICD receiver.
6) The communications route from the ICD to the CS may involve multiple segments. These segments may include:
    A) an ICD to RU segment;
    B) one or more RU to RU segments;
    C) a RU to CS segment; and/or
    D) a direct ICD to CS segment.
7) Ser. No. 10/460,458 presents two formats for ICD control by a remotely located medical professional ("MP"):
Format A) In one (claim 219 and the 24 dependent claims which follow), the MP has primary control, and, in the absence of proper communication between the ICD and the MP, the ICD is in control;

Format B) In the other (claim 244 and the 25 dependent claims which follow), the ICD has primary control. The MP may overrule the ICD on a therapy decision, if he deems this to be desirable.

Feature 7 presents an approach in which the choice between Format A and Format B may be:
A) "hardwired" into the ICD;
B) irreversibly programmable (using a PROM, EPROM, EEPROM, etc., as is known in the art)
C) programmable by the medical professional who is responsible for programming the patient's ICD an a routine basis;
D) programmable by the MP, at the time of a medical emergency which has caused the ICD to communicate with the MP; and/or
E) programmable by the ICD, at the time of a medical emergency which has caused the ICD to communicate with the MP.

8) When the ICD initiates a communication with the CS, there may be a 2-or-more tier format such that:
A) 2 or more levels of emergency are defined;
B) for each level, a greater degree of "communications aggressiveness" (on the part of the ICD) is defined.

For example:
2 levels of emergency:
Moderate emergencies include ventricular tachycardia ("VT") at rates less than 160;
Major emergencies include a) VTs at rates greater than or equal to 160 and b) VTs or ventricular fibrillation ("VF") requiring a shock.

The corresponding two levels of communication aggressiveness would be:
For Moderate emergencies: a) no ICD transmitter output power boost (see below); and b) a small number of repeat attempts by the ICD to contact the CS; and
For Major Emergencies: a) one or more ICD transmitter output power boosts; and b) a large number of repeat attempts by the ICD to contact the CS.

Examples with 3 or more levels are obvious.

There is also the possibility of moderate emergencies (or the lowest level of emergency in a three or more level setup) resulting in no attempt at communication by the ICD.

9) Referring to 8) above, the definition of each level of emergency may be:
A) "hardwired" into the ICD;
B) irreversibly programmable (using a PROM, EPROM, EEPROM, etc., as is known in the art)
C) programmable by the medical professional who is responsible for programming the patient's ICD an a routine basis;
D) programmable by the MP (after communication between the MP and the ICD has been established), at the time of a medical emergency which has caused the ICD to communicate with the MP; and/or
E) programmable by the ICD (after the event which calls for a communication between MP and ICD); and/or
F) programmable by the ICD (during the event which calls for a communication between MP and ICD), if ICD circuitry determines that battery conservation requirements dictate a shut-down of the communication link.

10) Options based on battery reserve of ICD:
If hardware/software within the ICD determines that the ICD battery reserve is low, ICD options include:
A) terminate the communication;
B) send a message to the MP indicating the low reserve, and then terminate the communication;
C) lower power output and attempt to continue the communication; (This step may be repeated one or more times); and/or
D) continue the communication with output as is, and repeat assessment at a future time.

11) End of communication options:
The communication may end:
A) because of low ICD battery reserve, see Feature 10), above;
B) because the MP determines that further communication is not warranted; and/or
C) because the ICD logic unit determines that further communication is not warranted.

12) Identification-related issues:
Privacy in the communication between the ICD and the MP to be maintained:
A) Encryption and decryption per means and methods:
i) in Ser. No. 10/460,458; and
ii) others, known in the art;
B) An identification system wherein any ICD requires proof of MP identification, before and during and communication session.

13) The download of contingency plans from MP to the ICD, as soon as possible after the exchange of information begins. The purpose of the contingency plan download is to have a management strategy in place within the ICD, should the ICD-MP communication get interrupted midway through the event. Although the basic system calls for the ICD to revert to its programmed behavior in the event of communications interruption, the MP may desire to leave a temporary plan in place, to be used for the remainder of the current medical event. The MP may update the contingency plan as needed, as the medical event progresses.

An example of such a contingency plan would be more aggressive (or less aggressive anti-tachycardia pacing, prior to defibrillator shock). Another example would be to eliminate all intermediate energy shocks, and deliver only high energy shocks. Numerous other examples will be apparent to those skilled in the art.

Figure 8:
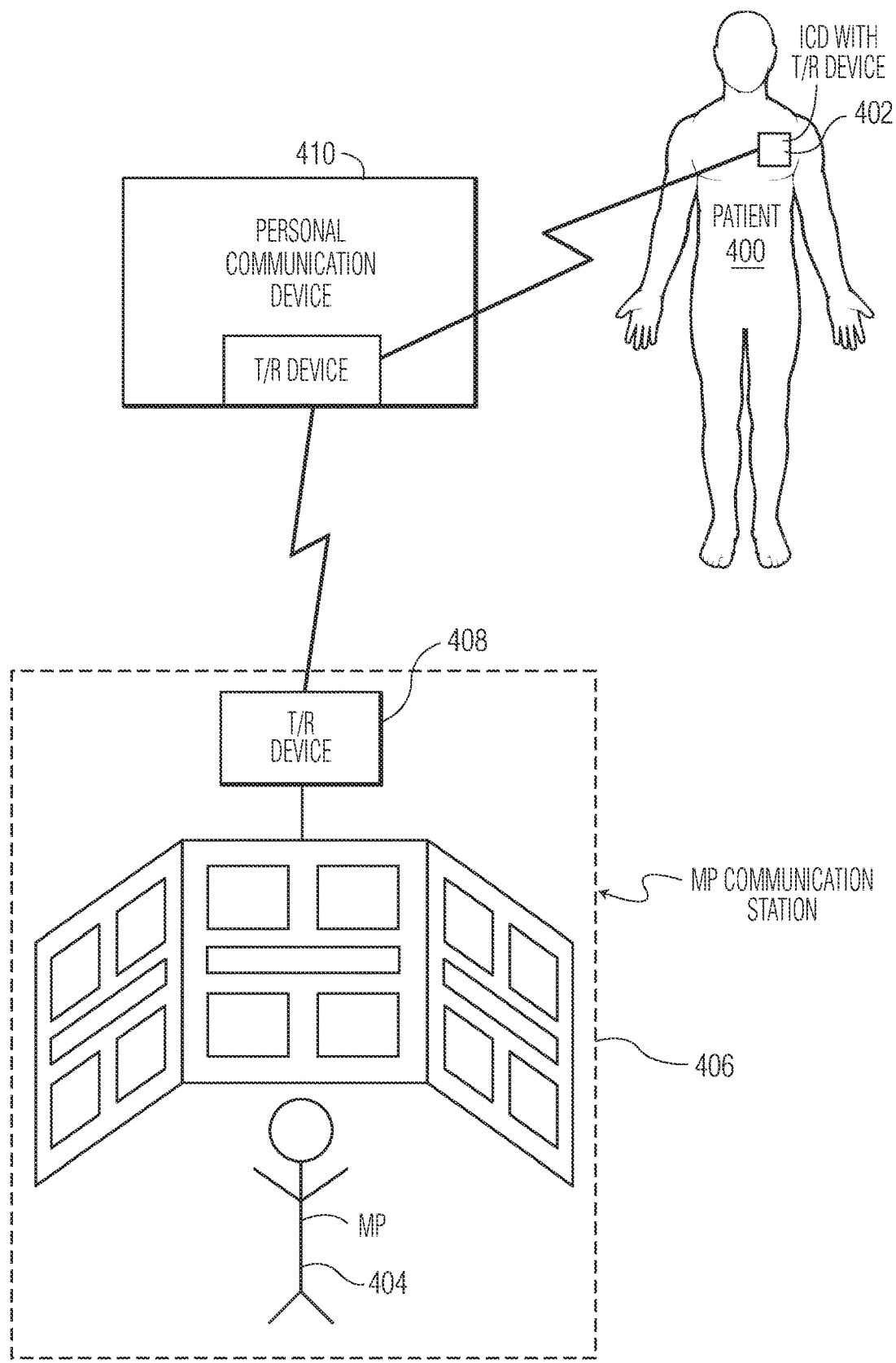

Referring to the figures, which show additional documentation of the means and methods of accomplishing the above 13 features:

FIG. 8 shows a patient 400 with and ICD 402 which communicates with a MP 404 at a MP communication station 406. 406 may be a central station as described in Ser. No. 10/460,458 or a central or peripheral station as described in Ser. No. 11/502,484. The ICD antenna is not shown, but in FIGS. 8-10, it is to be understood that the ICD has one or more antenna which allows it to properly communicate.

The communication route is in either direction between:
A) the T/R device within the ICD; B) the T/R device within personal communication device 410; and C) the T/R device within the MP communication station.

The communication route may also be directly between the T/R device within the MP communication station and the T/R device within the ICD.

Figure 9:
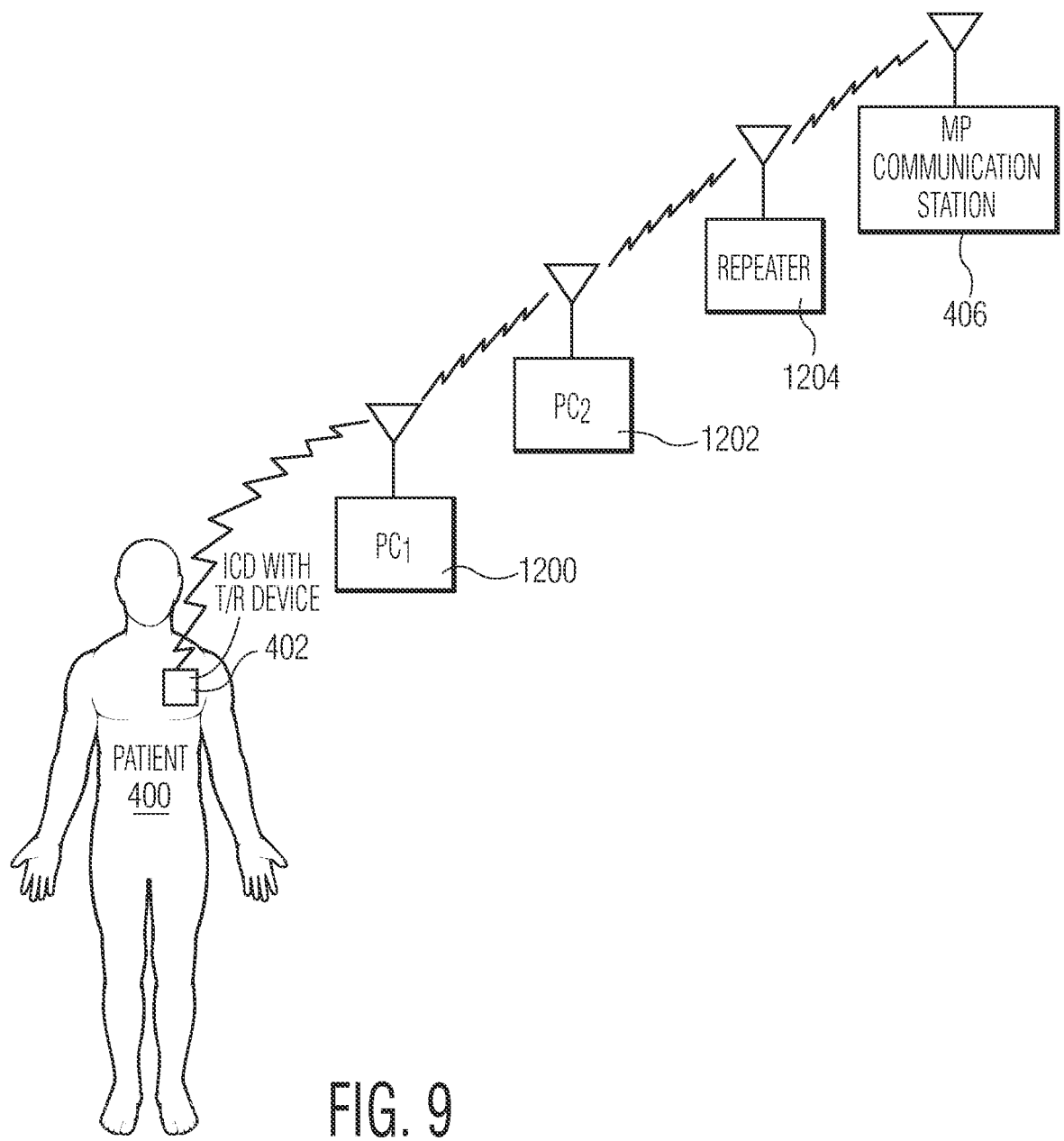
FIG. 9 shows a representational diagram of communication with multiple relays.

Referring to FIG. 9: It is also possible to have two or more intermediate communication links between the ICD T/R and the T/R of the MP communication station. In FIG. 9, there are 2 personal communication devices 1200 and 1202 and a repeater unit 1204 (as discussed above). Possible arrangements include:

A) two or more personal communication devices and no repeater units; B) one or more repeater units and no personal communication devices; and C) one or more repeater units and one or more personal communication devices.

It is also possible that the communications route would change during a single medical event. This would occur if either the MP or the hardware/software within the ICD determines that a change of route is desirable.

The antenna shown for 406 may, at times, not be used, since at times, communication with 406 may be via "land line."

Figure 10:
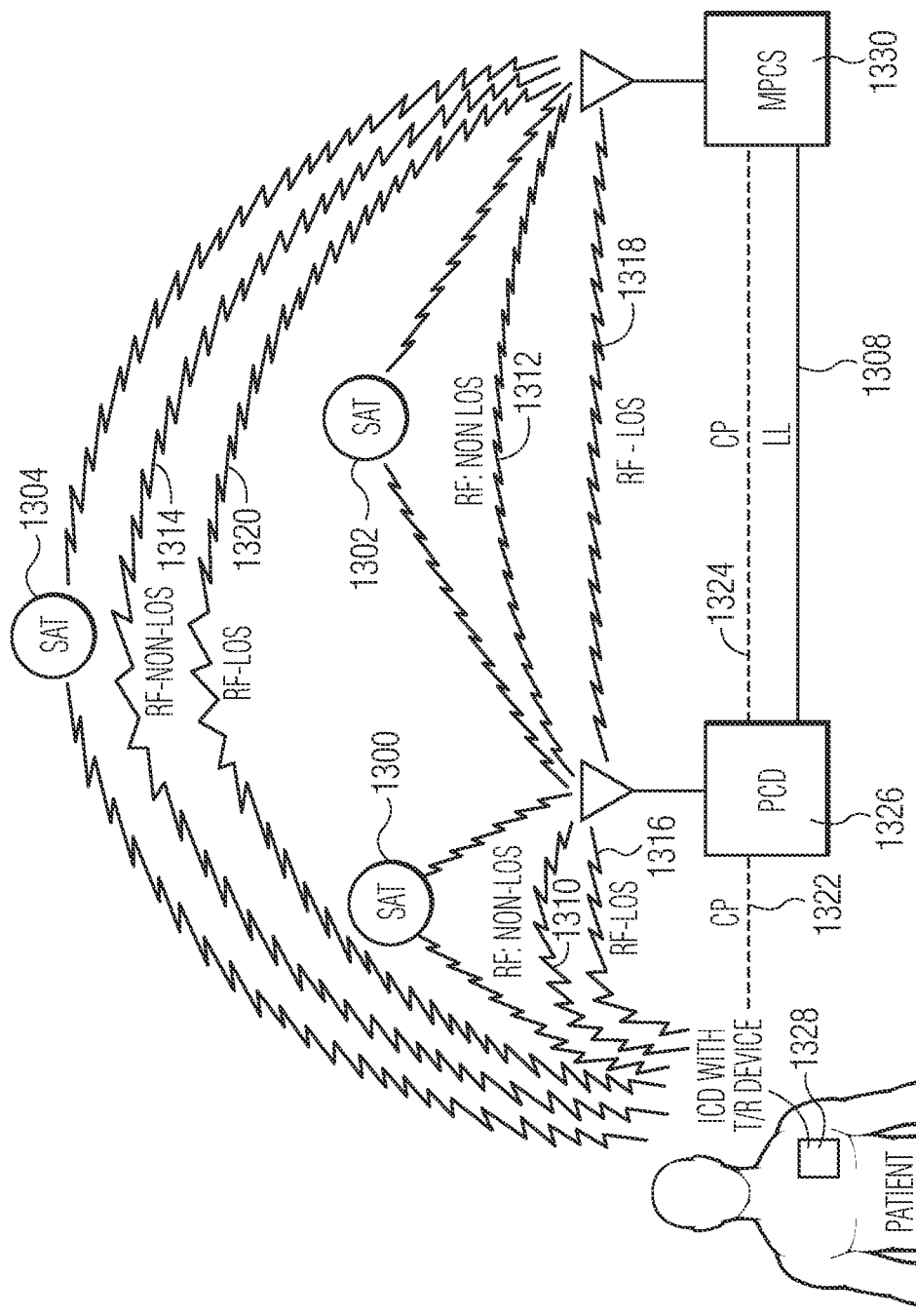
FIG. 10 shows a representational diagram of ICD communication via a personal communication device.

FIG. 10 shows that each segment of the communication route may be:
- A) via satellite(s) (1300, 1302 and 1304 in the figure, each of which may represent a single satellite or an array of multiple ones); B) via a non-line-of-sight radiofrequency link (1310, 1312, 1314); C) via a line-of-sight radiofrequency link (1316, 1318, 1320); D) via a public or private telephone network; E) via cell-phone and/or personal communication device network (1322, 1324); F) in the links beyond the ICD link, via "land lines 1308;" and/or G) combinations of A-F.

The PCD 1326 in figure PCD in FIG. 10 may be replaced by a wireless router such that the communication between the ICD and the MP is ICD 1328.rarw..fwdarw.wireless router.rarw..fwdarw.internet.rarw..fwdarw.MP communication station 1330. The route from the wireless router to the communication station can have a wide variety of configurations, as is known to those skilled in the art.

Figure 11:
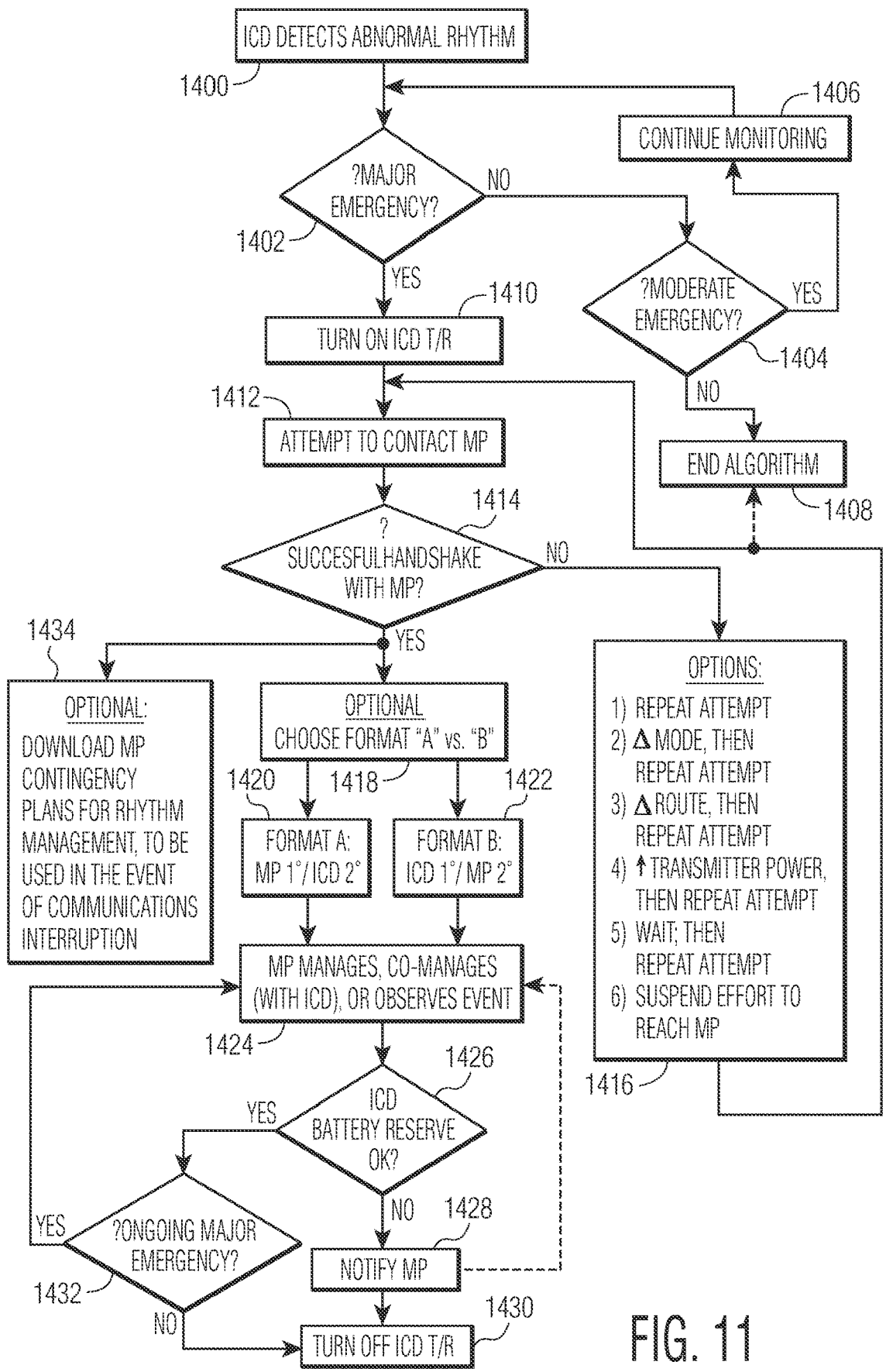
FIG. 11 shows a flow diagram of an ICD management algorithm allowing remote notification and management.

FIG. 11 shows one possible algorithm for allowing the ICD to communicate with a MP communication station, with or without an intervening repeater unit/cell phone/stationary unit/control unit.

If/when the ICD detects an abnormal heart rhythm that requires action, may require action or requires analysis, block 1400, it determines whether the rhythm requires communication with the MP. One method of determination is to classify rhythm abnormalities as either major or not major, and to communicate if the rhythm abnormality is major. This determination is made at block 1402.

The figure shows a setup with two levels of emergency, as described in Feature 8, hereinabove. If the rhythm is determined, block 1402, not to be a major emergency, but is a moderate emergency, block 1404, then continued monitoring, bock 1406, is in order, to monitor for the possibility of the event turning into a major emergency; If this occurs, return to block 1402, and proceed with major emergency section of the algorithm. If there is neither a major nor a moderate emergency, block (either because the emergency condition has resolved, or because there is an abnormality which is less urgent than even the moderate category), the algorithm shown in FIG. 11 ends. ICD monitoring, of course, continues as always.

If a major emergency is detected, block 1410, the ICD T/R is turned on. Not leaving it on continuously saves the battery charge. The ICD then attempts to contact the MP, block 1412. A handshake protocol, which may have some or all elements of that described in Ser. No. 10/460,458 or may have one or more features of other handshaking protocols as are known in the art, ensues, block 1414.

If the handshake is unsuccessful, or (optionally) if the quality of the handshake is sub-optimal, block 1416 lists six possible options. These include:
1) repeat attempt at handshake, using the same communication parameters;
2) change communication mode (as defined in Ser. No. 10/460,458) and repeat handshake attempt;
3) change communication route (as defined in Ser. No. 10/460,458) and repeat handshake attempt;
4) increase ICD transmitter power and repeat handshake attempt;
5) wait, and then repeat the handshake attempt, either with the same transmitter/mode/route parameters or one of more altered ones; and/or
6) suspend efforts to contact the MP.

In the case of the options 1-5, block 1416 leads to block 1412: a repeat attempt to contact the MP.

In the case of option 6, block 1416 leads to 1408 and the algorithm ends. Option 6 may be selected after a pre-programmed number of attempts to reach the MP has occurred. Alternatively, the number of attempts may not be pre-programmed and may depend on the ICD battery status (see hereinbelow), or the level of the emergency.

If the handshake is successful, than the MP will have the opportunity to participate in the management of the emergency. The format for such participation is:
a) pre-programmed Format A (MP control is primary; ICD control is in the event of communications interruption);
b) pre-programmed Format B (ICD control is primary; MP control in the event that the MP chooses to override the ICD decision);
c) either Format A or Format B, with the choice made by the MP at the time of the event; or
d) either Format A or Format B, with the choice made by the ICD based on the severity of the event.

As indicated hereinabove, the aforementioned Format selection is made, block 1418, leading to either Format A/block 1420, or Format B/block 1422. Thereafter the MP either manages, co-manages (with the ICD) or observes the emergency event, block 1424.

The communication between the ICD and the MP may terminate in one of three ways:
A) by necessity, because the ICD battery has reached a point in its discharge, where it is deemed unwise to continue communications;
B) due to the heart rhythm-related emergency having been resolved; or
C) due to an unintended interruption of communications.

In the event of A), block 1424 leads to 1426, which leads to a MP notification, block 1428. This may be followed by:
1) The ICD immediately turning off its T/R, block 1430;
2) The MP deciding to immediately turn off the ICD T/R, block 1430, or,
3) block 1424, the MP deciding to take some additional time to communicate, despite the low battery warning.

Algorithms which omit the warning to the MP of impending ICD T/R shutoff are possible.

In the event of B), block 1424 leads to 1426, which leads to 1432, which leads to 1430. In the event of C), attempts to re-establish communication occur, as described in Ser. No. 10/460,458. During the time when communication has not been established, the ICD logic unit manages the case.

To avoid a situation where the ICD logic unit must takeover in the middle of an event which the MP was managing in a different manner than would have been executed by the logic unit, the MP may, from time to time download contingency plans to the ICD, block 1434, such that, in the event of an interruption, the ICD has enough of the current MP decision making algorithm to complete the management of the event. This approach is discussed hereinabove, as Feature 13.

FIGS. 12 to 29 present apparatus, methods and approaches to securing dual IMD control i.e. [1] control by the internal/pre-programmed device management algorithm and [2] management control by an external source. The external source may be located remotely, nearby or may even be the patient himself/herself. The identification means presented hereinbelow are presented in applicant's U.S. patent and applications U.S. Pat. No. 8,233,672, Ser. No. 12/714,649, 13/563,399, and 13/834,634, which are all incorporated herein by reference.

Figure 12:
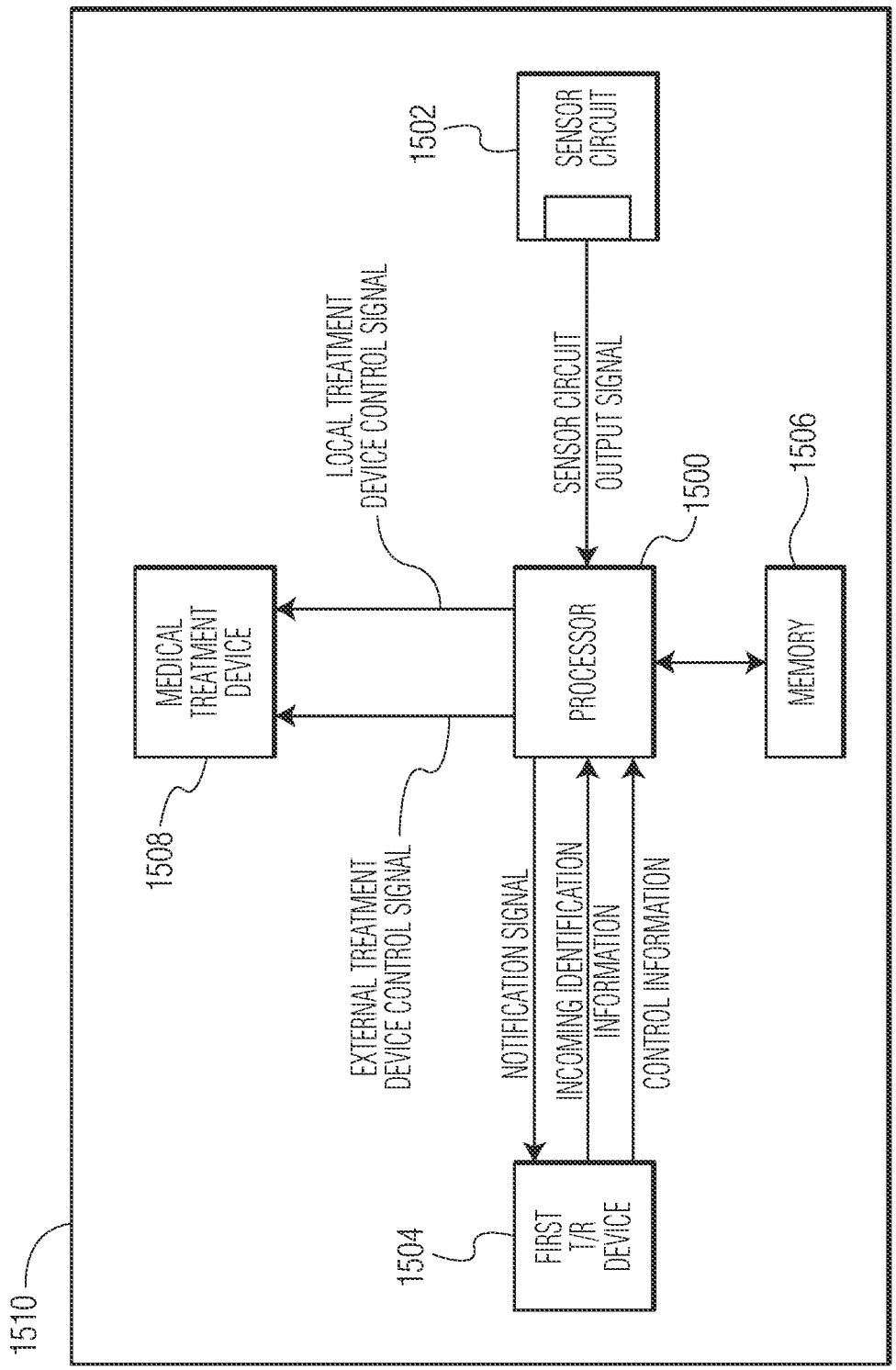
FIG. 12 shows a representational block diagram of a remotely and internally controllable IMD which determines the identification of a person wishing to remotely control the IMD.

FIG. 12 shows a remotely and internally controllable IMD which determines the identification of a person wishing to remotely control the IMD 1510. Processor 1500 receives signals containing physiologic information from sensor circuit 1502. The internal control algorithm leads to the "local treatment device control signal". Alternatively, as indicated hereinabove, 1500 may notify an external control source (person or device) via T/R device 1504, of the detection of a medical abnormality by sensor circuit 1502; processor 1500 may also cause the transmission of information representing the medical state detected by 1502, as indicated hereinabove. If the external source is to control this secure form of the IMD, the source must provide both (i) incoming identification information and (ii) control information (specifying a command, a device action, a temporary or permanent reprogramming etc). These are received by 1504 and provided to 1500. External control, if authorized, leads to the generation of an external treatment device control signal. As indicated hereinabove in conjunction with FIGS. 6A-6D, the treatment device 1508 may be controlled by either of the two sources, with a variety of prioritizing algorithms. Memory device 1506 stores identification information of allowed users, as discussed hereinbelow, and may store information and programs related to the operation of each of the device's systems, as is known in the art.

Figure 13:
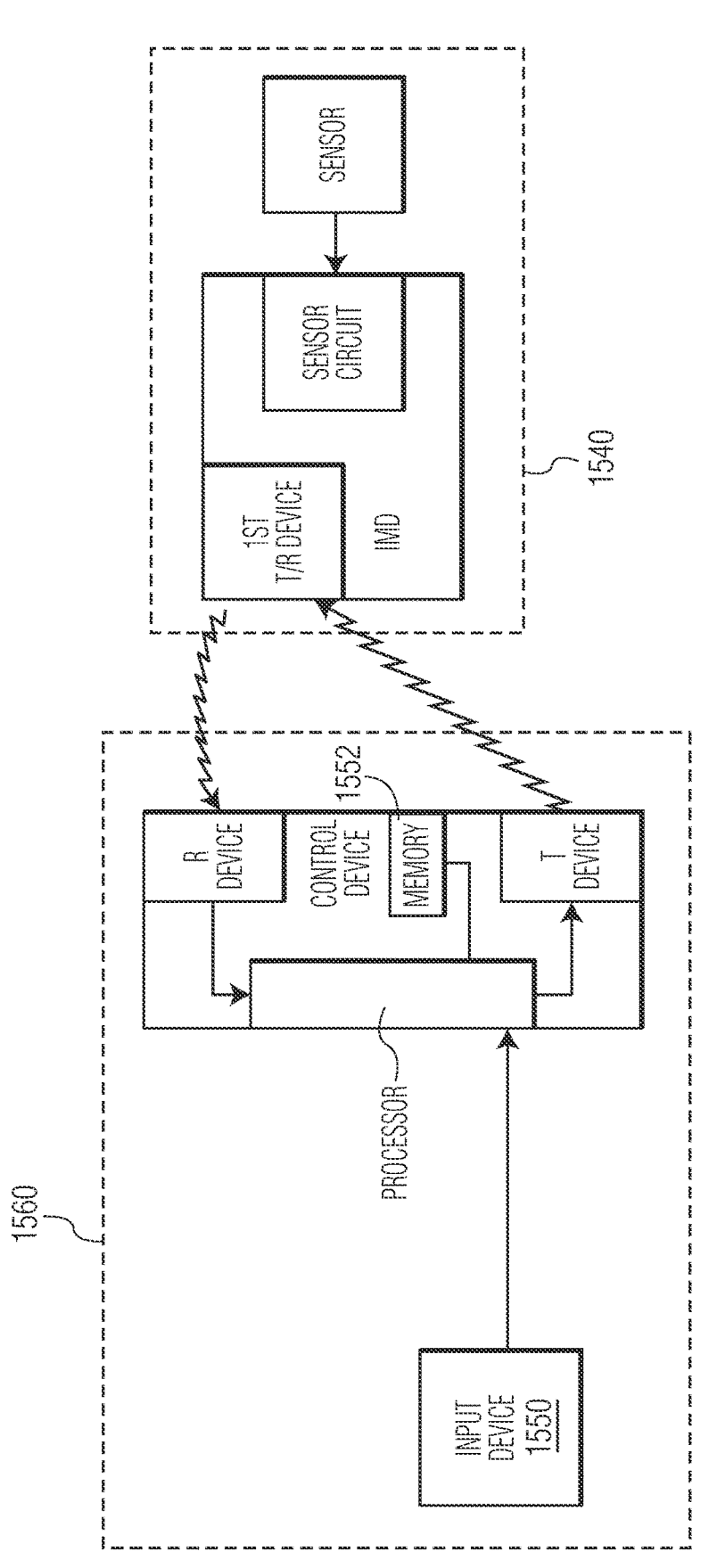
FIG. 13 shows a representational block diagram of a system with a remotely and internally controllable IMD which determines the identification of a person wishing to remotely control the IMD, and a remote control device with a single input for inputting both user identification and user device control information.

FIG. 13 shows a system with a remotely and internally controllable IMD 1540 which determines the identification of a person wishing to remotely control the IMD, and a remote control device 1560 with a single input device 1550 for inputting both user identification and user device control information. Memory 1552 may store (i) operating programs for the control device, and (ii) identification information of allowed users as will be described hereinafter with reference to FIGS. 19 and 20.

Figure 14:
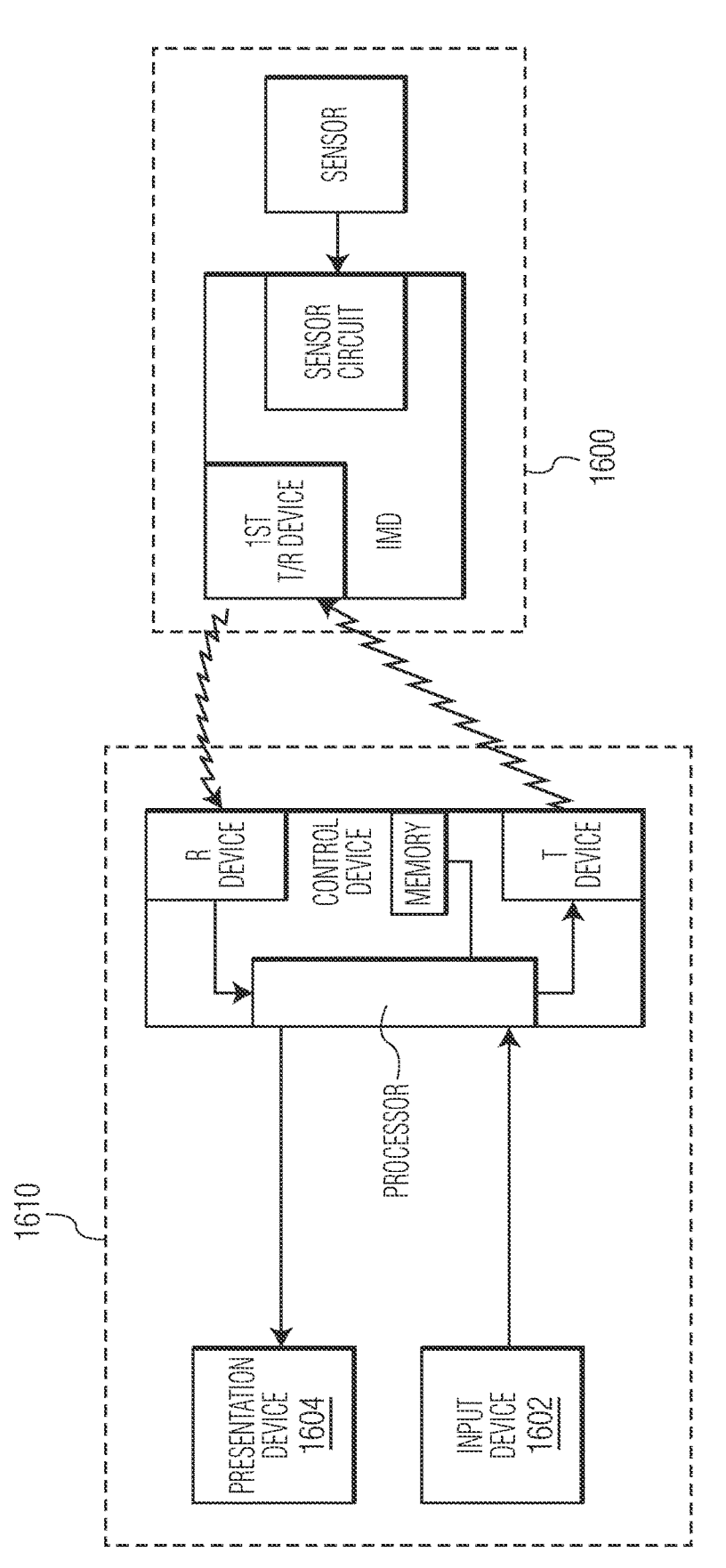
FIG. 14 shows a representational block diagram of a system with a remotely and internally controllable IMD which determines the identification of a person wishing to remotely control the IMD, and a remote control device with a single input for inputting both user identification and user device control information, and with a presentation device for displaying information for the user.

FIG. 14 shows a system with a remotely and internally controllable IMD 1600 which determines the identification of a person wishing to remotely control the IMD, and a remote control device 1610 with a single input device 1602 for inputting both user identification and user device control information. Presentation device 1604 presents information for the user. 1604 may be a screen of a computer system, a smartphone, television or any device for presenting visual information. Alternatively, it may a device for presenting audio information such as a speaker, earphone, smartphone, telephone, television etc.

Figure 15:
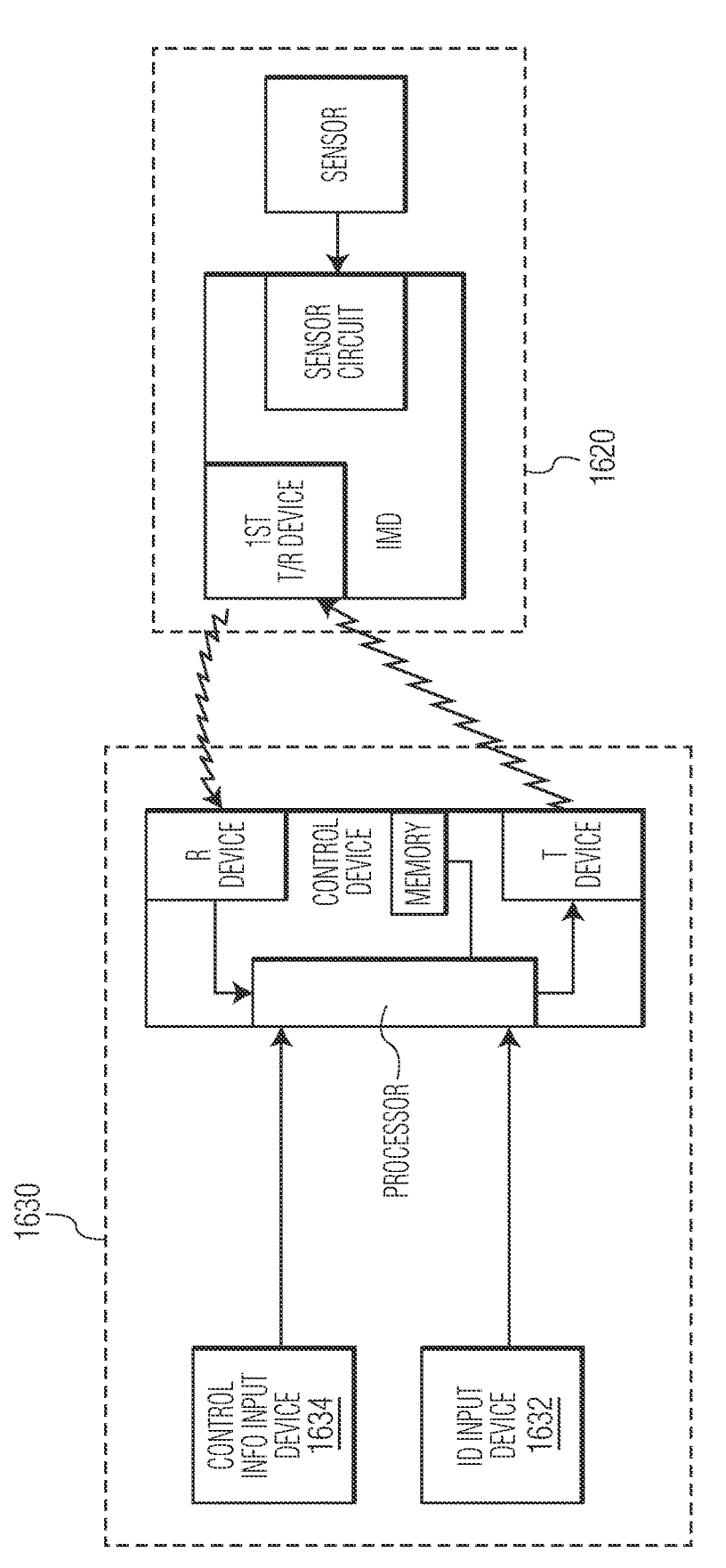
FIG. 15 shows a representational block diagram of a system with a remotely and internally controllable IMD which determines the identification of a person wishing to remotely control the IMD, and a remote control device with two inputs: one for inputting identification information and another one for inputting device control information.

FIG. 15 shows a system with a remotely and internally controllable IMD 1620 which determines the identification of a person wishing to remotely control the IMD, and a control device 1630 with two inputs: one for inputting identification information 1632, and another one for inputting device control information, 1634.

Figure 16:
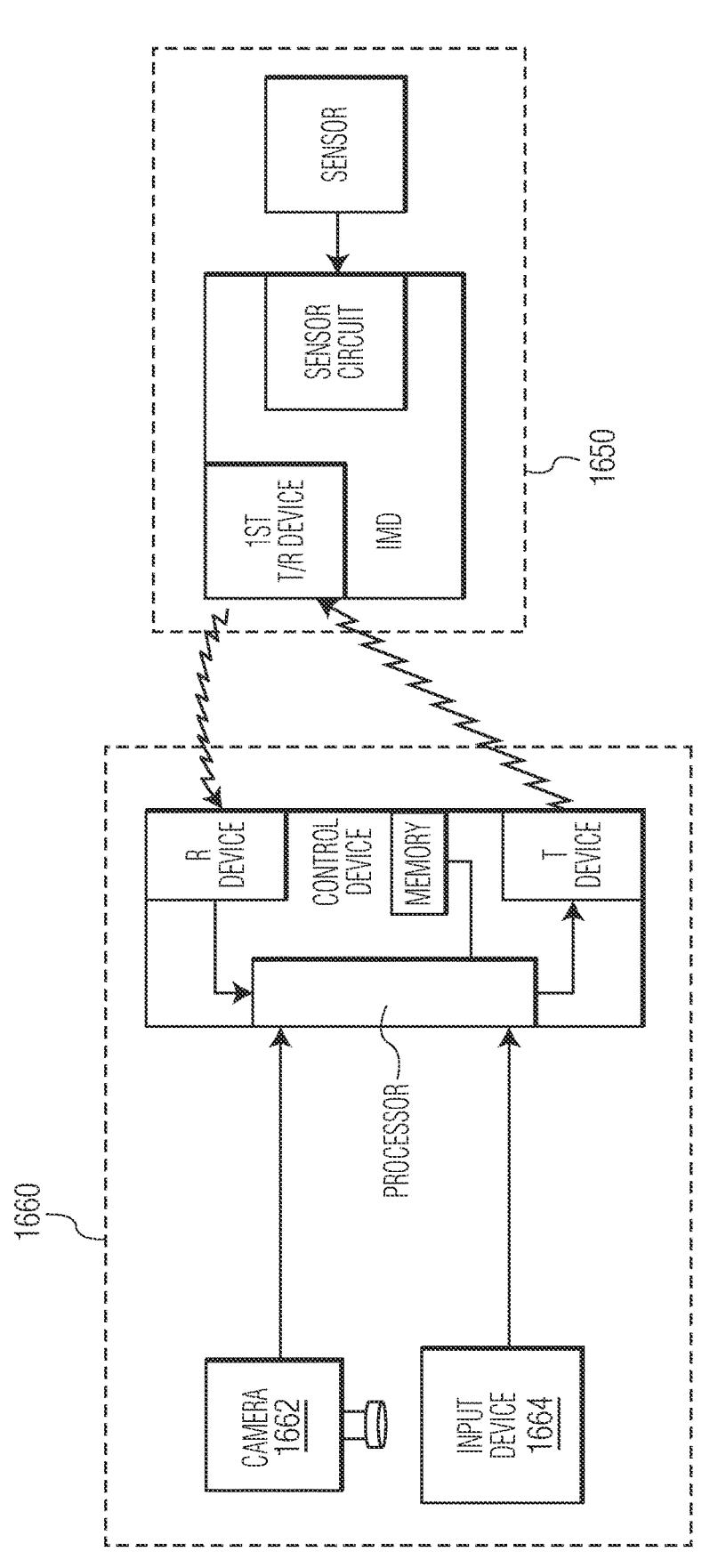
FIG. 16 shows a representational block diagram of a system with a remotely and internally controllable IMD which determines the identification of a person wishing to remotely control the IMD; and a remote control device with two inputs: a camera and a second input device.

FIG. 16 shows a system with a remotely and internally controllable IMD 1650 which determines the identification of a person wishing to remotely control the IMD; and a remote control device 1660 with two inputs: a camera 1662, and a second input device 1664. As shown in the figure the camera may image the control information input device 1664, which provides enhanced user identification, as discussed hereinbelow.

Figure 17:
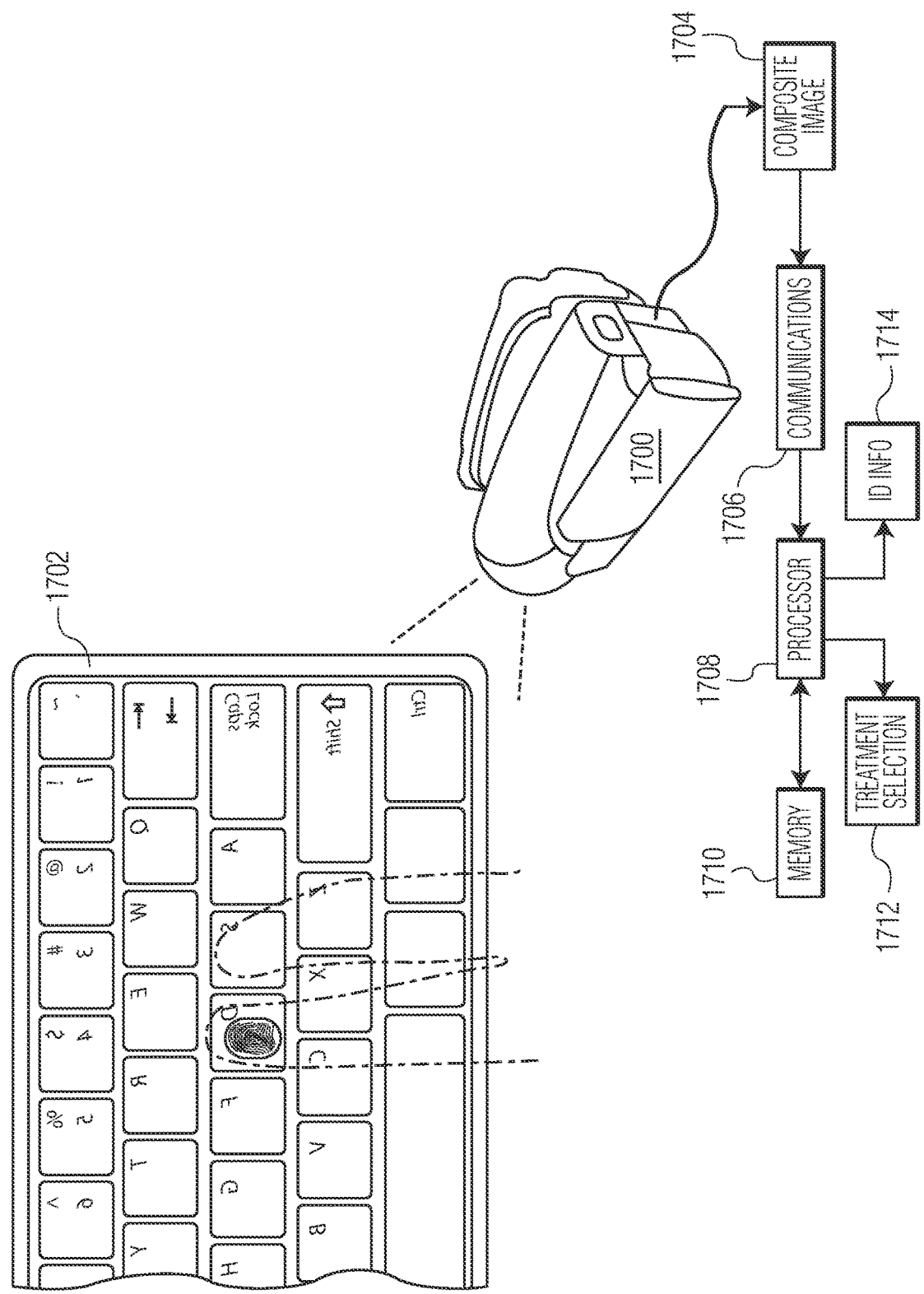
FIG. 17 is a representational block diagram of the system of FIG. 13, with a camera providing both control and identification information.

FIG. 17 is a diagram of the system of FIG. 13, with a camera 1700 providing a composite image showing both control and identification information. In the particular embodiment shown in the FIG. 1700 images a keyboard 1702 from below. The keyboard has semitransparent keys, allowing the observation by 1700 of both a keyboard entry and a biologic identifier—a fingerprint—as the associated finger inputs the keyboard entry. The keyboard may be mechanical, virtual, a touch sensitive screen or any other such apparatus as is known in the art. Although one typical key array is shown, the keyboard may consist of any pattern of keys with any markings (e.g. "defibrillate" "pace", etc.).

The composite image output 1704 of camera 1700 is passed by communications system 1706 to IMD processor 1708. 1708 compares the fingerprint image information in memory 1710 (discussed hereinbelow) with identification information 1714 obtained from the composite image to determine if the user attempting to gain access to the IMD is authorized. If he/she is authorized, the choice of treatment selection 1712 represented by image 1704 (indicated in the exemplary figure by the selection of the "D" key, but intended to be entirely general) is executed.

Figure 20:
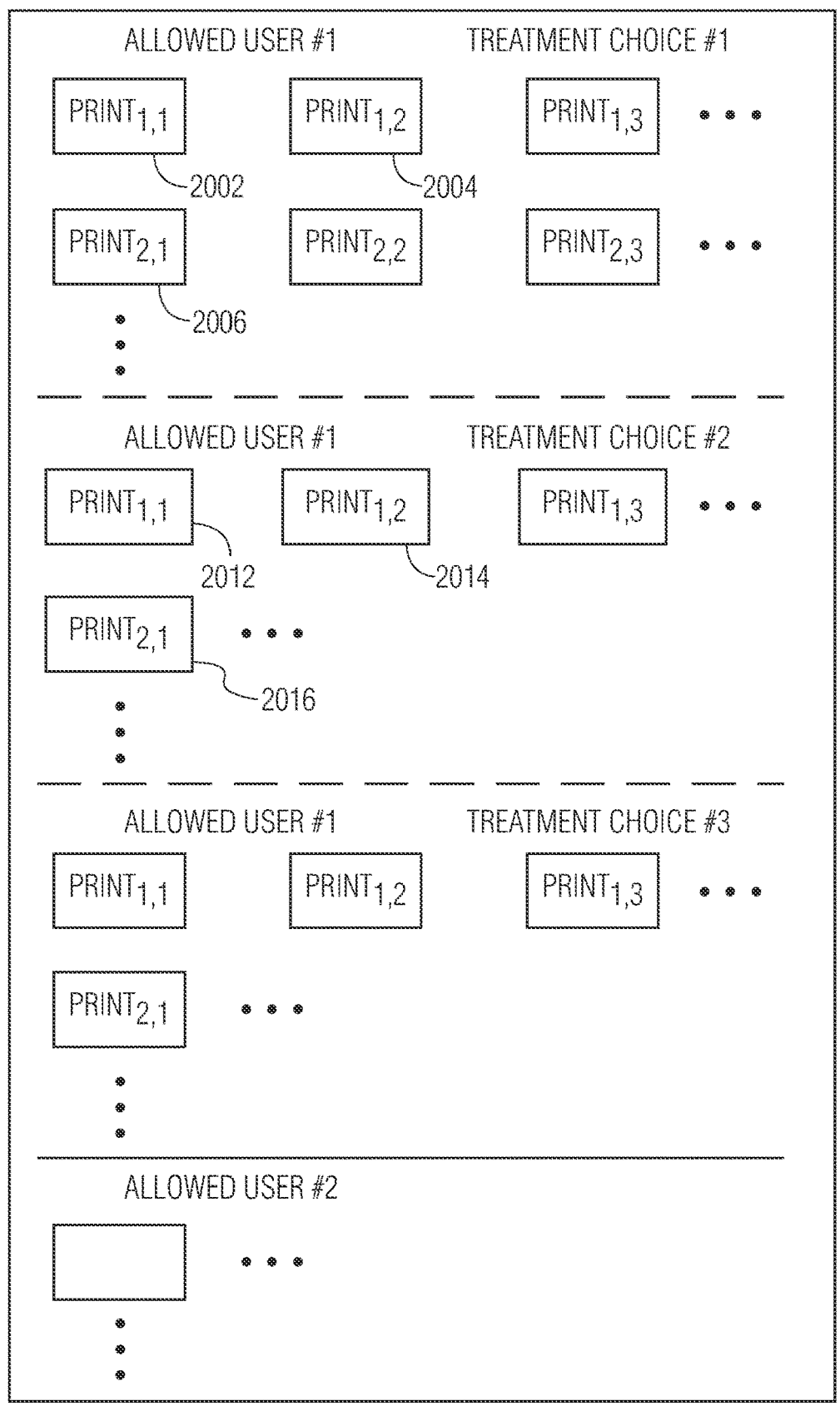
FIG. 20 is another representational diagram of memory file notation and allocation in the dual control IMD system.

In an alternate embodiment of the invention, 1708 compares image 1704 with a library of images in memory, each image showing both a biologic identification and a treatment selection, as shown in FIG. 20. For example, memory file 2002, labeled PRINT 1,1 contains data representing one image of fingerprint #1 of user #1 selecting treatment #1. 2004 contains a representation of a second image of fingerprint #1 of user #1 selecting treatment #1. 2006 contains a representation of fingerprint #2 of user #1 selecting treatment #1, etc. Similarly, memory file 2012, also labeled PRINT 1,1 contains data representing one image of fingerprint #1 of user #1 selecting treatment #2. 2014 contains a representation of a second image of fingerprint #1 of user #1 selecting treatment #2. 2006 contains a representation of fingerprint #2 of user #1 selecting treatment #2, etc.

Similarly, the array below that which pertains to treatment #2, pertains to treatment #3. One such array would be stored for each possible treatment choice. And one such set of arrays would be stored for each allowed/authorized user.

In this alternative embodiment, the processor need not extract the ID image and/or the treatment selection. That is, the two would be identified "en bloc" as indicated hereinabove.

Other means of image identification and analysis will be clear to those skilled in the art.

Figure 19:
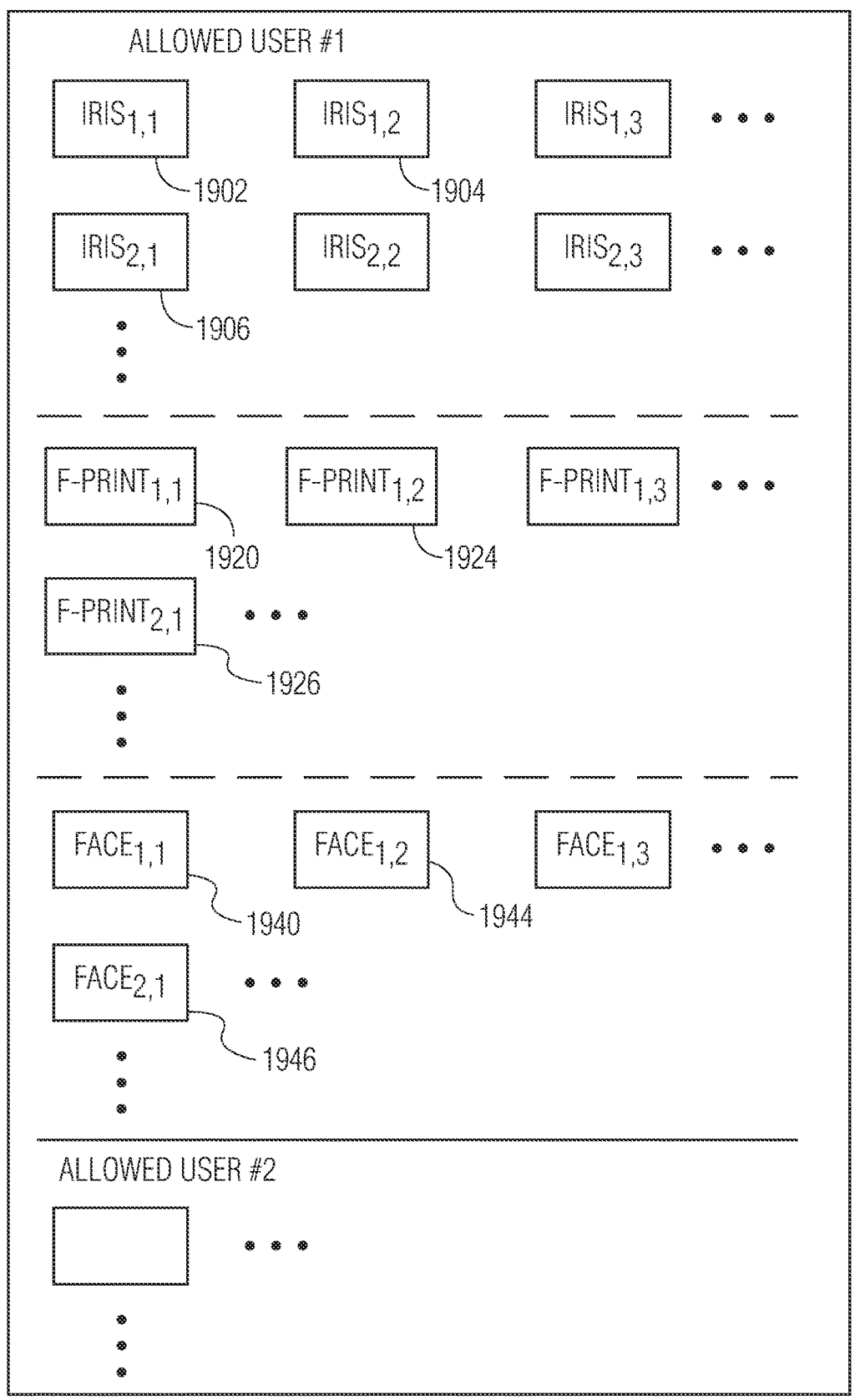
FIG. 19 is a representational diagram of memory file notation and allocation in the dual control IMD system.

FIG. 19 is another diagram of memory file notation and allocation in the dual control IMD system which addresses the confounding effects of lighting and image/camera relative geometry, and is discussed further hereinbelow.

Figure 18:
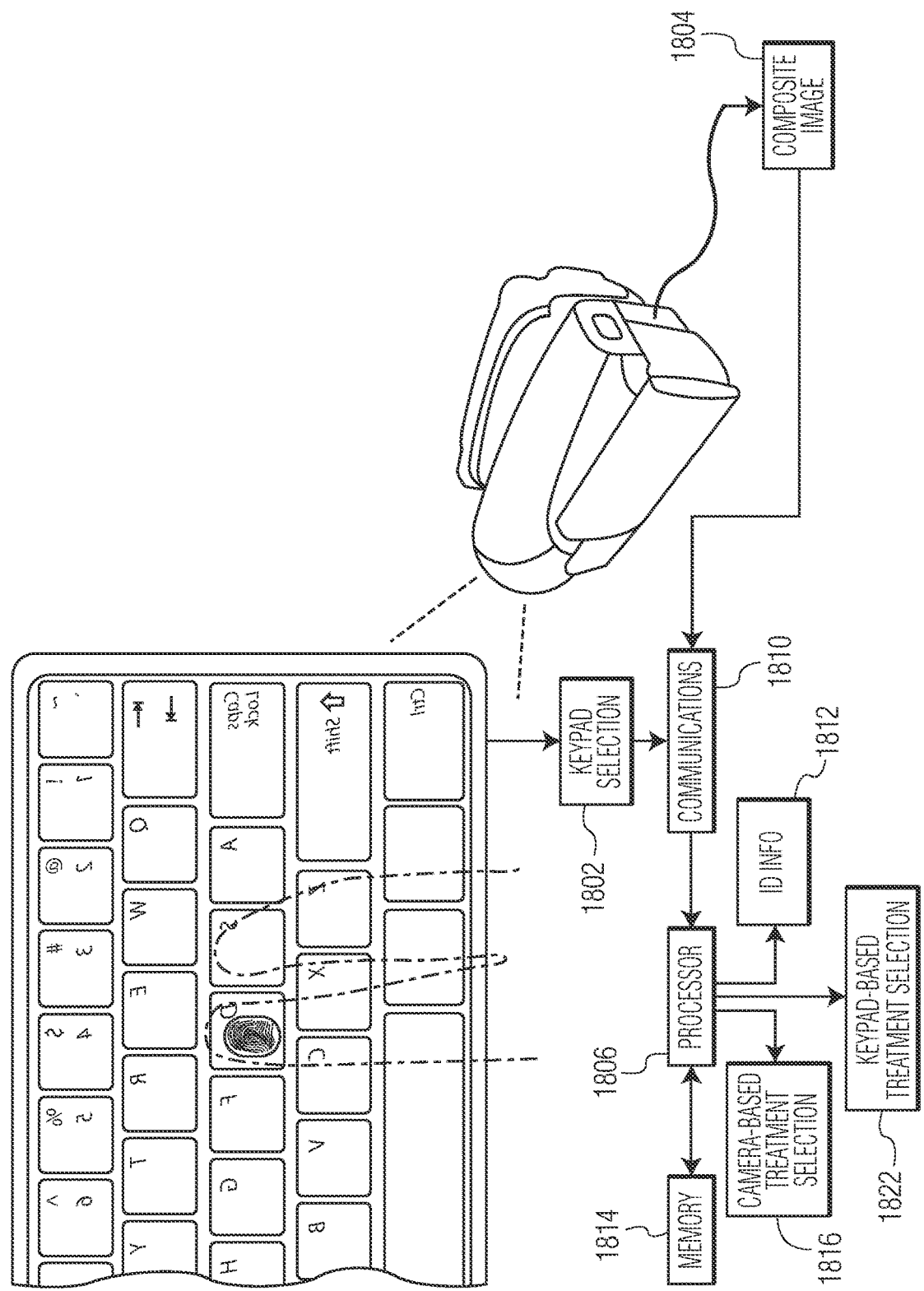
FIG. 18 is a representational block diagram of the dual control IMD system with both camera and keypad inputs.

FIG. 18 is a diagram of the dual control IMD system with both camera and keypad inputs. It differs from FIG. 17 in that keyboard selection information 1802 is also supplied to processor 1806 (i.e. in addition to supplying the composite image 1804 to the processor), both via communications system 1810. 1806 generates identification information 1812 by either of the two approaches discussed hereinabove in conjunction with FIG. 17. Treatment selection information is obtained either directly from the keyboard information (1822, from 1802) or is obtained (by either of the two approaches discussed in conjunction with FIG. 17) as 1816, from composite image 1804. Comparison of the camera-based treatment selection 1816, and the keypad-based selection 1822, yields potential further security: It links keyboard output 1802 to the fingerprint image 1812 in a more secure way than would be the case if the keyboard entry was not part of the composite image. Memory 1814 serves the same function as that of 1710 in FIG. 17.

Figure 21:
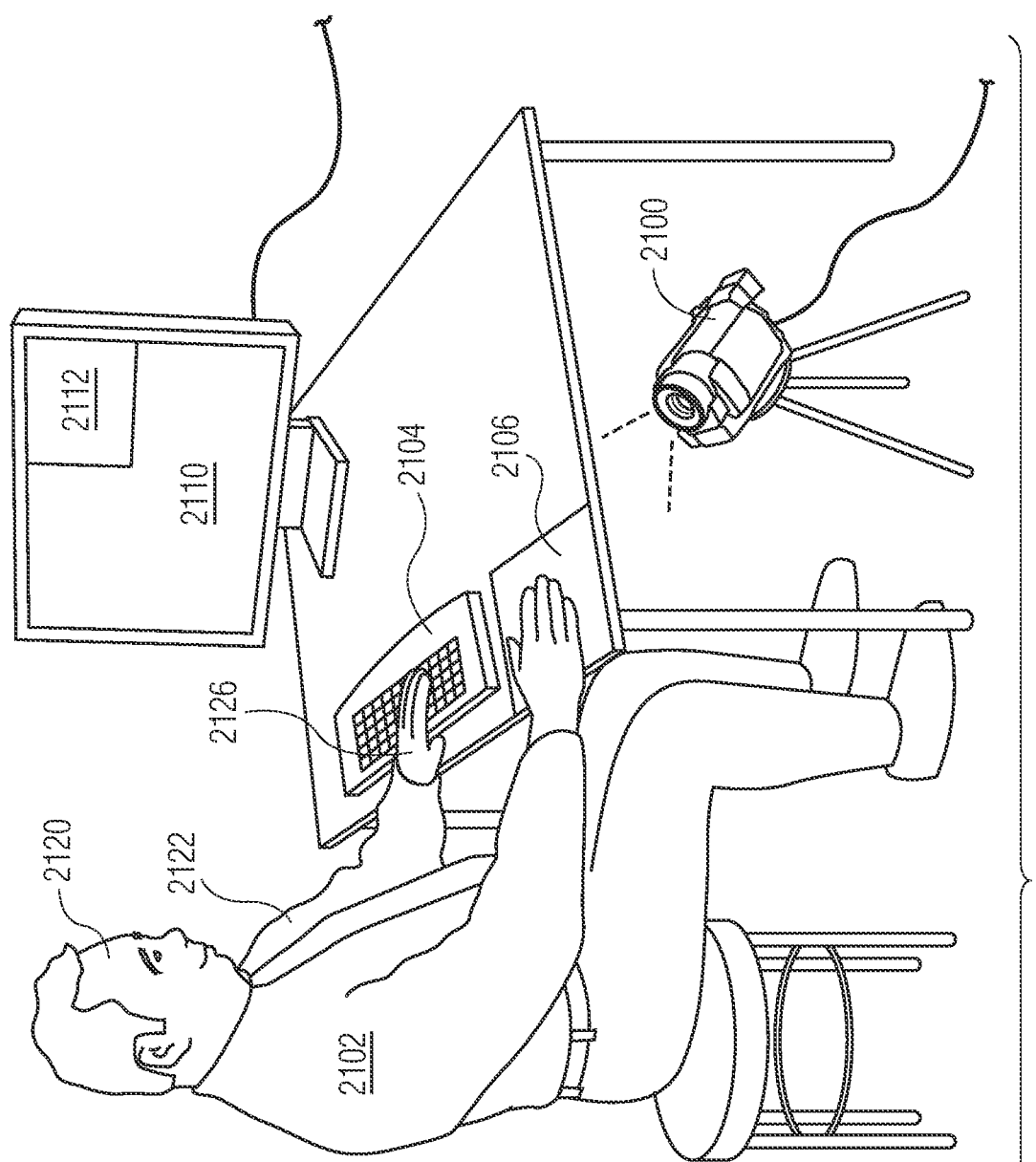
FIG. 21 is a representational diagram illustrating the dual acquisition of biologic identification information and control information.
Figure 21:
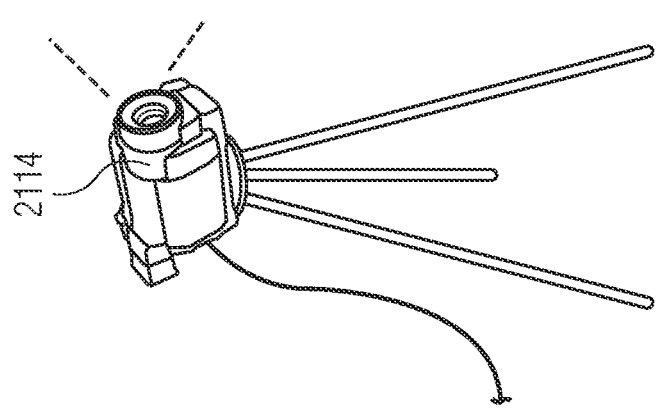

FIG. 21 illustrates the dual acquisition of biologic identification information and control information. As discussed in U.S. Pat. No. 8,233,672, camera 2100 images both (i) keyboard entries (via 2104) of treatment commands and (ii) either (a) one or more the fingerprints via 2104 or 2106, (b) a palm print or an image of hand/finger vasculature via 2106, or (c) a facial image of user 2102. Camera 2114 may image the face of 2102 or his/her keyboard selection via reflecting surface 2112. Alternatively 2114 may input the actions of the user inputting entries to a touch sensitive screen 2110, and also image the face of 2102 in the same image. Any of the cameras may also image iris related identification features; camera locations for these acquisitions need not be limited to those shown in the figure; numerous/limitless other configurations are possible. FIG. 21 also illustrates the approach to dealing with a determination that (as opposed to the keyboard situation of FIGS. 17 and 18) an identification image obtained from a body part (e.g. the face) which is not the body part which inputs the treatment selection, is part of the same individual as the body part which inputs a treatment selection. This is accomplished by imaging the contiguous body parts lying between the source of the biologic identifier and the body part making the treatment selection. Thus camera 2100 may image face 2120, arm 2122, hand 2126 and keyboard entry using 2104 (without fingerprint identification); In this case, the face is the biologic identifier linked to the keyboard entry. (In actuality, the neck and upper left portion of the torso would also need to be imaged to complete the contiguous body part pathway.)

Figure 22:
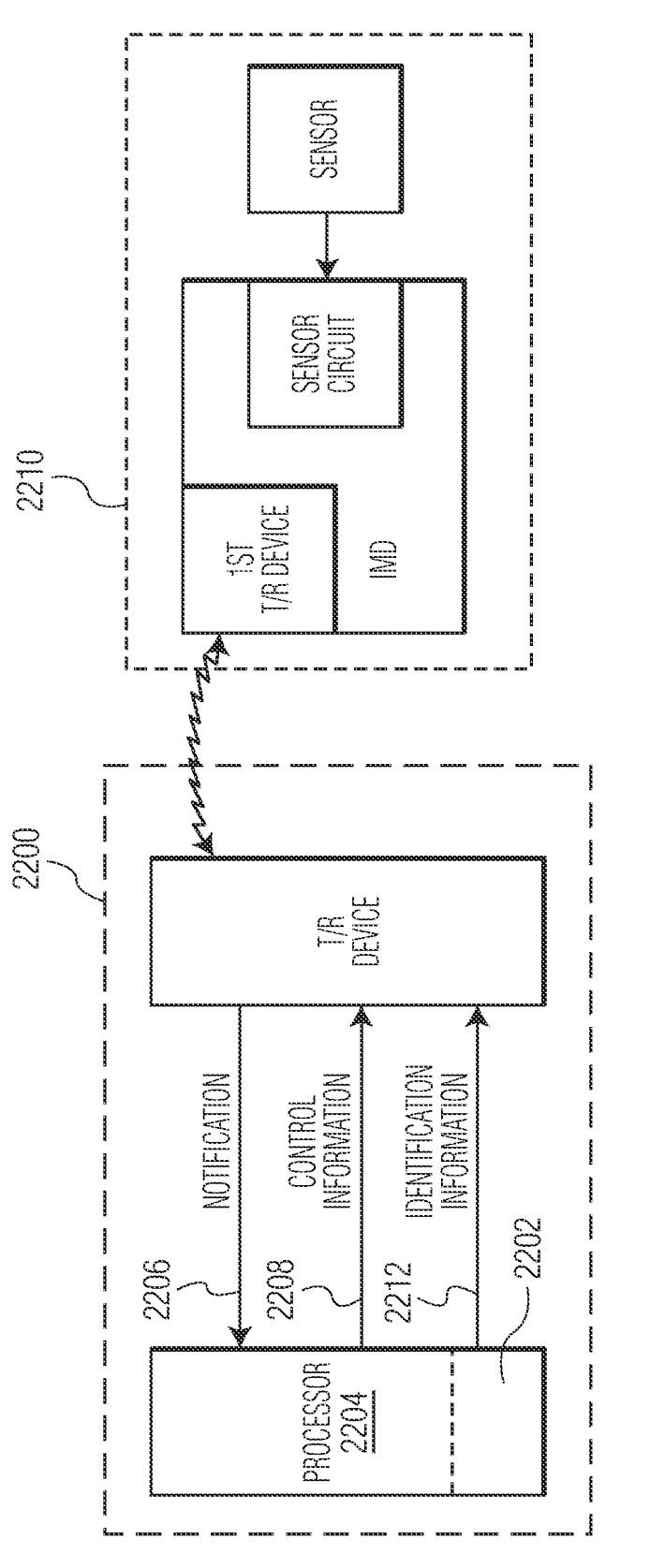
FIG. 22 is a representation block diagram of an automatically operating remote control station for the dual control IMD, with identification of the remote control station.

FIG. 22 is a block diagram of an automatically operating remote control station 2200 for the dual control IMD, with identification of the remote control station. A processor 2204 analyzes the information in notification signal(s) 2206 and thereafter renders a decision about IMD control and/or management, transmitted to IMD 2210 as control information 2208. Identification information 2212 pertains to the control device and may "reside" in the processor (represented by 2202 within 2204) or in a separate memory device.

Biodynamic identification is the subject of material incorporated by reference. It refers to the remote manipulation of a biologic identifier by the entity that wishes further confirmation that the received biologic identification information is authentic. A simple example is the remote manipulation of the size of the pupil and iris of an eye as the intensity of an applied light is remotely varied. Since the entity performing the identification varies the light source intensity, and can do so in a way known only to that entity, defeating such a system (e.g. with an inappropriately obtained static iris image) will not be possible.

Figure 23:
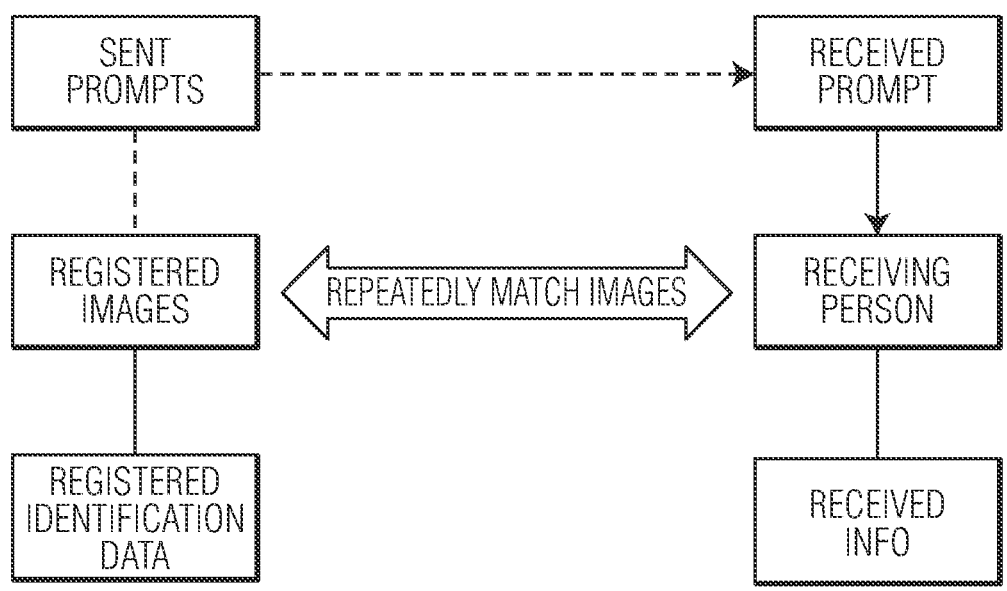
FIG. 23 is a representational block diagram of the use of prompts to identify a device user.

FIG. 23 is a block diagram of the use of prompts to identify a device user, appearing in material incorporated by reference.

FIG. 19 shows a memory arrangement intended to be useful for variable lighting and other orientation issues. Element 1902 "IRIS 1,1" indicates a file representing one appearance of an iris of user #1 with lighting intensity #1. 1904 is a second example of the same iris of the same person, with the same lighting conditions on another occasion. 1906 is the same iris with a different lighting intensity.

Fingerprint data 1920, 1924 and 1926 are each analogous to 1902, 1904 and 1906 respectively; and facial image data 1940, 1944 and 1946 are each analogous to 1902, 1904 and 1906 respectively.

Figure 24:
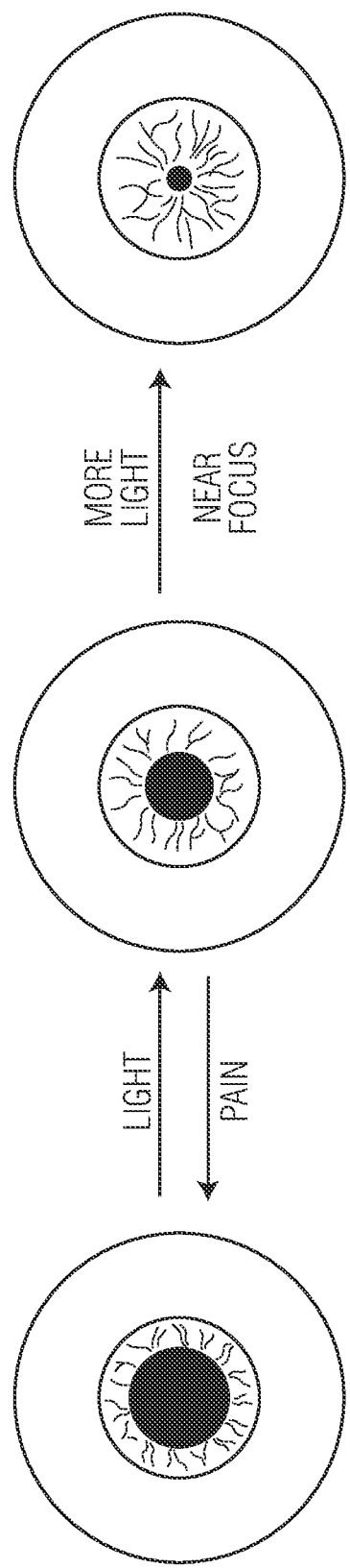
FIG. 24 is a representational diagram of the response of a human iris to light and to other prompts.

FIG. 24 shows the response of the iris/pupil to various light intensities. Pain and focusing efforts also change the size of the pupil/iris, also discussed in material incorporated by reference.

Figure 25:
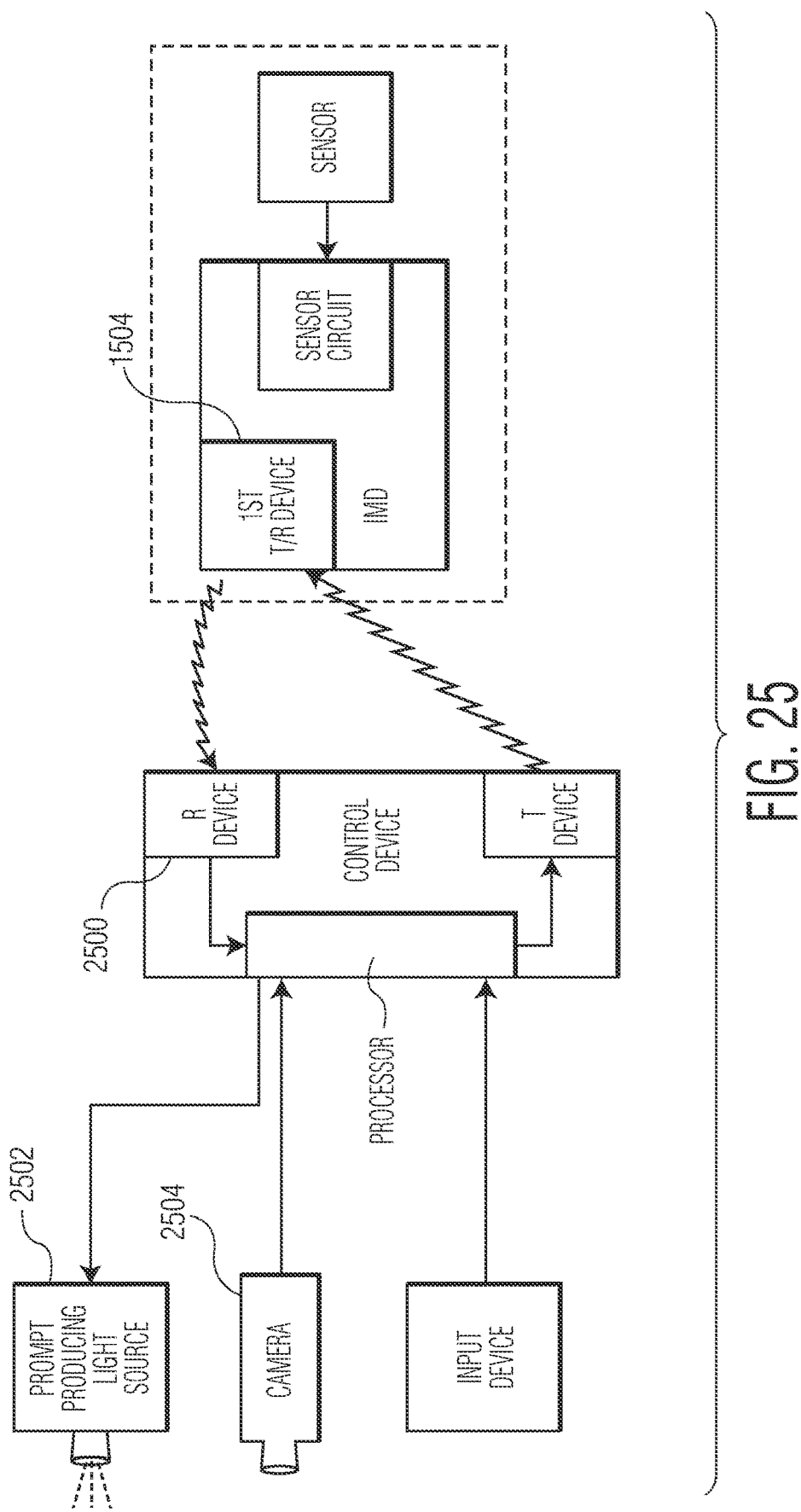
FIG. 25 is a representational block diagram of the user identified, dual control IMD with a light source supplying prompts, a camera and another input device.

FIG. 25 is a diagram of the user identified, dual control IMD with a remotely controllable light source supplying prompts 2502, a camera 2504 and another (optional) input device; the prompts are controlled by the IMD processor (1500 of FIG. 12), and are transmitted by 1504 to receiving device 2500—as taught by the aforesaid U.S. patent application Ser. No. 13/563,399 (U.S. Patent Pub. No. 2012/0314048) in which FIGS. 16B and 16C and the associated specification illustrate prompt control by each of remote processors 1646 and 1670 respectively.

Figure 26:
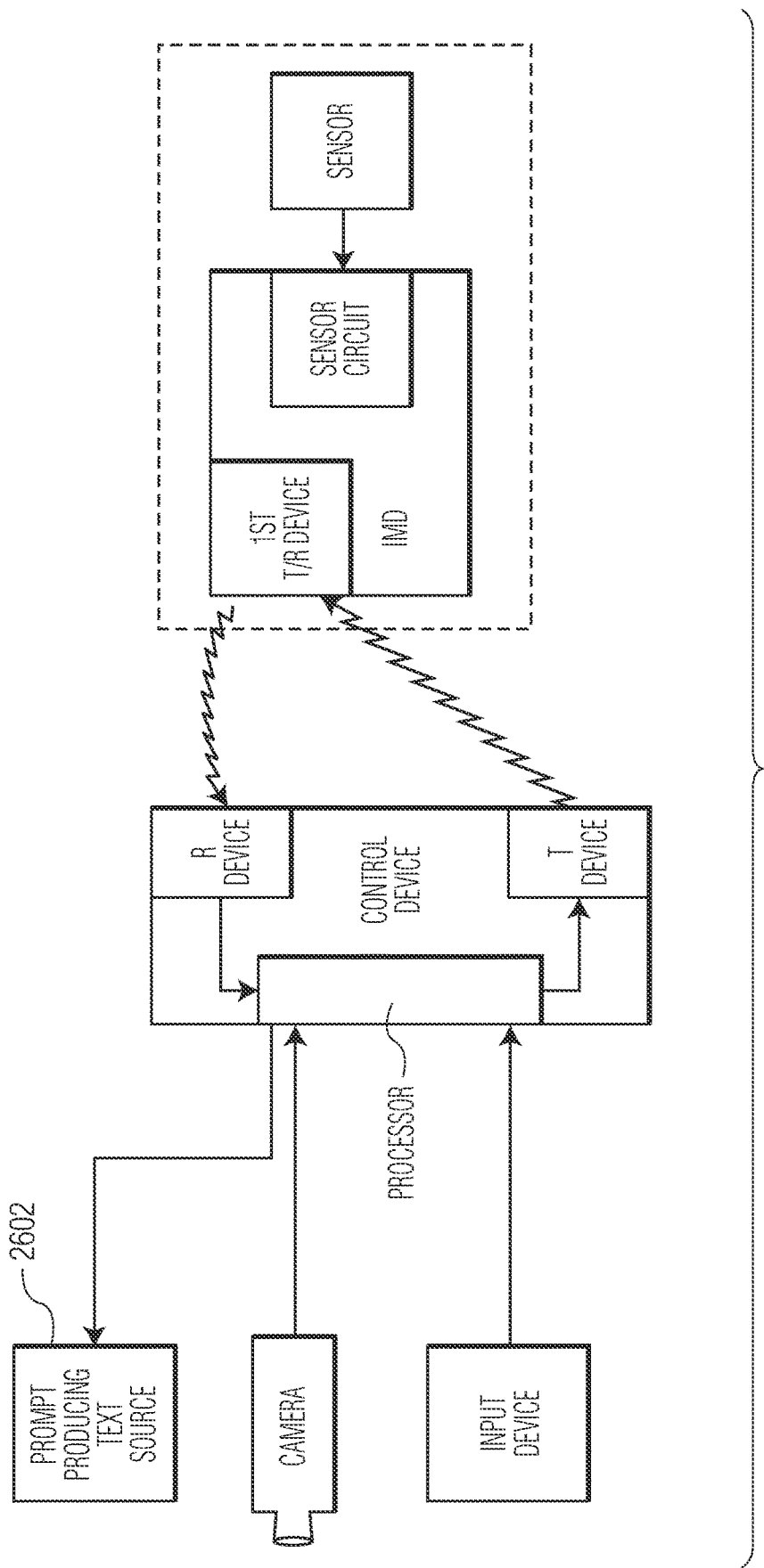
FIG. 26 is a representational block diagram of the user identified, dual control IMD with a text source supplying prompts, a camera and another input device.

FIG. 26 is diagram of the user identified, dual control IMD with a text source 2602 supplying prompts, a camera and another input device. The text source may emit audio instructions requesting various actions of the user, e.g. change position of a certain body part, blink, etc. As in the case of the embodiment of FIG. 25 herein, the IMD processor (1500 of FIG. 12) is the source of the prompt selection.

Figure 27:
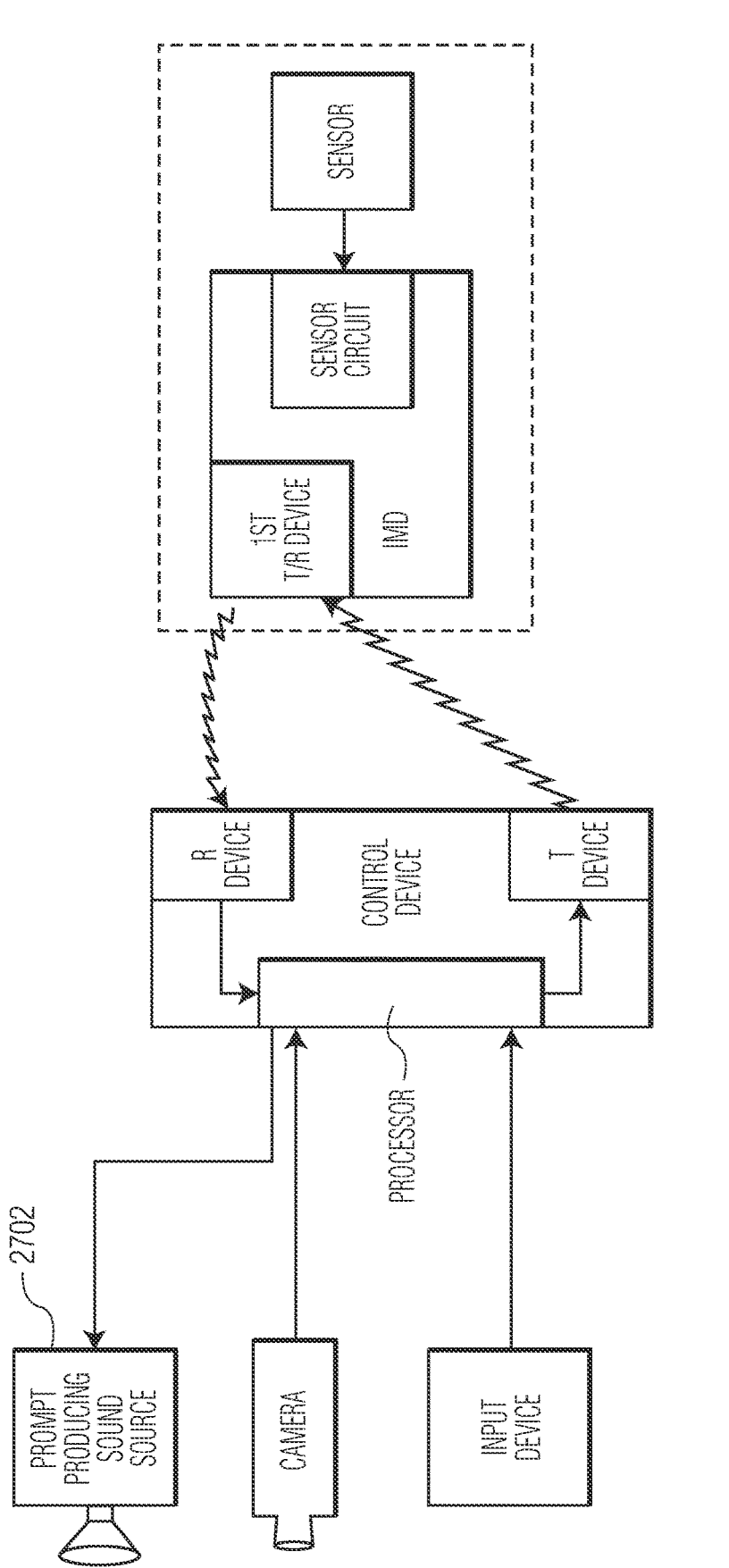
FIG. 27 is a representational block diagram of the user identified, dual control IMD with a sound source supplying prompts, a camera and another input device.

FIG. 27 is a representational block diagram of the user identified, dual control IMD with a sound source 2702 supplying prompts, a camera and another input device. The sound source may emit audio instructions requesting various actions of the user, e.g. change position of a certain body part, blink, etc. The IMD processor (1500 of FIG. 12) is the source of the prompt selection.

Figure 28:
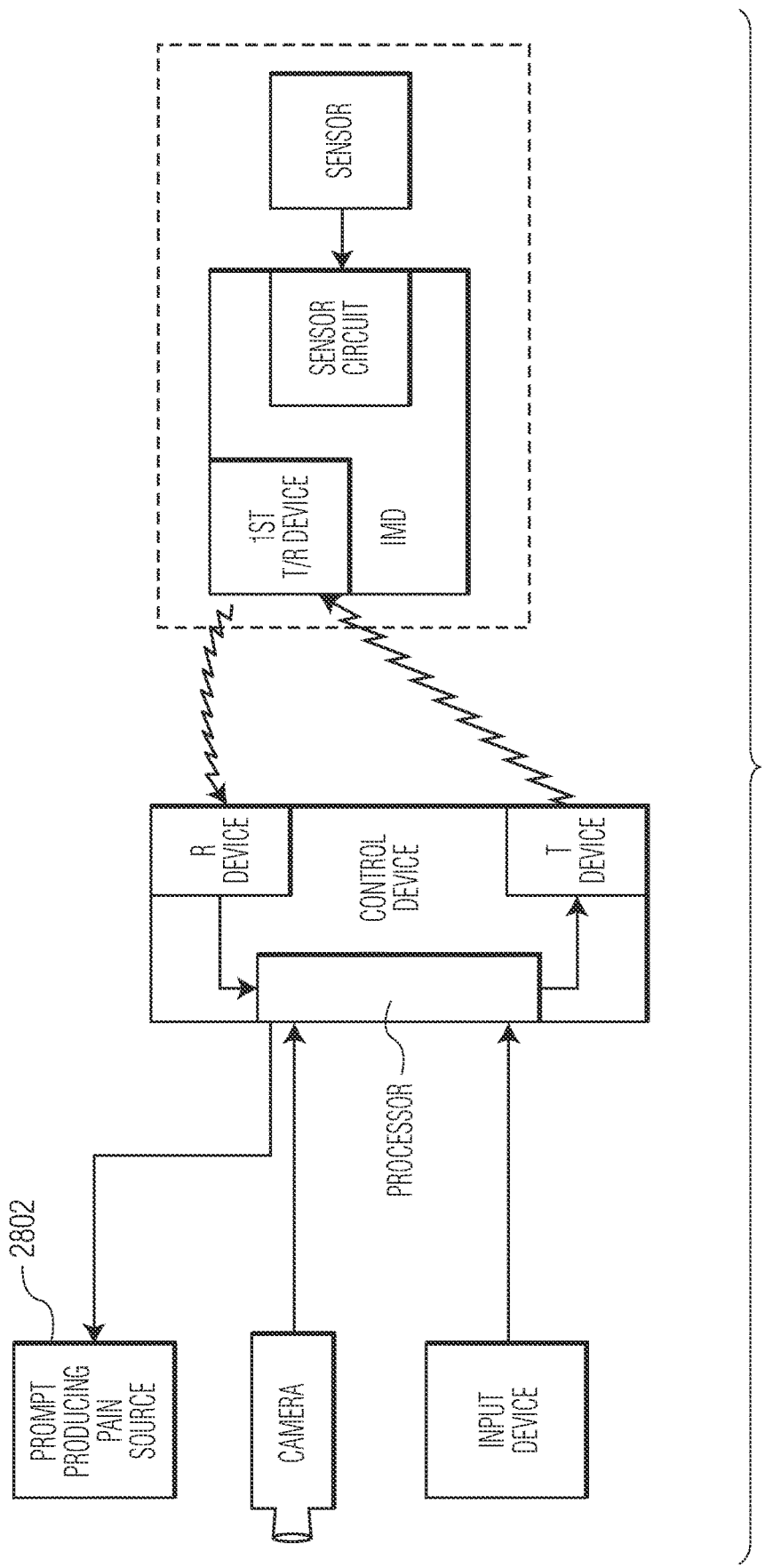
FIG. 28 is a representational block diagram of the user identified, dual control IMD with a pain source supplying prompts, a camera and another input device.

FIG. 28 is a representational block diagram of the user identified, dual control IMD with a pain source 2802 supplying prompts, a camera and another input device. As indicated in conjunction with FIG. 24, the application of pain may affect pupil/iris size. The IMD processor (1500 of FIG. 12) is the source of the prompt selection.

Figure 29:
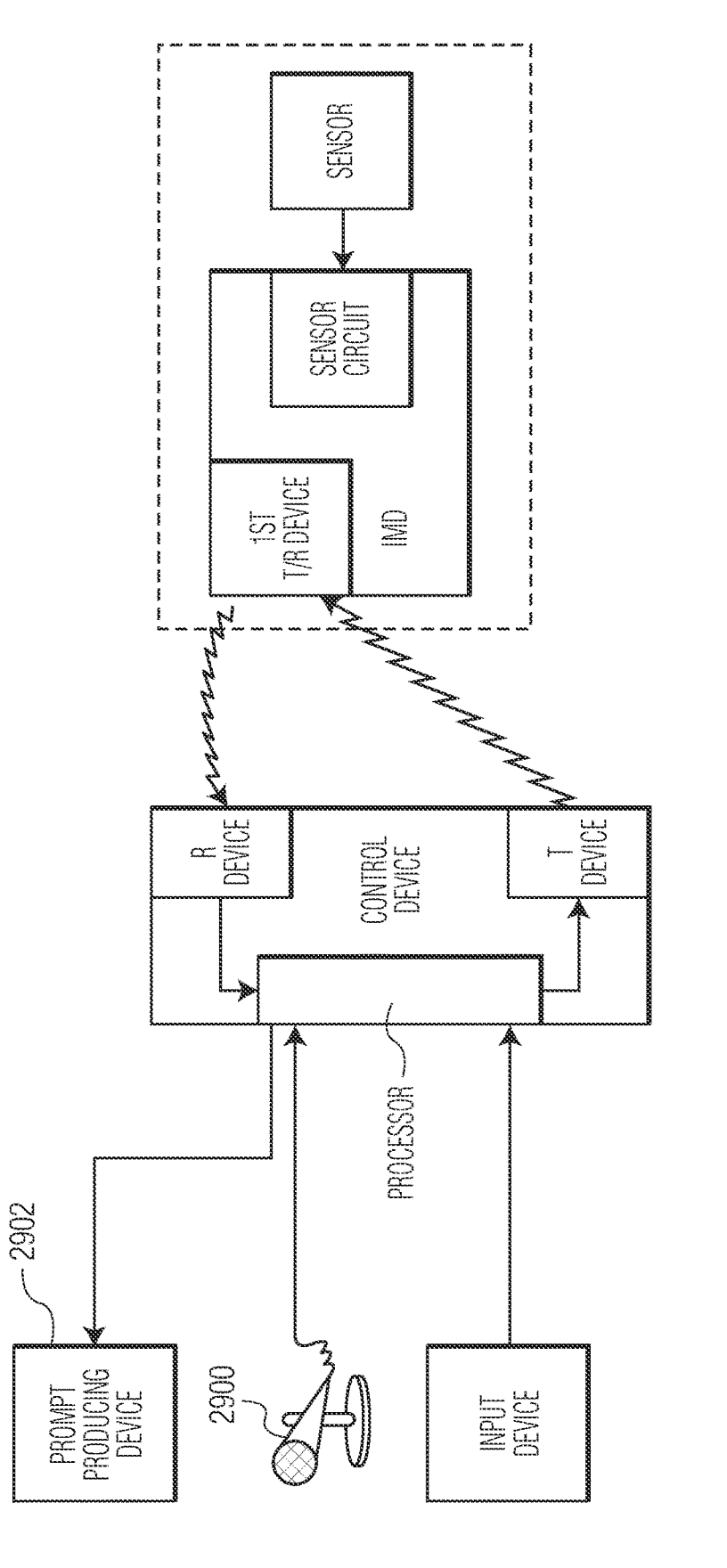
FIG. 29 is a representational block diagram of the user identified, dual control IMD with a prompt producing device, a microphone and another input device.

FIG. 29 is a representational block diagram of the user identified, dual control IMD with a prompt producing device, a microphone 2900 and another input device. Prompt producing device 2902 may issue video, audio or text instructions to a user to speak certain words. These words may serve as the biologic identifier. A camera or other input device may supplement this arrangement. The IMD processor (1500 of FIG. 12) is the source of the prompt selection.

Having considered, hereinabove, apparatus and techniques for the identification of a person who wishes to remotely control an implanted device, it is next appropriate to consider apparatus and techniques for determining with a high degree of certainty, from a remote control station (which need not be geographically remote), which device is to be controlled by a remote control signal to be sent, or is being controlled by a remote control signal that has been sent. In principle, an approach as simple as knowing a communications address of the device could be utilized. However, situations in which such an approach may lead to errors include the initial registration of a wrong set of device identification information, the replacement of a device without the knowledge of the user (i.e. the entity sending the device control signal), and other situations. Given the at-times mission-critical nature of some remotely controlled devices, all approaches that reduce such uncertainty to the most minimum value is desirable.

Two such approaches are presented hereinbelow. The first entails briefly and or intermittently taking control of a remotely controlled pacing system and slightly modifying a pacing parameter or modality, followed immediately by the remote observation of the effect of such modification. The second entails briefly and or intermittently taking control of a remotely controlled stimulation system that need not be a pacing system—and providing stimulation which can be remotely observed in a return signal. Finally, it is shown hereinbelow that the apparatus which accomplishes the approach of the second embodiment of the invention can be used for a highly secure means of two-party communication.

Implicit in these approaches is the comingling of (A) biologic identification—in this case a fingerprint, with (B) identification of a change in a physiologic parameter—in this case (i) the heart rate (as judged by (a) the electrocardiogram or (b) pulse oximetry ("P-Ox")) or (ii) the appearance of an electrical signal applied to the owner (i.e. the person in whom the apparatus to be controlled is implanted) which may not be a pacing signal—either internally or externally. The fingerprint has the advantage of being able to be inputted from a point on the body which is in extremely close proximity to either (1) an ECG signal (which can be obtained from one finger and another body part) or (2) a P-Ox-based measure of the heart rate. Many other combinations of biologic identifier and manipulatable/observable physical signs are possible including:

- a camera which images both carotid artery pulsation and the face, each pertaining to the same person, at essentially the same time. (Of necessity, absolute simultaneity is not possible here, in part because of the time it takes to obtain an image, and in part because some measures require the passage of at least one interval between heartbeats);
- a camera which images both carotid artery pulsation and the iris of an eye, each pertaining to the same person, at essentially the same time. In the case of this combination of observations, and in other cases stated hereinbelow, iris identification can be enhanced by the application of an amount of light that is controlled by the user; this approach is presented in inventor's U.S. patent application Ser. No. 13/563,399, now allowed, and incorporated herein in its entirety;
- a camera which images both jugular venous pulsation and the face, each pertaining to the same person, at essentially the same time;
- a camera which images both jugular venous pulsation and the iris of an eye, each pertaining to the same person, at essentially the same time; and
- a camera which images retinal vascular pulsations, and the iris of an eye, each pertaining to the same person, at essentially the same time.

Furthermore stimulation techniques involving evoked cortical potentials and/or electroencephalographic recordings along with a biologic identifier are possible.

In the case in which one camera images both the biologic identifier and the physiologic parameter, it will be much harder to falsify the data generated by such an apparatus, than is the case in which different sensors must be used—e.g. ECG and fingerprint. Hereinbelow, various apparatus types are shown to minimize the likelihood of such falsification when a camera is not utilized (without precluding the possibility of adding a camera to any of the approaches herein).

Figure 30:
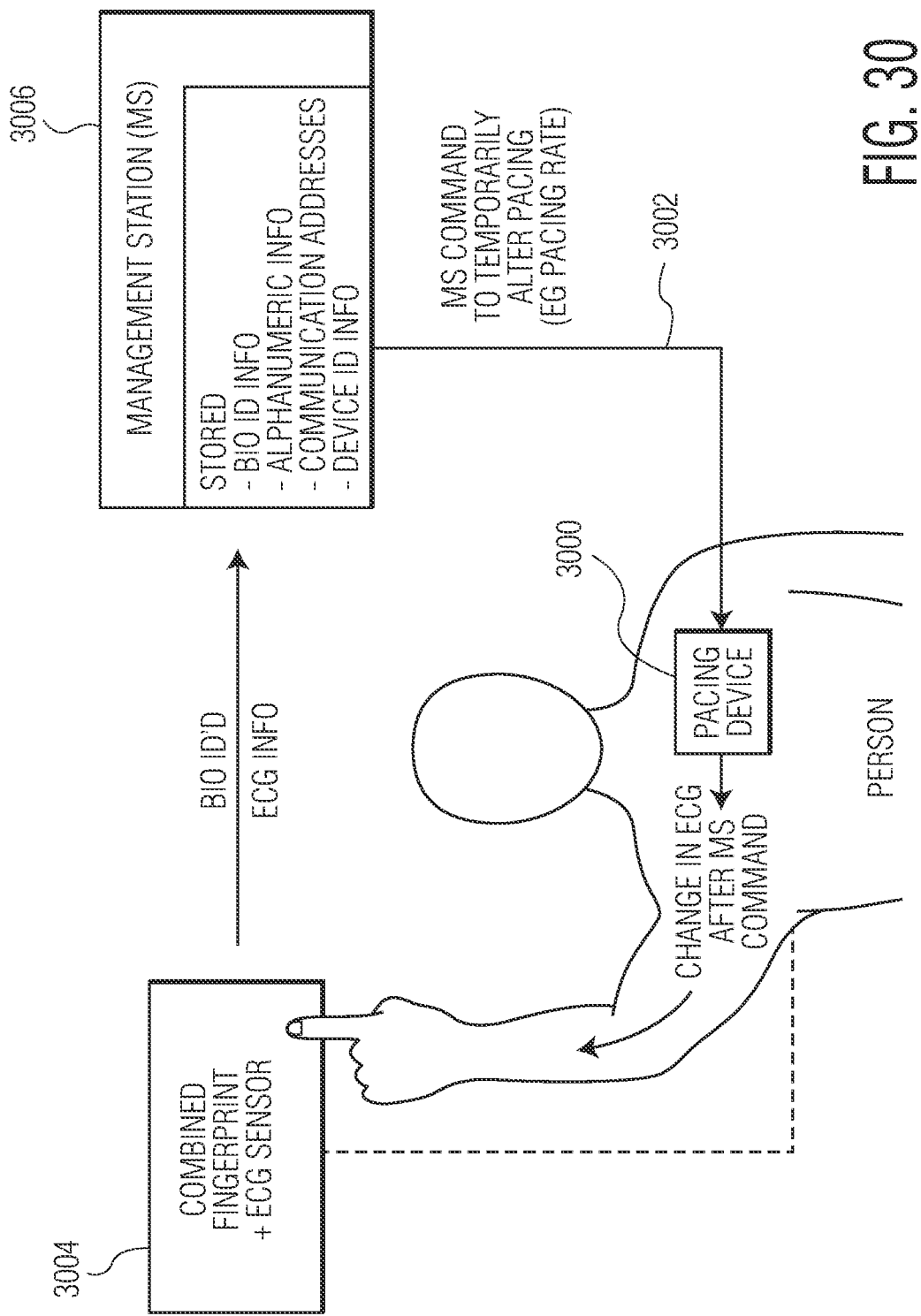
FIG. 30 is a representational block diagram of a pacing-based system for the remote identification of a device owner.

FIG. 30 is a representational block diagram of a pacing-based system for the remote identification of a device owner. The dashed line extending from the person to the combined fingerprint and ECG sensor simply acknowledges that ECG recording, whether unipolar or bipolar involves the attachment of at least two electrodes to the owner. The management station, administered by the user who may be a medical professional or the patient himself can make an initial identification based simply on the initially sent ECG and fingerprint information.

However, a far more robust identification is obtained by sending a signal 3002 to the owner's implanted pacing device 3000 which alters the pacing routine even for a short time. Such alteration could include changing the pacing rate by a small amount, changing an AV delay, providing one or more premature stimuli outside of the refractory period of the respective heart chamber, providing one or more premature stimuli inside of the refractory period of the respective heart chamber, or changing the amplitude or pulse width of a paced impulse. The composite ECG and fingerprint sensor provides comingled biologic and physiologic information at 3004, which is sent to management station 3006. Stored biologic identification samples allow identification of the user as discussed in the aforementioned '399 application. Stored communication address information allows for electronically "finding" device 3000.

Figure 32A:
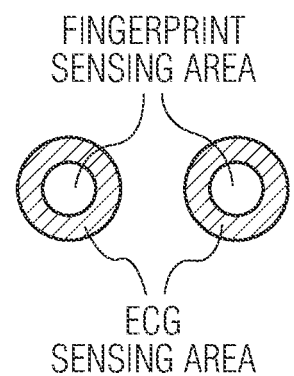
FIG. 32A-32E are representational diagrams of a composite sensor for sensing both electrocardiogram signals and a fingerprint.

FIGS. 32A to 32E show examples of such composite fingerprint and ECG sensors. In FIG. 32A, the fingerprint sensing area is central and the ECG sensing area forms the periphery. A prompt from the user/remote station to slightly move one finger would help to verify that a real finger is generating both the ECG and the fingerprint image, since the act of moving the finger slightly would result in an essentially unchanged ECG signal (after some momentary artifact at the time of the move), but would result in a changed version of the fingerprint image, reflecting its move. Two fingerprint sensing areas are shown in the figure; embodiments of the invention with either a greater or lesser number are possible.

Figure 32B:
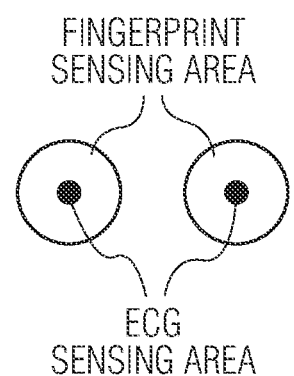

FIG. 32B shows an embodiment of the sensing apparatus in which the ECG sensing area is central and the fingerprint sensing area is peripheral. Again, a prompt to slightly move one finger while maintaining contact with the composite sensors generates even more reliable identification.

Figure 32C:
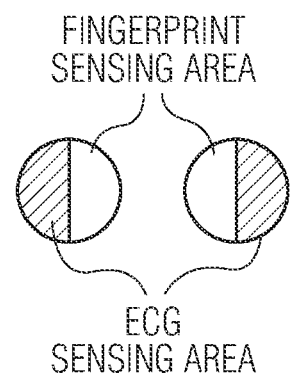
Figure 32D:
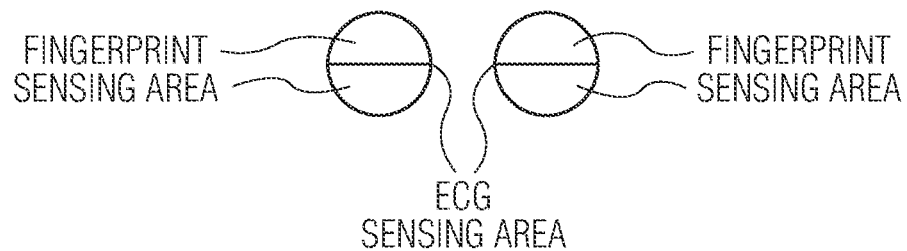
Figure 32E:
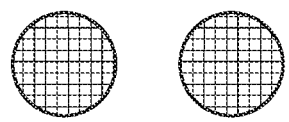

FIG. 32C shows an embodiment with semicircular ECG and fingerprint areas. In FIG. 32D, the ECG sensing area is linear, and could be any orientation including horizontal, as shown in the figure. In FIG. 32E the line of FIG. 32D is replaced by a grid of ECG sensitive conductive areas. Other configurations will occur to those skilled in the art.

Figure 31:
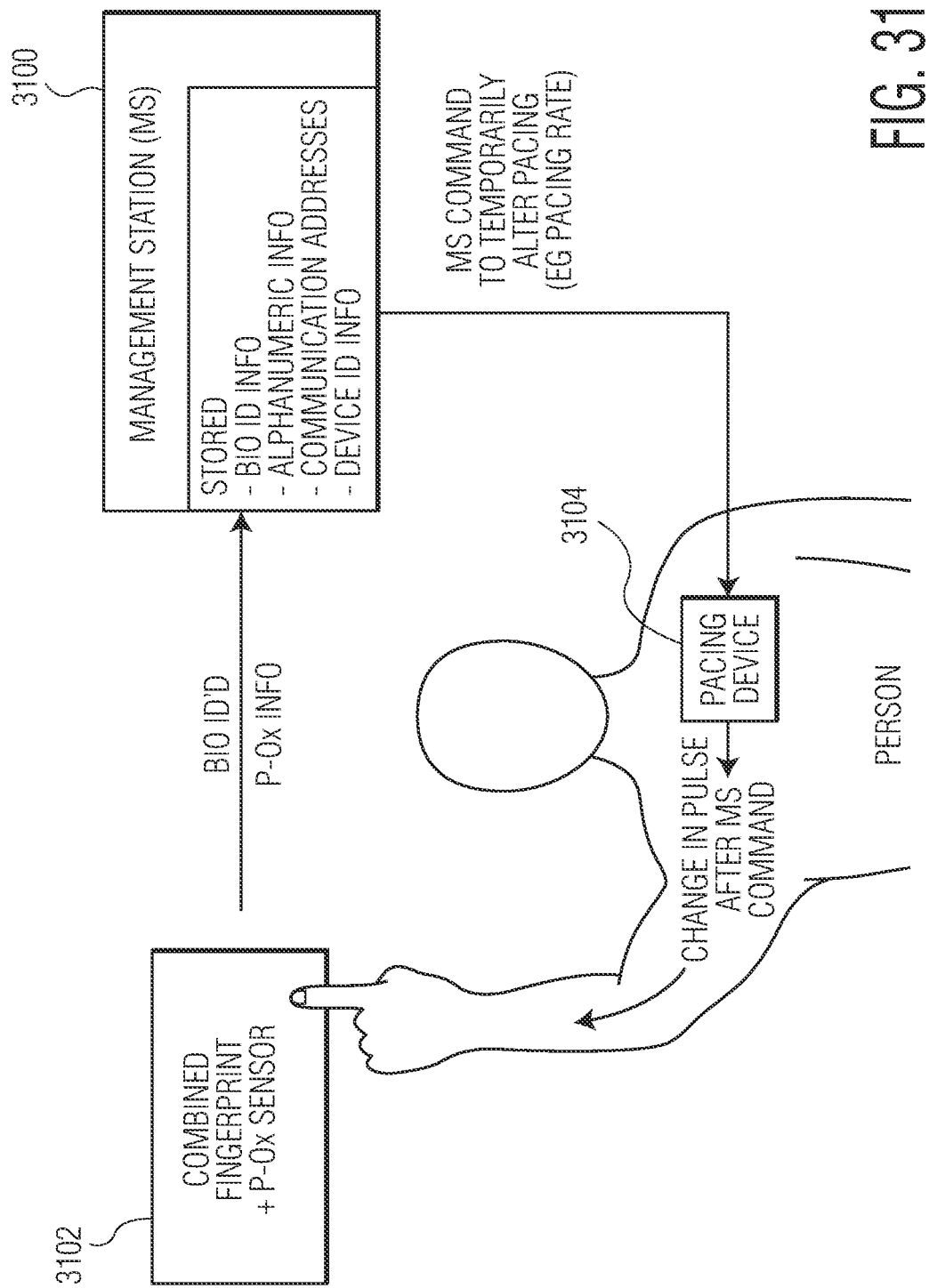
FIG. 31 another representational block diagram of a pacing-based system for the remote identification of a device owner.

FIG. 31 shows another representational block diagram of a pacing-based system for the remote identification of a device owner. The operation of this apparatus is similar to that of the apparatus shown in FIG. 30, except that in this case a pulse oximetry device is substituted for the ECG sensor. The remote command from 3100 to 3104 involves a change in pacing which would alter ventricular timing—in order to be observable by P-Ox. (Thus changes in pacing spike amplitude, pulse width etc., and the introduction of premature stimuli within the refractory period cannot be utilized for this embodiment.) 3102 senses the co-locational pulse oximetry and fingerprint data and presents it to 3100.

Figure 33A:
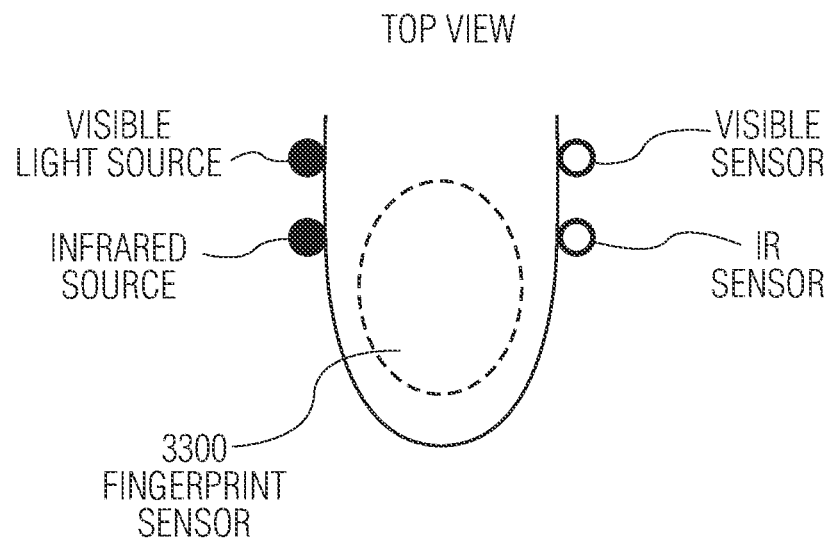
FIGS. 33A and 33b are representational top and side views of a composite sensor for sensing both pulse oximetry information and a fingerprint.
Figure 33B:
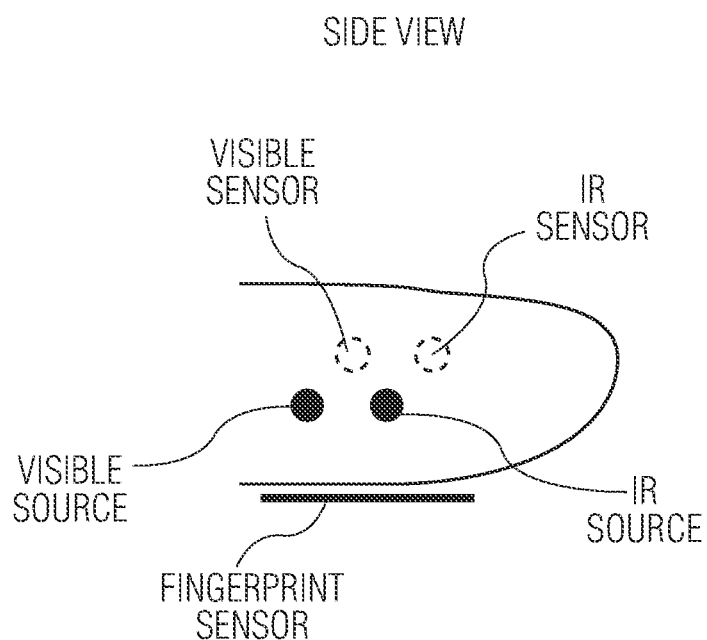

FIGS. 33A and 33B are representational top and side views of a composite sensor for sensing both pulse oximetry information and a fingerprint. The dotted elliptical area within FIG. 33A denotes ECG electrode 3300 situated beneath the distal part of the finger. In this example both a visible light source and sensor, and an infrared ("IR") source and sensor are utilized. Embodiments with larger or smaller numbers of sources and sensors are possible. FIG. 33B shows the same apparatus as does FIG. 33A, in side perspective. The dotted sensor outlines indicate placement behind the finger, in this view.

Figure 34:
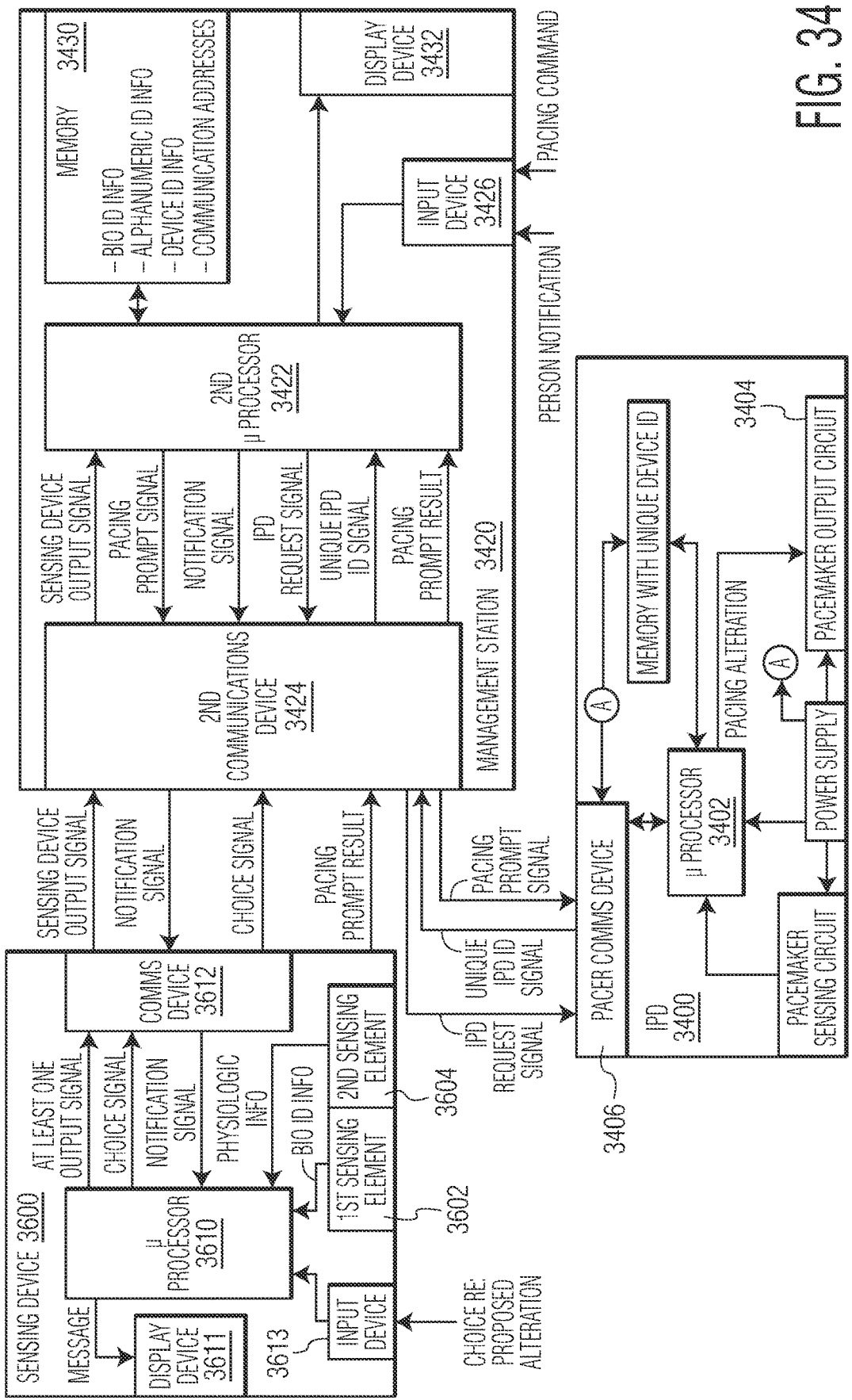
FIG. 34 is a block diagram of the pacing device-based embodiment of the invention.

FIG. 34 is a block diagram of the pacing device-based embodiment of the invention. Embodiments of the invention need not include all of the elements shown in this figure (or in other figures hereinabove and hereinbelow.) The implanted pacing device (IPD) 3400 is controlled by one or more microprocessors 3402. 3402 controls the pacemaker output circuit 3404. Processor 3422 of the management station 3420 produces a pacing prompt signal which is sent by communications device 3424 to the pacemaker receiving device 3406. The signal causes 3402 to execute any of the aforesaid pacing alterations. The choice of alteration may be input via 3426 or generated without input by 3422. The results of the pacing alteration are input to the sensing device 3600: the biologic information to sensing element 3602, and the physiologic information to the sensing element 3604. The sensor information is conveyed to station 3420 along the route 3610 to 3612 to 3424, after which processor 3422 analyzes the received information resulting from the pacing alteration generated at the management station. In particular it determines whether the expected alteration and the observed one are the same, and whether the biologic identifier(s) stored in memory 3430 are the same as those inputted to 3420 following the pacing alteration. The results may be displayed by 3432.

Figure 40:
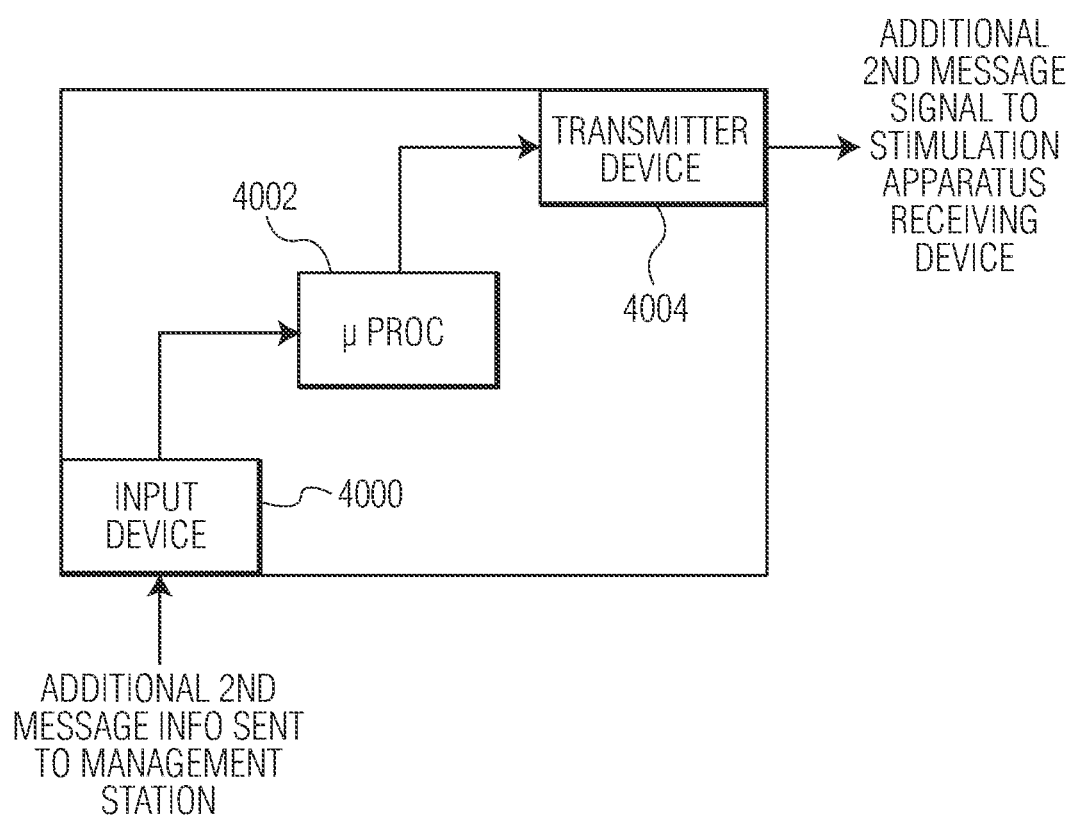
FIG. 40 is a block diagram of a another message sending device, in conjunction with the use of the stimulation-device based embodiment for secure communications.

The providing of fingerprint and pulse information by the owner amounts to tacit participation in user control. In some cases, if the user then wishes to change a parameter or program of the IPD or an IMD (which may include pacing apparatus, and thus be considered an IPD; or which may be a separate medical device associated with the same person as is the IPD), it might be assumed that the owner has tacitly accepted such change. However, a more detailed version of permission utilizing the apparatus of FIG. 34 would involve active patient notification by a signal inputted at 3426, to 3422, to 3424, to 3612 of the owner's sensing device, to 3610 to produce an explicit request presented by owner display device 3611. The owner (generally, a patient) responds if he/she chooses to via input device 3613, with signal flow successively to 3610, 3612, 3424, 3422 with display at 3432. 3420 may request and obtain a unique device identifier from the IPD as shown in the FIG. 40.

Figure 35A:
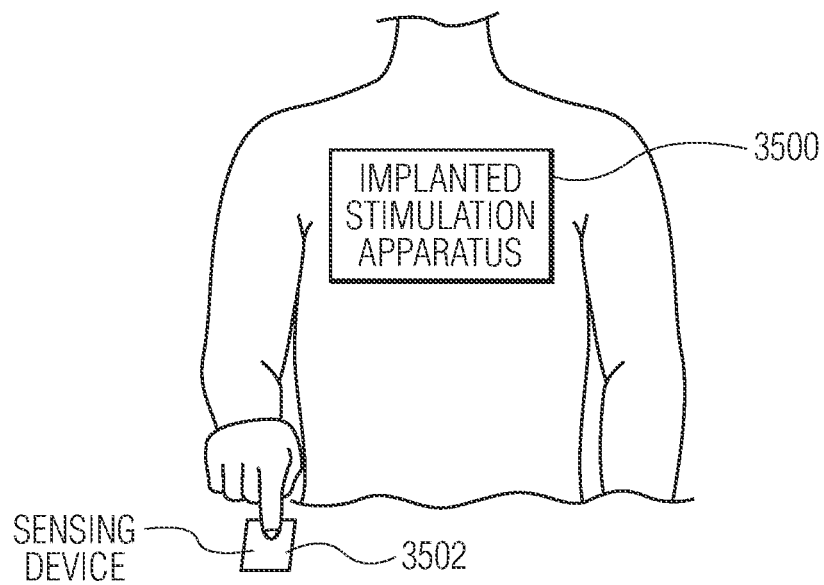
FIG. 35A is a representation diagram of the stimulation apparatus embodiment of the invention, with implanted stimulation apparatus.
Figure 35B:
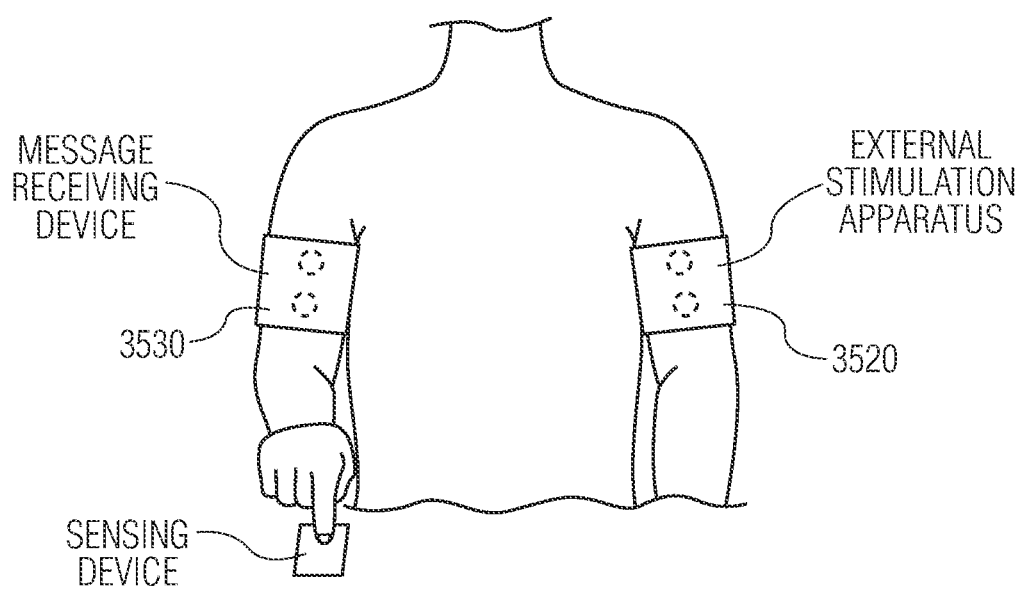
FIG. 35B is a representation diagram of the stimulation apparatus embodiment of the invention, with external stimulation apparatus, also showing an external version of a message receiving device.

FIG. 35A is a representational diagram of the stimulation apparatus embodiment of the invention, showing implanted stimulation apparatus. In this embodiment device 3500 is implanted in a body of the patient/owner. If the device is a non-pacing device, the implantation need not be in the thorax and could be in an arm. The ideal locations are both patient-friendly in terms of discomfort or conspicuousness, and will also generate a relatively high amplitude stimulus artifact. Thus the legs are a poor location if the IPD is situated in the thorax. Also shown in the figure is a finger engaging a co-mingled sensing set of inputs 3502. FIG. 35B indicates an external version of a stimulation apparatus 3520. It also shows an external message receiving device 3530. In each of 3520 and 3530, contact electrodes for touching the skin of the owner are shown as broken circles. The stimulation devices of this embodiment—besides being conventional pacemakers or ICDs, may be leadless pacemakers, or a stimulation device that does not pace at all but only produces electrical/spike "artifact signals for observation and/or electrical recording. (In the latter case, the term "ECG" is inaccurate, since the artifact is not a heart signal. The term "electrogram" or "spike" will be used hereinbelow, with the understanding that, as used hereinbelow "electrogram" does not refer to an intracardiac signal.)

Figure 36A:
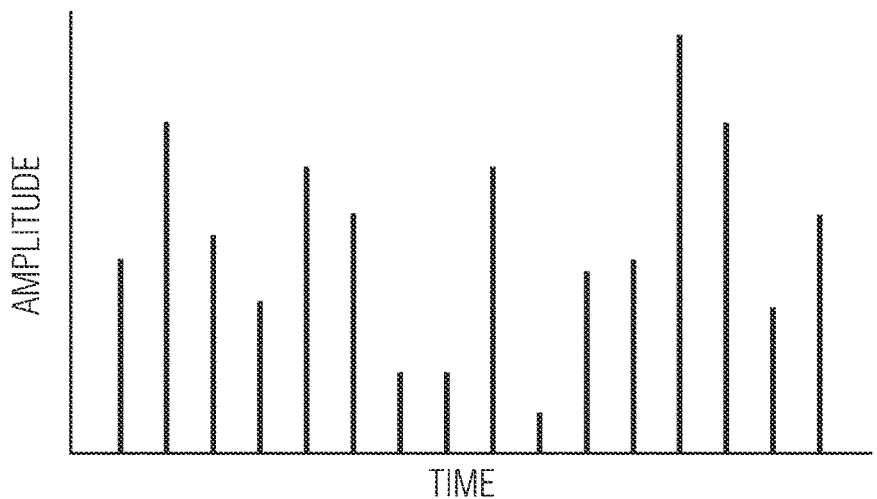
FIG. 36A-C are graphical illustrations of the modulation of stimulation device output in the amplitude, pulse width and inter-pulse interval domains.
Figure 36B:
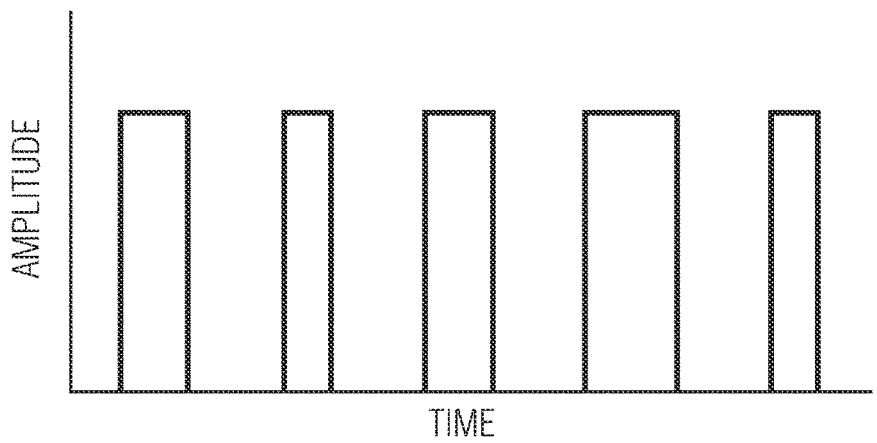
Figure 36C:
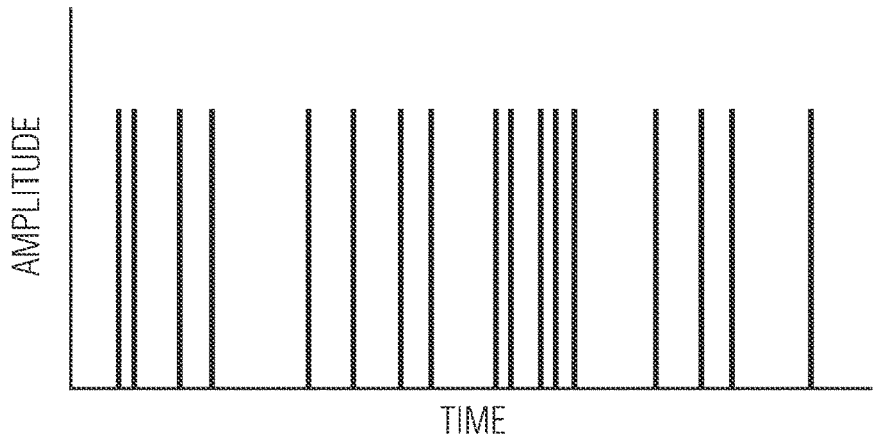

FIGS. 36A-C show versions examples of each of three types of pulse coding that may be utilized in embodiments of the invention. FIG. 36A shows amplitude coding, i.e. the embedding of information in the amplitude of a signal. For example if there are 8 possible choices of amplitude, then each spike will carry 3 bits of information. If there are 8 possible timings (e.g. with respect to either the last spike or the last R-wave), then timing information also conveys 3 bits of information per unit time. FIG. 36C shows timing modulation and FIG. 36B shows pulse width modulation.

Figure 37:
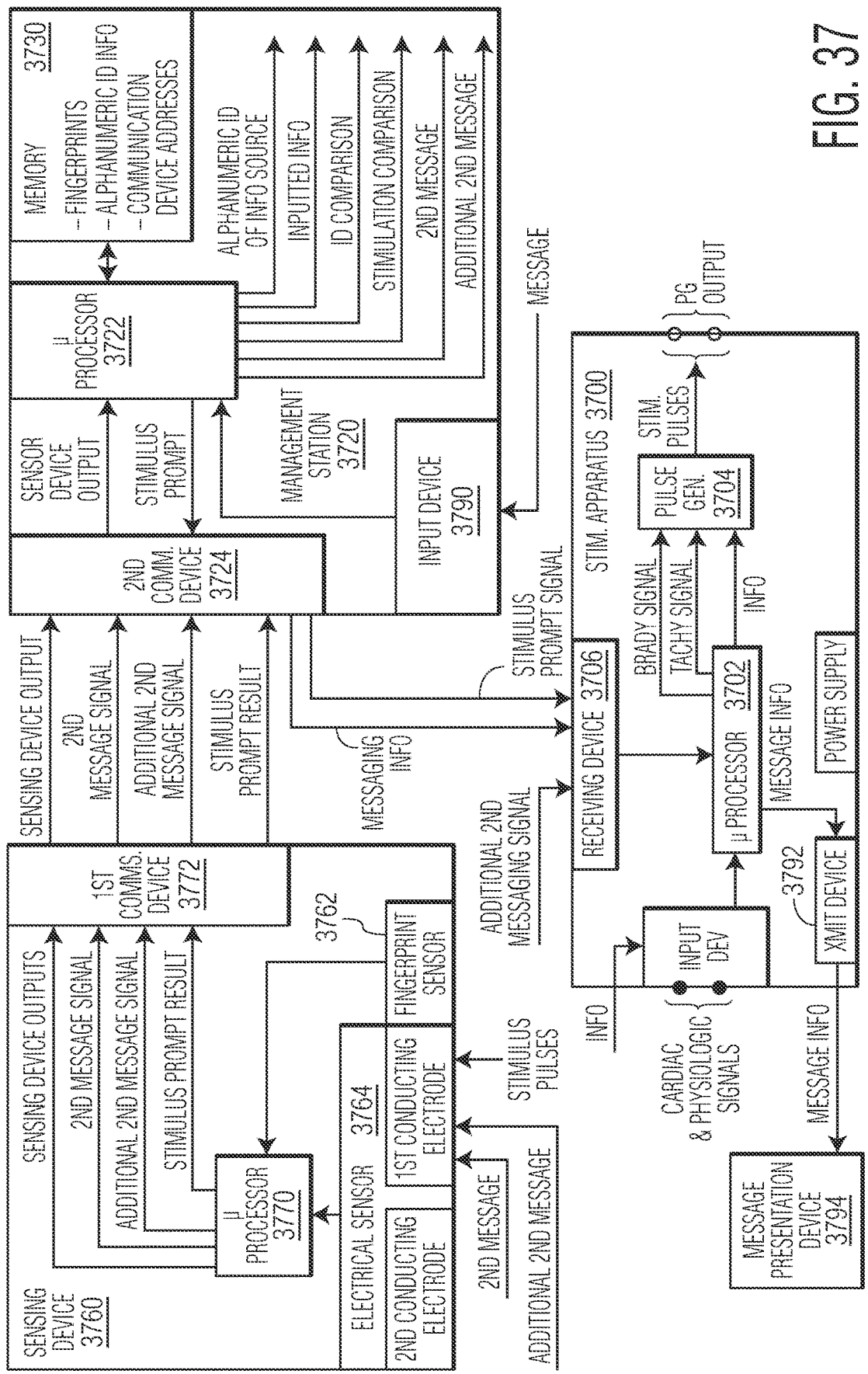
FIG. 37 is a block diagram of the stimulation device-based embodiment of the invention

FIG. 37 is a block diagram of the stimulation device-based embodiment of the invention.

In this embodiment, the stimulation apparatus (SA) 3700 which may be external—as shown by 3520 of FIG. 35B—or implanted, is controlled by one or more microprocessors 3702. 3702 controls the SA pulse generator circuit 3704. Analogous to FIG. 35B, the circles at the periphery of 3700 show the point of electrical contact of 3700 with the body of the owner. Processor 3722 of the management station 3720 produces a stimulus prompt signal which is sent by communications device 3724 to the receiving device 3706. The signal causes 3702 to execute any of the aforesaid stimulus alterations. The results of the stimulation are input to the sensing device 3760: the fingerprint information to sensing element 3762, and the physiologic information to the sensing element 3764. The sensor information is conveyed to station 3720 along the route 3770, to 3772, to 3724, after which processor 3722 analyzes the received information resulting from the stimulus generated at the management station. In particular it compares whether the expected stimulation(s) and the observed one or ones are the same, and whether the biologic identifier(s) stored in memory 3730 are the same as those inputted to 3720 following the stimulation. In this figure, notification devices, display devices and other features of the invention shown in FIG. 34, are not shown. However, these not-shown devices of the FIG. 34 device are intended to be applicable to the invention of FIG. 37 as well.

The apparatus of FIG. 37 can be used for the communication of messages between (1) the owner (that is the patient or person in whom device 3700 is implanted) and (2) the user (that is a person who inputs information to management station 3720, or obtains the 3720 output in message form (display device for 3720 not shown in the figure, but such a display device would be the recipient of each of the six information types shown in the lower right hand corner of element 3720—in particular two types of message transmission formats, discussed hereinbelow)).

In one format, a message is inputted by the user via input device 3790. It is encoded into a spike format by processor 3722 utilizing the encoding techniques discussed hereinabove, and others known in the art. The encoded message is transmitted via the route 3722 to 3724 to 3706 to 3702 to message transmitting device 3792 to message presentation device 3794. The value of the processing of the message in this fashion is that it allows the user to see exactly what message was received and who the owner—i.e. the receiving person—is. This occurs because a copy of the message is returned, with the owner's biologic identification, to the user through the sensing device along the route 3702 to 3704 followed by stimulation pulses traversing a portion of the owner's body to reach 3762/3764 to 3770 to 3772 to 3724 to 3722. Decoding of the message at the owner end can occur at either the SA microprocessor 3702, or at presentation device 3794.

Figure 38:
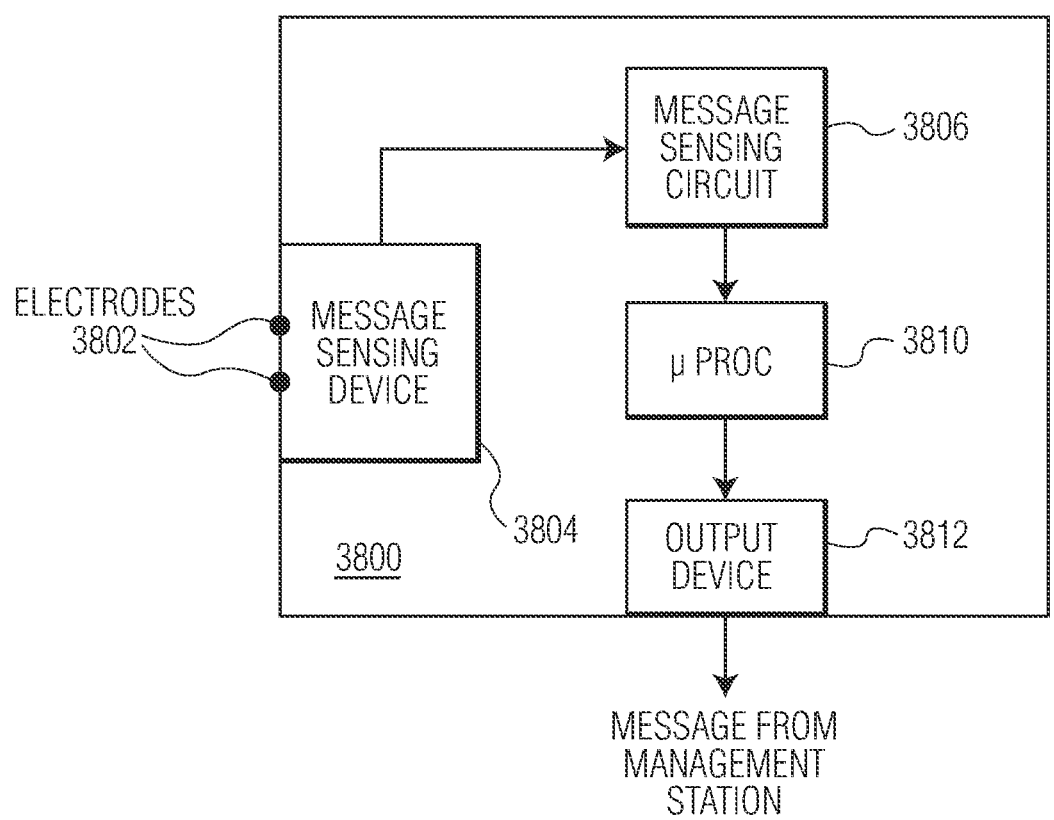
FIG. 38 is a block diagram of a message receiving device, in conjunction with the use of the stimulation-device based embodiment for secure communications.

FIG. 38 shows a message receiving device, an alternate means by which the owner may receive the message inputted at 3790 by the user. In this case, the microprocessor 3702 causes pulse generator 3704 (each shown in FIG. 37) to produce an output signal consisting of spikes applied to the owner, whose pattern contains the message. Free standing message receiving device 3800 (also shown by 3530 in FIG. 35B), with sensing device 3804 containing electrodes 3802 in contact with the skin of the owner, passes the information to message sensing circuit 3806, microprocessor 3810 and to output device 3812. Decoding can be by either the SA microprocessor 3702 or the message receiving device microprocessor 3810. This message is also returned to the user, biologically "stamped" for verification of biologic ID of the receiving person, and correctness of the message, as shown in FIG. 37.

Figure 39:
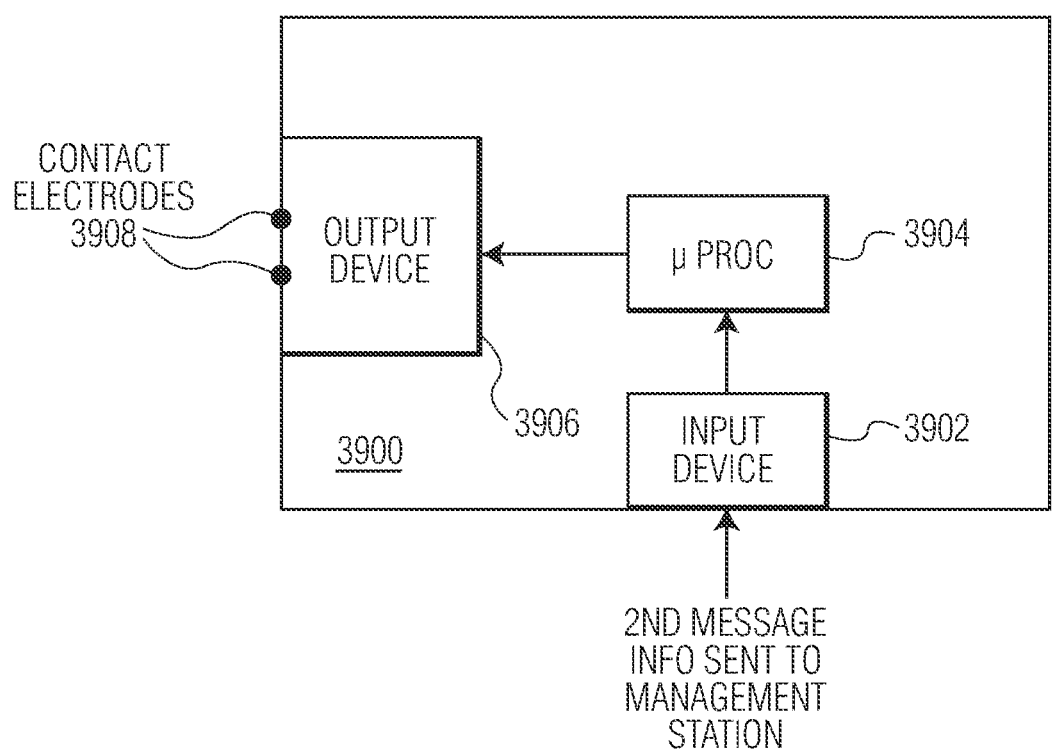
FIG. 39 is a block diagram of a message sending device, in conjunction with the use of the stimulation-device based embodiment for secure communications.

Message transmission from owner (e.g. patient) to user (at the management station) begins with one of two choices of input device. The message sending device 3900 of FIG. 39 (in which the message is referred to as "second message") calls for message input at 3902, followed by conversion/encoding to spike format by processor 3904, and output by output device 3906 containing contact electrodes 3908. These provide a "through the body" stimulus to sensing device 3760 (FIG. 37), which transmits the message to management station 3720 via the route, 3770, to 3772, to 3724, to 3722. 3722 decodes the coded message and may display or store it (display and storage devices not shown in this figure). Additional security information for assuring the owner that the user is the person he purports to be is discussed hereinabove, in conjunction with the parent application of the current application, spanning FIGS. 12-29 herein, and the associated specification. Further additional bidirectional secure communication could be achieved if each of the two communicating parties have both an implanted (or, less desirably, external) SA and sensing device and management station, i.e. duplicate arrangements. Finally, FIG. 40 (in which the message is referred to as "additional second message") shows an alternate apparatus for message inputting by the owner. Input device 4000 accepts a message, for coding by processor 4002, and transmission by 4004 to processor 3702 via 3706, to pulse generator 3704, to electrode input 3764 (via the PG output of 3700, as shown in FIG. 37) to processor 3770—after which the route of the message to the user is the same as in the case of the FIG. 39 device.

In either of the aforementioned scenarios, if at any time a biologic ID is found to be improper, or a returned message is found to be improper, message transmission could be halted immediately.

It is understood that many versions of the device of FIG. 38 and all of the figures and specification herein are possible each showing a greater or less number of components and various rearrangements of the components. It is further understood that all of these variants which perform the essential tasks herein are considered part of the inventions claimed herein.

The invention claimed is:

1. A communication system for providing the identity of a communicating person comprising
   (I) a stimulation device providing electrical stimulation to electrically conductive tissue of a body of the person, said stimulation device including:
      (A) at least one input device configured to input information to be encoded, said at least one input device operative to produce at least one first output signal representing said inputted information;
      (B) a pulse generator for producing at least one pulse generator output signal comprising at least one stimulation pulse configured to electrically stimulate a body of said person;
      (C) at least one first microprocessor, coupled to each of said input device and said pulse generator, for
         receiving said at least one first output signal;
         generating at least one second output signal specifying at least one electrical pulse representing said inputted information;
         providing said at least one second output signal to said pulse generator, said at least one second output signal configured to cause said pulse generator to produce said at least one stimulation pulse;
      (D) a power supply coupled to each of said at least one input device, said pulse generator and said at least one first microprocessor, for providing electrical power to maintain the operation of each of said input device, pulse generator and first microprocessor;
      wherein said at least one pulse generator output signal represents the inputted information;
      and further comprising
   (II) a sensing device, said sensing device including:
      (1) at least one first sensing element configured and arranged to sense a pattern of a fingerprint of a finger of said person and to generate an electrical signal representing said pattern; and
      (2) at least one second sensing element configured to input information representing electrical signals obtained from said person, including a representation of said pulse generator output signal specifying the inputted information; wherein said at least one second sensing element includes a first conductive element arranged to contact the finger which provides said fingerprint, and at least one second conductive element arranged to contact at least one other body part of said person;
      (3) at least one second microprocessor, coupled to each of said at least one first sensing element and said at least one second sensing element configured to receive each of said fingerprint information and said electrical signal information and configured to produce at least one sensing device output signal representing said information; and
      (4) a first communications device, coupled to said at least one second microprocessor, configured to transmit said at least one sensing device output signal;
      wherein said at least one second microprocessor is further operative to cause said first communications device to transmit said at least one sensing device output signal;
      wherein said sensing device output signal provides evidence of a linkage between the person whose finger is the source of said fingerprint and the person whose body is the source of said inputted information; and
      wherein said sensing device output signal provides evidence of receipt by said person of said information inputted by said at least one input device.

2. The apparatus defined in claim 1, wherein said stimulation device is implanted within the body of said person and wherein said pulse generator output signal is coupled to conductive elements arranged to contact a tissue of said body, whereby said pulse generator is operative to provide said at least one stimulation pulse representing said information to said tissue.

3. The apparatus defined in claim 2, wherein
   (A) one said input device is coupled to and operative to receive a signal from said conductive elements, said signal representing physiologic information pertaining to said person, said elements arranged to provide signals representing electrical activity of a heart of said person;
- (B) said at least one first microprocessor is further operative to provide at least one bradycardia signal to said pulse generator in response to receipt of physiologic information specifying a bradycardia, causing said generator to provide a plurality of bradycardia pulses for stimulating said heart, thereby to provide treatment of said a bradycardia;
- wherein timing of said bradycardia pulses is dependent upon said physiologic information provided to said at least one microprocessor by said one input device;
- whereby said stimulation device performs the dual function of (1) an implanted pacing device for stimulating the heart of said person in the event of bradycardia, and (2) providing said tissue stimulation representing said incoming identification information.

4. The apparatus defined in claim 3, wherein each of said pulse generator and said input device are coupled to at least one lead wire, at least a portion of said wire arranged in proximity to said heart, said wire configured to
- provide said pulse generator output to said heart; and
- provide a signal representing electrical activity of said heart to said one input device.

5. The apparatus defined in claim 4, wherein said at least one first microprocessor is further operative to detect a tachycardia and to provide a tachycardia signal to said pulse generator and wherein said pulse generator is further operative to provide at least one tachycardia pulse configured to stimulate said heart, thereby to treat said tachycardia.

6. The apparatus defined in claim 2, wherein an energy content of each of said stimulation pulses representing said inputted information is insufficient to induce electrical activation of a heart of said person.

7. The apparatus defined in claim 1, wherein said stimulation device is located external to said body of said person, and wherein said pulse generator is adapted to provide said at least one stimulation pulse representing information to conductive elements in contact with electrically conductive tissue on an external surface of said body.

8. The apparatus defined in claim 1, wherein said at least one first microprocessor is further operative to encode said inputted identification information by causing said pulse generator to provide a plurality of pulses, each said pulse having an amplitude; and wherein said inputted information is encoded as a sequence of said pulse amplitudes.

9. The apparatus defined in claim 1, wherein said at least one first microprocessor is further operative to encode said inputted identification information by causing said pulse generator to provide a plurality of pulses, each said pulse having a pulse width; and wherein said inputted information is encoded as a sequence of said pulse widths.

10. The apparatus defined in claim 1, wherein said at least one first microprocessor is further operative to encode said inputted information by causing said pulse generator to provide a plurality of pulses; and wherein said inputted information is encoded as a sequence of intervals between consecutive ones of said pulses.

11. The apparatus defined in claim 1, wherein
- (A) another input device is operative to receive a heart signal from at least two conductive elements arranged to represent a timing of electrical activation of said heart, and to provide said heart signal to said at least one first microprocessor;
- (B) said at least one first microprocessor is further operative to encode said inputted information by causing said pulse generator to provide a plurality of pulses, each said pulse timed to occur a variable interval of time after a most recent cardiac electrical activation, said timing of said most recent cardiac electrical activation being based on said heart signal;
- wherein said inputted information is encoded as variations in said intervals.

12. The system defined in claim 1, further comprising a management station including:
- (1) a second communications device, configured to receive said at least one sensing device output signal; and to transmit said information to said stimulation device;
- (2) a memory device configured to store and provide (i) fingerprint information pertaining to at least one registered person who is authorized to transmit said at least one sensing device output signal to said management station, and (ii) alphanumeric information indicating an identity of each registered person;
- (3) at least one third microprocessor, coupled to each of said second communications device and to said memory device, configured to
  - (a) process said at least one sensing device output signal and to provide an output indicating the alphanumeric identification of the person who is the source of the received sensing device output signal; and
  - (b) provide said inputted information.

13. The system defined in claim 12, wherein said at least one third microprocessor is further operative
- (i) to produce a stimulation prompt signal, and
- (ii) to cause said second communications device to transmit said signal;

and wherein:
- (i) one particular stimulation device associated with a particular registered person further comprises a receiving device having a particular communications address, coupled to said at least one first microprocessor configured to receive at least one signal from said second communications device;
- (ii) said memory device further stores and provides a communications address for a stimulation device of each registered person;
- (iii) said second communications device is operative to transmit said stimulation prompt signal to said particular stimulation device associated with said particular communications address, said stimulation prompt specifying a particular stimulation pattern for production by said pulse generator of said particular stimulation device;
- (iv) said at least one first microprocessor is further operative to cause said pulse generator to generate said particular pattern of stimuli, following the receipt of said stimulation prompt signal;
- (v) in response to said particular pattern of stimuli, said sensing device is further operative to generate at least one output signal reflecting both said particular pattern of stimuli and said fingerprint information, said first communications device is operative to transmit a signal representing both said particular pattern of stimuli and said fingerprint information, and said management station communications device is further operative to receive said signal;

(vi) said at least one third microprocessor is operative to determine and indicate the results of a first comparison between
(a) the received sensing device output signal reflecting both said particular pattern of stimuli and said fingerprint information, and
(b) the particular stimulation pattern specified by the transmitted stimulation prompt signal; and
(vii) said at least one third microprocessor is further operative to determine and indicate the results of a second comparison between
(a) said stored fingerprint information of said particular registered person, and
(b) said received fingerprint information;
wherein, based on said first comparison and said second comparison:
a determination is made, at said management station, of whether a recipient of said stimulation prompt signal is an intended recipient of said stimulation prompt signal;
thereby assuring that a management station output signal reaches only the intended recipient.

14. The system defined in claim 13, wherein said stimulation device further includes a message receiving device coupled to said at least one first microprocessor and said management station further comprises a management input device, coupled to said at least one third microprocessor, configured to input messaging information, and wherein:
(a) said at least one third microprocessor is further operative to cause said second communications device to transmit said messaging information to said message receiving device; and
(b) said message receiving device is operative to receive said messaging information and to provide said messaging information to said at least one first microprocessor.

15. The system defined in claim 14, wherein
(a) said stimulation device further comprises a transmitting device, coupled to one of said at least one first microprocessor, configured to transmit said messaging information to a message presentation device; and
(b) said one first microprocessor is operative to process and provide said received messaging information; and to provide said information to said transmitting device;
whereby said person receives said messaging information inputted at said management station.

16. The system defined in claim 14, wherein
(a) at least one of said at least one first microprocessor is operative to cause said pulse generator to produce an output signal representing said messaging information;
(b) said system further comprises a message receiving device comprising:
(1) a message sensing device comprising at least two contact electrodes for contacting said body and receiving said signal outputted by said pulse generator representing said messaging information, coupled to a message sensing circuit for outputting a message signal;
(2) at least one fourth microprocessor, coupled to said message sensing circuit configured to receive said message signal, and configured to produce an output representing the information contained in said messaging information inputted at said management station; and
(3) a message output device, coupled to said at least one fourth microprocessor, for outputting said messaging information;
whereby said person receives said message inputted at said management station.

17. The system defined in claim 13, further comprising a message sending device, configured to input second messaging information, comprising:
(a) a second messaging input device, configured to input said second messaging information;
(b) at least one fifth microprocessor, coupled to said second messaging input device;
(c) a second messaging output device, coupled to said at least one fifth microprocessor, configured to provide a second messaging signal representing said second messaging information; and
(d) at least two contact electrodes, coupled to said second messaging output device, configured to provide said messaging device output signal, arranged for application to said body of said person;
wherein said at least one second sensing element is further operative to sense said second messaging signal;
wherein said at least one second microprocessor of said sensing device is further operative to receive said second messaging signal and to cause said first communications device to transmit said second messaging information to said management station;
and wherein said second communications device is further operative to receive said second messaging signal and to provide said signal to said at least one third microprocessor and to cause said at least one third microprocessor to provide said second messaging information;
whereby said second messaging information is provided from said message sending device to said sensing device and thence to said management station.

18. The system defined in claim 14, further comprising an additional message sending device, configured to input additional second messaging information for transmission to said management station, comprising:
(a) an additional second messaging input device, configured to input said additional second messaging information;
(b) at least one sixth microprocessor, coupled to said additional second messaging input device; and
(c) an additional second messaging transmitting device, coupled to said at least one sixth microprocessor, configured to provide an additional second messaging signal representing said additional second messaging information; and
wherein said stimulation device message receiving device is further operative to receive said additional second messaging signal;
wherein one of said at least one microprocessors of said stimulation device is operative to cause said pulse generator to produce a pulse generator output signal representing said additional second messaging signal;
wherein said at least one second microprocessor of said sensing device is further operative to sense said additional second messaging signal and to cause said first communications device to transmit said additional second messaging information to said management station;
and wherein said second communications device is further operative to receive said additional second messaging signal and to provide said signal to said at least one third microprocessor and to cause said at least one third microprocessor to provide said additional second messaging information;

whereby said additional second messaging information is provided from said additional message sending device to said stimulation device, thence to said sensing device and thence to said management station.

19. The system defined in claim 13, further comprising an additional management input device, coupled to said third microprocessor, for inputting a command which specifies (a) said stimulation prompt, and (b) information related to the identity of said particular recipient stimulation device; wherein said input device is configured to produce a signal representing said command.

* * * * *